(12) United States Patent
Sweeney et al.

(10) Patent No.: US 10,806,352 B2
(45) Date of Patent: *Oct. 20, 2020

(54) WIRELESS VASCULAR MONITORING IMPLANTS

(71) Applicant: Foundry Innovation & Research 1, Ltd., Dublin (IE)

(72) Inventors: Fiachra M. Sweeney, Dublin (IE); Hanson S. Gifford, III, Woodside, CA (US); Jessi Johnson, Sunnyvale, CA (US); Pablo Martin, Dublin (IE); Shriram Raghunathan, Menlo Park, CA (US); Stephen Sheridan, Co Cavan (IE); Douglas S. Sutton, Pacifica, CA (US); Friedrich Wetterling, Dublin (IE); Conor M. Hanley, Dublin (IE)

(73) Assignee: Foundry Innovation & Research 1, Ltd., Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,183

(22) Filed: Oct. 31, 2018

(65) Prior Publication Data

US 2019/0076033 A1   Mar. 14, 2019

Related U.S. Application Data

(63) Continuation-in-part of application No. PCT/US2017/063749, filed on Nov. 29, 2017, and a
(Continued)

(51) Int. Cl.
*A61B 5/0215* (2006.01)
*A61B 5/00* (2006.01)
(Continued)

(52) U.S. Cl.
CPC ........ *A61B 5/02152* (2013.01); *A61B 5/0022* (2013.01); *A61B 5/0031* (2013.01);
(Continued)

(58) Field of Classification Search
None
See application file for complete search history.

(56) References Cited

U.S. PATENT DOCUMENTS 3,568,661 A   3/1971   Franklin
RE32,361 E   2/1987   Duggan
(Continued)

FOREIGN PATENT DOCUMENTS

DE   102005035022 A1   11/2006
EP   0897285 A1   2/1999
(Continued)

OTHER PUBLICATIONS

Voroneanu et. al., "The relationship between chronic volume overload 3 and elevated blood pressure in hemodialysis patients: 4 use of bioimpedance provides a different perspective 5 from echocardiography and biomarker methodologies," Int Urol Nephrol, Sep. 2010; 42(3):789-97.
(Continued)

*Primary Examiner* — Kaylee R Wilson
*Assistant Examiner* — Jay B Shah
(74) *Attorney, Agent, or Firm* — Downs Rachlin Martin PLLC

(57) ABSTRACT

Wireless, variable inductance and resonant circuit-based vascular monitoring devices, systems, methodologies, and techniques are disclosed that can be used to assist healthcare professionals in predicting, preventing, and diagnosing various heart-related and other health conditions.

4 Claims, 31 Drawing Sheets

Related U.S. Application Data continuation-in-part of application No. PCT/US2017/046204, filed on Aug. 10, 2017.

(60) Provisional application No. 62/534,329, filed on Jul. 19, 2017, provisional application No. 62/427,631, filed on Nov. 29, 2016.

(51) Int. Cl.

| | | |
|---|---|---|
| *A61B 5/07* | (2006.01) | |
| *A61F 2/82* | (2013.01) | |
| *A61B 5/02* | (2006.01) | |
| *G16H 40/63* | (2018.01) | |
| *G16H 50/30* | (2018.01) | |
| *A61B 5/107* | (2006.01) | |
| *G16H 50/20* | (2018.01) | |
| *A61B 5/0205* | (2006.01) | |

(52) U.S. Cl.
CPC .......... *A61B 5/02007* (2013.01); *A61B 5/076* (2013.01); *A61B 5/1076* (2013.01); *A61B 5/4875* (2013.01); *A61B 5/686* (2013.01); *A61B 5/6869* (2013.01); *A61B 5/6876* (2013.01); *A61B 5/6882* (2013.01); *A61B 5/7225* (2013.01); *A61F 2/82* (2013.01); *G16H 40/63* (2018.01); *G16H 50/20* (2018.01); *G16H 50/30* (2018.01); *A61B 5/0205* (2013.01); *A61B 2560/0219* (2013.01); *A61B 2560/066* (2013.01); *A61B 2562/0247* (2013.01); *A61B 2562/12* (2013.01); *A61F 2250/0002* (2013.01)

(56) References Cited

U.S. PATENT DOCUMENTS

| | | | |
|---|---|---|---|
| 4,926,875 A | 5/1990 | Rabinovitz et al. | |
| 4,947,852 A | 8/1990 | Nassi et al. | |
| 5,127,404 A | 7/1992 | Wyborny et al. | |
| 5,205,292 A | 4/1993 | Czar et al. | |
| 5,316,001 A | 5/1994 | Ferek-Petric et al. | |
| 5,339,816 A | 8/1994 | Akamatsu et al. | |
| 5,495,852 A | 3/1996 | Stadler et al. | |
| 5,630,836 A | 5/1997 | Prem et al. | |
| 5,752,522 A | 5/1998 | Murphy | |
| 5,872,520 A | 2/1999 | Siefert et al. | |
| 5,902,308 A | 5/1999 | Murphy | |
| 5,967,986 A * | 10/1999 | Cimochowski ...... | A61B 5/0031 |
| | | | 600/454 |
| 6,010,511 A | 1/2000 | Murphy | |
| 6,012,457 A | 1/2000 | Lesh | |
| 6,015,386 A | 1/2000 | Kensey et al. | |
| 6,025,725 A | 2/2000 | Gershenfeld et al. | |
| 6,039,701 A | 3/2000 | Sliwa et al. | |
| 6,053,873 A | 4/2000 | Govari et al. | |
| 6,111,520 A | 8/2000 | Allen et al. | |
| 6,115,633 A | 9/2000 | Lang et al. | |
| 6,115,636 A | 9/2000 | Ryan | |
| 6,164,283 A | 12/2000 | Lesh | |
| 6,206,835 B1 | 3/2001 | Spillman, Jr. et al. | |
| 6,231,516 B1 | 5/2001 | Keilman et al. | |
| 6,261,233 B1 | 7/2001 | Kantorovich | |
| 6,278,379 B1 | 8/2001 | Allen et al. | |
| 6,287,253 B1 | 9/2001 | Ortega et al. | |
| 6,325,762 B1 | 12/2001 | Tjin | |
| 6,339,816 B1 | 1/2002 | Bausch | |
| 6,354,999 B1 | 3/2002 | Dgany et al. | |
| 6,398,734 B1 | 6/2002 | Cimochowski et al. | |
| 6,434,411 B1 | 8/2002 | Duret | |
| 6,503,202 B1 | 1/2003 | Hossack et al. | |
| 6,574,510 B2 | 6/2003 | Von Arx et al. | |
| 6,673,020 B2 | 1/2004 | Okada et al. | |
| 6,699,186 B1 | 3/2004 | Wolinsky et al. | |

| | | |
|---|---|---|
| 6,738,671 B2 | 5/2004 | Christophersom et al. |
| 6,802,811 B1 | 10/2004 | Slepian |
| 6,855,115 B2 | 2/2005 | Fonseca |
| 6,926,670 B2 | 8/2005 | Rich et al. |
| 6,972,553 B2 | 12/2005 | Petrovich et al. |
| 7,065,409 B2 | 6/2006 | Mazar |
| 7,077,812 B2 | 7/2006 | Naghavi |
| 7,082,330 B2 | 7/2006 | Stadler et al. |
| 7,147,604 B1 | 12/2006 | Allen |
| 7,149,587 B2 | 12/2006 | Wardle et al. |
| 7,191,013 B1 | 3/2007 | Miranda et al. |
| 7,225,032 B2 | 5/2007 | Schmeling et al. |
| 7,233,821 B2 | 6/2007 | Hettrick et al. |
| 7,236,821 B2 | 6/2007 | Cates et al. |
| 7,245,117 B1 | 7/2007 | Joy |
| 7,284,442 B2 | 10/2007 | Fleischman et al. |
| 7,367,984 B2 | 5/2008 | Kulcinski et al. |
| 7,423,496 B2 | 9/2008 | Scheuermann |
| 7,432,723 B2 | 10/2008 | Ellis |
| 7,439,723 B2 | 10/2008 | Allen |
| 7,444,878 B1 | 11/2008 | Pepples |
| 7,452,334 B2 | 11/2008 | Gianchandani et al. |
| 7,454,244 B2 | 11/2008 | Kassab et al. |
| 7,466,120 B2 | 12/2008 | Miller |
| 7,479,112 B2 | 1/2009 | Sweeney et al. |
| 7,481,771 B2 | 1/2009 | Fonseca |
| 7,492,144 B2 | 2/2009 | Powers |
| 7,498,799 B2 | 3/2009 | Allen |
| 7,550,978 B2 | 6/2009 | Joy |
| 7,574,792 B2 | 8/2009 | O'Brien |
| 7,595,647 B2 | 9/2009 | Kroh |
| 7,618,363 B2 | 11/2009 | Yadav |
| 7,621,036 B2 | 11/2009 | Cros |
| 7,621,876 B2 | 11/2009 | Hoctor et al. |
| 7,647,831 B2 | 1/2010 | Corcoran |
| 7,647,836 B2 | 1/2010 | O'Brien |
| 7,662,653 B2 | 2/2010 | O'Brien |
| 7,667,547 B2 | 2/2010 | Ellis |
| 7,677,107 B2 | 3/2010 | Nunez |
| 7,678,135 B2 | 3/2010 | Maahs et al. |
| 7,679,355 B2 | 3/2010 | Allen |
| 7,699,059 B2 | 4/2010 | Fonseca |
| 7,710,103 B2 | 5/2010 | Powers |
| 7,725,160 B2 | 5/2010 | Weber |
| 7,748,277 B2 | 7/2010 | O'Brien |
| 7,778,684 B2 | 8/2010 | Weber et al. |
| 7,786,867 B2 | 8/2010 | Hamel et al. |
| 7,812,416 B2 | 10/2010 | Courcimault |
| 7,829,363 B2 | 11/2010 | You |
| 7,839,153 B2 | 11/2010 | Joy |
| 7,848,813 B2 | 12/2010 | Bergelson et al. |
| 7,854,172 B2 | 12/2010 | O'Brien |
| 7,908,002 B2 | 3/2011 | Hoijer |
| 7,908,018 B2 | 3/2011 | O'Brien |
| 7,909,770 B2 | 3/2011 | Stern |
| 7,932,732 B2 | 4/2011 | Ellis |
| 7,936,174 B2 | 5/2011 | Ellis |
| 7,955,269 B2 | 6/2011 | Stahmann |
| 7,966,886 B2 | 6/2011 | Corcoran |
| 7,988,719 B2 | 8/2011 | Alt et al. |
| 8,016,766 B2 | 9/2011 | Goedje et al. |
| 8,021,307 B2 | 9/2011 | White |
| 8,025,625 B2 | 9/2011 | Allen |
| 8,026,729 B2 | 9/2011 | Kroh |
| 8,060,214 B2 | 11/2011 | Larson et al. |
| 8,078,274 B2 | 12/2011 | Kassab |
| 8,082,032 B2 | 12/2011 | Kassab et al. |
| 8,099,161 B2 | 1/2012 | Kassab |
| 8,107,248 B2 | 1/2012 | Shin et al. |
| 8,111,150 B2 | 2/2012 | Miller |
| 8,114,143 B2 | 2/2012 | Kassab et al. |
| 8,118,749 B2 | 2/2012 | White |
| 8,154,389 B2 | 4/2012 | Rowland |
| 8,159,348 B2 | 4/2012 | Ellis |
| 8,185,194 B2 | 5/2012 | Kassab |
| 8,209,033 B2 | 6/2012 | Zhang et al. |
| 8,221,405 B2 | 7/2012 | Whisenant et al. |
| 8,237,451 B2 | 8/2012 | Joy |
| 8,264,240 B2 | 9/2012 | Park |

(56) References Cited

U.S. PATENT DOCUMENTS

| | | |
|---|---|---|
| 8,267,954 B2 | 9/2012 | Decant, Jr. et al. |
| 8,278,941 B2 | 10/2012 | Kroh |
| 8,298,147 B2 | 10/2012 | Huennekens et al. |
| 8,298,148 B2 | 10/2012 | Furman |
| 8,353,841 B2 | 1/2013 | White |
| 8,355,777 B2 | 1/2013 | White |
| 8,356,399 B2 | 1/2013 | Kaplan |
| 8,360,984 B2 | 1/2013 | Yadav |
| 8,374,689 B2 | 2/2013 | Gopinathan et al. |
| 8,432,265 B2 | 4/2013 | Rowland |
| 8,442,639 B2 | 5/2013 | Walker et al. |
| 8,465,436 B2 | 6/2013 | Griswold |
| 8,465,452 B2 | 6/2013 | Kassab |
| 8,467,854 B2 | 6/2013 | Lewis et al. |
| 8,493,187 B2 | 7/2013 | Rowland |
| 8,500,660 B2 | 8/2013 | Buchwald et al. |
| 8,521,282 B2 | 8/2013 | Czygan et al. |
| 8,527,046 B2 | 9/2013 | Connelly et al. |
| 8,556,929 B2 | 10/2013 | Harper et al. |
| 8,570,186 B2 | 10/2013 | Nagy |
| 8,600,517 B2 | 12/2013 | Forsell |
| 8,613,705 B2 | 12/2013 | Scheurer |
| 8,632,469 B2 | 1/2014 | Kassab |
| 8,644,941 B2 | 2/2014 | Rooney et al. |
| 8,665,086 B2 | 3/2014 | Miner |
| 8,669,770 B2 | 3/2014 | Cros |
| 8,696,584 B2 | 4/2014 | Kassab |
| 8,702,613 B2 | 4/2014 | Kassab |
| 8,706,208 B2 | 4/2014 | Chiao et al. |
| 8,706,209 B2 | 4/2014 | Kassab |
| 8,728,012 B2 | 5/2014 | Braido |
| 8,784,338 B2 | 7/2014 | Wallace |
| 8,798,712 B2 | 8/2014 | Gopinathan et al. |
| 8,814,798 B2 | 8/2014 | Corbucci et al. |
| 8,818,507 B2 | 8/2014 | Liu et al. |
| 8,825,151 B2 | 9/2014 | Gopinathan et al. |
| 8,827,929 B2 | 9/2014 | O'Dea |
| 8,855,783 B2 | 10/2014 | Dagan et al. |
| 8,864,666 B2 | 10/2014 | Kassem |
| 8,870,787 B2 | 10/2014 | Yadav |
| 8,874,203 B2 | 10/2014 | Kassab et al. |
| 8,886,301 B2 | 11/2014 | Kassab |
| 8,894,582 B2 | 11/2014 | Nunez |
| 8,896,324 B2 | 11/2014 | Kroh |
| 8,909,351 B2 | 12/2014 | Dinsmoor et al. |
| 8,918,169 B2 | 12/2014 | Kassab et al. |
| 8,938,292 B2 | 1/2015 | Hettrick et al. |
| 8,951,219 B2 | 2/2015 | Gerber et al. |
| 9,049,995 B2 | 6/2015 | Blomqvist et al. |
| 9,060,798 B2 | 6/2015 | Harper et al. |
| 9,061,099 B2 | 6/2015 | Gerber et al. |
| 9,066,672 B2 | 6/2015 | Kassab et al. |
| 9,198,706 B2 | 12/2015 | Kassab et al. |
| 9,265,428 B2 | 2/2016 | O'Brien et al. |
| 9,289,132 B2 | 3/2016 | Ghaffari et al. |
| 9,289,229 B2 | 3/2016 | Kassab |
| 9,305,456 B2 | 4/2016 | Rowland |
| 9,314,169 B2 | 4/2016 | Kassab |
| 9,326,728 B2 | 5/2016 | Demir et al. |
| 9,332,914 B2 | 5/2016 | Langston |
| 9,332,916 B2 | 5/2016 | Kassab |
| 9,333,365 B2 | 5/2016 | Zhao |
| 9,351,661 B2 | 5/2016 | Kassab |
| 9,393,416 B2 | 7/2016 | Rooney et al. |
| 9,445,743 B2 | 9/2016 | Kassab |
| 9,489,831 B2 | 11/2016 | Nagy et al. |
| 9,526,637 B2 | 12/2016 | Dagan et al. |
| 9,603,533 B2 | 3/2017 | Lading et al. |
| 9,662,066 B2 | 5/2017 | Ledet et al. |
| 9,675,257 B2 | 6/2017 | Kassab |
| 9,675,315 B2 | 6/2017 | Song et al. |
| 9,721,463 B2 | 8/2017 | Rowland |
| 9,814,395 B2 | 11/2017 | Stahmann et al. |
| 9,878,080 B2 | 1/2018 | Kaiser et al. |
| 9,901,722 B2 | 2/2018 | Nitzan et al. |
| 9,996,712 B2 | 6/2018 | Sundaram et al. |
| 10,080,528 B2 | 9/2018 | BeBusschere et al. |
| 10,092,247 B2 | 10/2018 | Taylor |
| 10,105,103 B2 | 10/2018 | Goldshtein et al. |
| 10,194,808 B1 | 2/2019 | Thompson |
| 10,195,441 B2 | 2/2019 | Kaiser |
| 10,201,285 B2 | 2/2019 | Sawanoi |
| 10,210,956 B2 | 2/2019 | Lavi |
| 10,213,129 B2 | 2/2019 | Kassab |
| 10,219,704 B2 | 3/2019 | Lavi |
| 10,219,720 B2 | 3/2019 | Kassab |
| 10,219,724 B2 | 3/2019 | Stern |
| 10,226,203 B2 | 3/2019 | Stigall |
| 10,226,218 B2 | 3/2019 | Rowland |
| 10,231,659 B2 | 3/2019 | Vanslyke |
| 10,231,701 B2 | 3/2019 | Ryan |
| 10,236,084 B2 | 3/2019 | Grady |
| 10,238,311 B2 | 3/2019 | Kassab |
| 10,238,322 B2 | 3/2019 | Vanslyke |
| 10,238,323 B2 | 3/2019 | Vanslyke |
| 10,238,324 B2 | 3/2019 | Vanslyke |
| 10,240,994 B1 | 3/2019 | Xu |
| 10,265,024 B2 | 4/2019 | Lee |
| 10,271,797 B2 | 4/2019 | Zhang |
| 2002/0120205 A1 | 8/2002 | Ferek-Petric |
| 2003/0037591 A1 | 2/2003 | Ashton et al. |
| 2003/0060139 A1 | 3/2003 | Richter |
| 2003/0158584 A1 | 8/2003 | Cates et al. |
| 2004/0106871 A1 | 6/2004 | Hunyor et al. |
| 2004/0116992 A1 | 6/2004 | Wardle et al. |
| 2004/0133092 A1 | 7/2004 | Kain |
| 2004/0167596 A1 | 8/2004 | Richter |
| 2004/0215235 A1 | 10/2004 | Jackson et al. |
| 2005/0148903 A1 | 7/2005 | Diamantopoulos |
| 2005/0154321 A1 | 7/2005 | Wolinsky |
| 2006/0056161 A1 | 3/2006 | Shin |
| 2006/0106321 A1 | 5/2006 | Lewinsky et al. |
| 2006/0122522 A1 | 6/2006 | Chavan et al. |
| 2006/0149166 A1 | 7/2006 | Zvuloni |
| 2006/0174712 A1 | 8/2006 | O'Brien |
| 2006/0177956 A1 | 8/2006 | O'Brien |
| 2006/0178695 A1 | 8/2006 | Decant |
| 2006/0253160 A1 | 11/2006 | Benditt et al. |
| 2006/0271119 A1 | 11/2006 | Ni et al. |
| 2006/0287602 A1 | 12/2006 | Obrien et al. |
| 2006/0287700 A1 | 12/2006 | White |
| 2007/0088214 A1 | 4/2007 | Shuros et al. |
| 2007/0129637 A1 | 6/2007 | Wolinsky et al. |
| 2007/0158769 A1 | 7/2007 | You |
| 2007/0199385 A1 | 8/2007 | O'Brien |
| 2007/0274565 A1 | 11/2007 | Penner |
| 2007/0282210 A1 | 12/2007 | Stern |
| 2007/0292090 A1 | 12/2007 | Alphonse et al. |
| 2008/0015569 A1 | 1/2008 | Saadat |
| 2008/0033527 A1 | 2/2008 | Nunez et al. |
| 2008/0077016 A1* | 3/2008 | Sparks ............... A61B 5/0031 |
| | | 600/459 |
| 2008/0097227 A1 | 4/2008 | Zdeblick et al. |
| 2008/0177186 A1 | 7/2008 | Slater et al. |
| 2008/0294041 A1 | 11/2008 | Kassab |
| 2009/0007679 A1 | 1/2009 | Nunez |
| 2009/0009332 A1 | 1/2009 | Nunez |
| 2009/0011117 A1 | 1/2009 | Nunez |
| 2009/0024042 A1 | 1/2009 | Nunez |
| 2009/0030291 A1 | 1/2009 | O'Brien |
| 2009/0062684 A1 | 3/2009 | Gregersen et al. |
| 2009/0105799 A1 | 4/2009 | Hekmat et al. |
| 2009/0149766 A1 | 6/2009 | Shuros et al. |
| 2009/0177225 A1 | 7/2009 | Nunez et al. |
| 2009/0189741 A1 | 7/2009 | Rowland |
| 2009/0198293 A1* | 8/2009 | Cauller ............... A61B 5/0031 |
| | | 607/2 |
| 2009/0270729 A1 | 10/2009 | Corbucci |
| 2009/0299427 A1 | 12/2009 | Liu et al. |
| 2010/0056922 A1 | 3/2010 | Florent |
| 2010/0063375 A1 | 3/2010 | Kassab et al. |
| 2010/0076398 A1 | 3/2010 | Scheurer et al. |
| 2010/0094328 A1 | 4/2010 | Odea et al. |
| 2010/0113939 A1 | 5/2010 | Mashimo et al. |

(56) References Cited

U.S. PATENT DOCUMENTS

| | | |
|---|---|---|
| 2010/0121398 A1 | 5/2010 | Bjorling et al. |
| 2010/0222786 A1 | 9/2010 | Kassab |
| 2010/0262206 A1 | 10/2010 | Zdeblick et al. |
| 2010/0324432 A1 | 12/2010 | Bjorling et al. |
| 2011/0105863 A1 | 5/2011 | Kroh |
| 2011/0144967 A1 | 6/2011 | Adirovich |
| 2011/0160844 A1 | 6/2011 | Haselby |
| 2011/0178383 A1 | 7/2011 | Kassab |
| 2011/0184301 A1 | 7/2011 | Holmstrom et al. |
| 2011/0201990 A1 | 8/2011 | Franano |
| 2011/0306867 A1 | 12/2011 | Gopinathan et al. |
| 2012/0016207 A1 | 1/2012 | Allen |
| 2012/0029598 A1 | 2/2012 | Zhao |
| 2012/0136385 A1 | 5/2012 | Cully |
| 2012/0203090 A1 | 8/2012 | Min |
| 2012/0203113 A1 | 8/2012 | Skerl et al. |
| 2012/0291788 A1 | 11/2012 | Griswold et al. |
| 2012/0296222 A1 | 11/2012 | Griswold et al. |
| 2013/0030295 A1 | 1/2013 | Huennekens et al. |
| 2013/0041244 A1 | 2/2013 | Woias et al. |
| 2013/0041251 A1 | 2/2013 | Bailey et al. |
| 2013/0041269 A1 | 2/2013 | Stahmann et al. |
| 2013/0073025 A1 | 3/2013 | Kassab |
| 2013/0096409 A1 | 4/2013 | Hiltner et al. |
| 2013/0178750 A1 | 7/2013 | Sheehan et al. |
| 2013/0178751 A1 | 7/2013 | Min |
| 2013/0222153 A1 | 8/2013 | Rowland et al. |
| 2013/0245469 A1 | 9/2013 | Yadav |
| 2013/0261655 A1 | 10/2013 | Drasler et al. |
| 2013/0274705 A1 | 10/2013 | Burnes et al. |
| 2013/0296721 A1 | 11/2013 | Yadav et al. |
| 2013/0303914 A1 | 11/2013 | Hiltner et al. |
| 2013/0303915 A1 | 11/2013 | Barnard et al. |
| 2013/0310820 A1 | 11/2013 | Fernandez et al. |
| 2013/0317359 A1 | 11/2013 | Wilson et al. |
| 2013/0324866 A1 | 12/2013 | Gladshtein |
| 2013/0331678 A1 | 12/2013 | Lading et al. |
| 2013/0338468 A1 | 12/2013 | Kassab |
| 2014/0028467 A1 | 1/2014 | Nagy |
| 2014/0051965 A1 | 2/2014 | Zdeblick et al. |
| 2014/0066738 A1 | 3/2014 | Kassab |
| 2014/0084943 A1 | 3/2014 | Kroh |
| 2014/0088994 A1 | 3/2014 | Kroh |
| 2014/0094697 A1 | 4/2014 | Petroff et al. |
| 2014/0107768 A1 | 4/2014 | Venkatasubramanian |
| 2014/0155710 A1 | 6/2014 | Rowland |
| 2014/0155768 A1 | 6/2014 | Orion et al. |
| 2014/0155769 A1 | 6/2014 | White |
| 2014/0200428 A1 | 7/2014 | Kassab |
| 2014/0236011 A1 | 8/2014 | Fan et al. |
| 2014/0243640 A1 | 8/2014 | O'Dea |
| 2014/0275861 A1 | 9/2014 | Kroh |
| 2014/0276011 A1 | 9/2014 | Schmitt et al. |
| 2014/0276110 A1 | 9/2014 | Hoseit |
| 2014/0276121 A1 | 9/2014 | Kassab |
| 2014/0276191 A1 | 9/2014 | Kassab |
| 2014/0288085 A1 | 9/2014 | Yadav |
| 2014/0288459 A1 | 9/2014 | Yadav |
| 2014/0306807 A1 | 10/2014 | Rowland |
| 2014/0330143 A1 | 11/2014 | Kroh et al. |
| 2014/0350348 A1 | 11/2014 | Tee et al. |
| 2015/0031966 A1 | 1/2015 | Ward et al. |
| 2015/0045649 A1 | 2/2015 | O'Dea et al. |
| 2015/0051467 A1 | 2/2015 | Corbucci et al. |
| 2015/0065835 A1 | 3/2015 | Kassab |
| 2015/0065897 A1 | 3/2015 | Bomzin et al. |
| 2015/0088100 A1 | 3/2015 | Oborn |
| 2015/0133796 A1 | 5/2015 | Yadav |
| 2015/0141863 A1 | 5/2015 | Kassab et al. |
| 2015/0157268 A1 | 6/2015 | Winshtein et al. |
| 2015/0208929 A1 | 7/2015 | Rowland |
| 2015/0216425 A1 | 8/2015 | Gladshtein et al. |
| 2015/0223702 A1 | 8/2015 | Vanney et al. |
| 2015/0238121 A1 | 8/2015 | Tu et al. |
| 2015/0257732 A1 | 9/2015 | Ryan |
| 2015/0282720 A1 | 10/2015 | Goldshtein et al. |
| 2015/0282875 A1 | 10/2015 | Harper et al. |
| 2015/0297110 A1 | 10/2015 | Kassab |
| 2015/0297111 A1 | 10/2015 | Kassab |
| 2015/0297112 A1 | 10/2015 | Kassab et al. |
| 2015/0297113 A1 | 10/2015 | Kassab |
| 2015/0297818 A1 | 10/2015 | Matsubara et al. |
| 2015/0305808 A1 | 10/2015 | Ku et al. |
| 2015/0313479 A1 | 11/2015 | Stigall et al. |
| 2015/0327786 A1 | 11/2015 | Lading et al. |
| 2016/0000403 A1 | 1/2016 | Vilkomerson |
| 2016/0022216 A1 | 1/2016 | Goldshtein et al. |
| 2016/0029956 A1 | 2/2016 | Rowland |
| 2016/0029995 A1 | 2/2016 | Navratil et al. |
| 2016/0081657 A1 | 3/2016 | Rice |
| 2016/0095535 A1 | 4/2016 | Hettrick et al. |
| 2016/0135787 A1 | 5/2016 | Anderson et al. |
| 2016/0166232 A1 | 6/2016 | Merritt |
| 2016/0198981 A1 | 7/2016 | Demir et al. |
| 2016/0210846 A1 | 7/2016 | Rowland et al. |
| 2016/0324443 A1 | 11/2016 | Rowland et al. |
| 2016/0345930 A1 | 12/2016 | Mizukami |
| 2017/0055048 A1 | 2/2017 | Nagy et al. |
| 2017/0055909 A1 | 3/2017 | Schibli et al. |
| 2017/0065824 A1 | 3/2017 | Dagan et al. |
| 2017/0071501 A1 | 3/2017 | Kassab |
| 2017/0238817 A1 | 8/2017 | Lading |
| 2017/0360312 A1 | 12/2017 | Joseph |
| 2018/0064931 A1 | 3/2018 | Clements |
| 2018/0177486 A1 | 6/2018 | Gifford et al. |
| 2018/0220992 A1 | 8/2018 | Gifford et al. |
| 2018/0228951 A1 | 8/2018 | Schwammenthal et al. |
| 2018/0247095 A1 | 8/2018 | Sundaram et al. |
| 2018/0268941 A1 | 9/2018 | Lavi et al. |
| 2018/0269931 A1 | 9/2018 | Hershko et al. |
| 2018/0289488 A1 | 10/2018 | Orth et al. |
| 2018/0289536 A1 | 10/2018 | Burnett |
| 2018/0293409 A1 | 10/2018 | Sundaram et al. |
| 2019/0029639 A1 | 1/2019 | Gifford et al. |
| 2019/0046047 A1 | 2/2019 | Haase |
| 2019/0053720 A1 | 2/2019 | Sawado |
| 2019/0053767 A1 | 2/2019 | Yamada |
| 2019/0069784 A1 | 3/2019 | Mukkamala |
| 2019/0069842 A1 | 3/2019 | Rothberg |
| 2019/0069851 A1 | 3/2019 | Sharma |
| 2019/0070348 A1 | 3/2019 | Frost |
| 2019/0076033 A1 | 3/2019 | Sweeney |
| 2019/0082978 A1 | 3/2019 | Van der Horst |
| 2019/0083030 A1 | 3/2019 | Thakur |
| 2019/0090760 A1 | 3/2019 | Kinast |
| 2019/0090763 A1 | 3/2019 | Woerlee |
| 2019/0090856 A1 | 3/2019 | Van der Horst |
| 2019/0099087 A1 | 4/2019 | Cros |
| 2019/0099088 A1 | 4/2019 | Whinnett |
| 2019/0110696 A1 | 4/2019 | Benkowski |
| 2019/0167188 A1 | 6/2019 | Gifford et al. |

FOREIGN PATENT DOCUMENTS

| | | |
|---|---|---|
| EP | 1162914 A1 | 12/2001 |
| EP | 1311210 A2 | 5/2003 |
| EP | 0904009 B1 | 9/2003 |
| EP | 1545303 A2 | 6/2005 |
| EP | 1677852 A2 | 7/2006 |
| EP | 1847217 A2 | 10/2007 |
| EP | 1851524 A2 | 11/2007 |
| EP | 1851791 A2 | 11/2007 |
| EP | 1868496 A2 | 12/2007 |
| EP | 1871224 A2 | 1/2008 |
| EP | 1893080 A2 | 3/2008 |
| EP | 1893081 A2 | 3/2008 |
| EP | 1893085 A2 | 3/2008 |
| EP | 2091426 A2 | 6/2008 |
| EP | 1948007 | 7/2008 |
| EP | 1993438 A1 | 11/2008 |
| EP | 2012658 A2 | 1/2009 |
| EP | 2046242 A2 | 4/2009 |
| EP | 2117423 A2 | 11/2009 |
| EP | 2197344 A1 | 6/2010 |

(56) References Cited

FOREIGN PATENT DOCUMENTS

| | | |
|---|---|---|
| EP | 2265164 A1 | 12/2010 |
| EP | 2021757 B1 | 4/2011 |
| EP | 2391263 A2 | 12/2011 |
| EP | 1921983 B1 | 1/2012 |
| EP | 2060014 B1 | 1/2012 |
| EP | 1902529 B1 | 6/2012 |
| EP | 1876945 B1 | 12/2012 |
| EP | 2330968 B1 | 4/2013 |
| EP | 2601633 A2 | 6/2013 |
| EP | 2449960 B1 | 10/2013 |
| EP | 2725969 A1 | 5/2014 |
| EP | 1993436 B1 | 6/2014 |
| EP | 3027109 A1 | 2/2015 |
| EP | 2076170 B1 | 4/2015 |
| EP | 2895059 A1 | 7/2015 |
| EP | 2898470 A1 | 7/2015 |
| EP | 2922465 A1 | 9/2015 |
| EP | 2317912 B1 | 11/2015 |
| EP | 1817593 B1 | 12/2015 |
| EP | 2967432 A2 | 1/2016 |
| EP | 2268218 B1 | 2/2016 |
| EP | 2456502 B1 | 4/2016 |
| EP | 2702578 B1 | 8/2016 |
| EP | 3057075 A1 | 8/2016 |
| EP | 2417590 B1 | 5/2017 |
| EP | 3359021 A1 | 8/2018 |
| EP | 3435847 A1 | 2/2019 |
| EP | 3435862 A1 | 2/2019 |
| EP | 3437000 A1 | 2/2019 |
| EP | 3448330 A1 | 3/2019 |
| EP | 3448487 A2 | 3/2019 |
| EP | 3457911 A1 | 3/2019 |
| EP | 3457924 A1 | 3/2019 |
| EP | 3457928 A1 | 3/2019 |
| EP | 3463082 A1 | 4/2019 |
| EP | 3468462 A1 | 4/2019 |
| JP | 2011234884 A | 11/2011 |
| WO | 0399059 A1 | 5/1989 |
| WO | 0538885 A1 | 4/1993 |
| WO | 1997042871 A1 | 11/1997 |
| WO | 1998029030 A1 | 12/1997 |
| WO | 1998035611 A1 | 8/1998 |
| WO | 2000055579 A2 | 9/2000 |
| WO | 2000056210 A1 | 9/2000 |
| WO | 2001012092 A1 | 2/2001 |
| WO | 2001013792 A1 | 3/2001 |
| WO | 2002015823 A2 | 2/2002 |
| WO | 2002076289 A2 | 10/2002 |
| WO | 2003061467 A1 | 7/2003 |
| WO | 2003061504 A1 | 7/2003 |
| WO | 2003092495 A1 | 11/2003 |
| WO | 2004014456 A2 | 2/2004 |
| WO | 2004073796 A1 | 9/2004 |
| WO | 2006049796 A2 | 5/2006 |
| WO | 2006086113 A2 | 8/2006 |
| WO | 2006086114 A2 | 8/2006 |
| WO | 2005027998 A2 | 9/2006 |
| WO | 2006094273 A2 | 9/2006 |
| WO | 2006096582 A1 | 9/2006 |
| WO | 2006102905 A1 | 10/2006 |
| WO | 2006110798 A2 | 10/2006 |
| WO | 2007002185 A2 | 1/2007 |
| WO | 2007002224 A2 | 1/2007 |
| WO | 2007002225 A2 | 1/2007 |
| WO | 2007008493 A1 | 1/2007 |
| WO | 2007028035 A2 | 3/2007 |
| WO | 2007035332 A1 | 3/2007 |
| WO | 2007047571 A2 | 4/2007 |
| WO | 2007047794 A2 | 4/2007 |
| WO | 2007061841 A2 | 5/2007 |
| WO | 2007106490 A2 | 9/2007 |
| WO | 2007106533 A1 | 9/2007 |
| WO | 2007130628 A2 | 11/2007 |
| WO | 2008031011 A1 | 3/2008 |
| WO | 2008031095 A1 | 3/2008 |
| WO | 2008051907 A1 | 5/2008 |
| WO | 2008066569 A2 | 6/2008 |
| WO | 2009006602 A1 | 1/2009 |
| WO | 2009006608 A1 | 1/2009 |
| WO | 2009006610 A1 | 1/2009 |
| WO | 2009006615 A1 | 1/2009 |
| WO | 2009025648 A1 | 2/2009 |
| WO | 2009039174 A1 | 3/2009 |
| WO | 2009111255 A1 | 9/2009 |
| WO | 2009131879 A1 | 10/2009 |
| WO | 2011060359 A2 | 11/2009 |
| WO | 2009146089 A2 | 12/2009 |
| WO | 2009146090 A1 | 12/2009 |
| WO | 2010011612 A1 | 1/2010 |
| WO | 2010088279 A2 | 8/2010 |
| WO | 2010117597 A1 | 10/2010 |
| WO | 20100117356 A1 | 10/2010 |
| WO | 2011011104 A1 | 1/2011 |
| WO | 2012015954 A1 | 2/2012 |
| WO | 2012015955 A1 | 2/2012 |
| WO | 2012019191 A2 | 2/2012 |
| WO | 2012090206 A2 | 7/2012 |
| WO | 2012140147 A3 | 10/2012 |
| WO | 2012145187 A1 | 10/2012 |
| WO | 2012149008 A2 | 11/2012 |
| WO | 2013003754 A1 | 1/2013 |
| WO | 2013142387 A1 | 9/2013 |
| WO | 2014006471 A2 | 1/2014 |
| WO | 2004014456 A2 | 2/2014 |
| WO | 2014047528 A1 | 3/2014 |
| WO | 2014054045 A1 | 4/2014 |
| WO | 2014070316 A1 | 5/2014 |
| WO | 2014076620 A2 | 5/2014 |
| WO | 2014081958 A1 | 5/2014 |
| WO | 2014145531 A1 | 9/2014 |
| WO | 2014145712 A1 | 9/2014 |
| WO | 2014162181 A2 | 10/2014 |
| WO | 2014170771 A1 | 10/2014 |
| WO | 2014179739 A1 | 11/2014 |
| WO | 2014197101 A1 | 12/2014 |
| WO | 2015074018 A1 | 5/2015 |
| WO | 2015109028 A1 | 7/2015 |
| WO | 2016011309 A2 | 1/2016 |
| WO | 2016025430 A1 | 2/2016 |
| WO | 2016131020 A1 | 8/2016 |
| WO | 2016178196 A2 | 11/2016 |
| WO | 2016178197 A1 | 11/2016 |
| WO | 2017024051 A1 | 2/2017 |
| WO | 2017143198 A1 | 8/2017 |
| WO | 2017198867 A1 | 11/2017 |
| WO | 2017222964 A1 | 12/2017 |
| WO | 2018013725 A1 | 1/2018 |
| WO | 2018031714 A1 | 2/2018 |
| WO | 2018081314 A1 | 5/2018 |
| WO | 2018102435 A1 | 6/2018 |
| WO | 2018150314 A1 | 8/2018 |
| WO | 2018156930 A1 | 8/2018 |
| WO | 2018187582 A1 | 10/2018 |
| WO | 2018220143 A1 | 12/2018 |
| WO | 2018220146 A1 | 12/2018 |
| WO | 2019050831 A1 | 3/2019 |
| WO | 2019051007 A1 | 3/2019 |
| WO | 2019051108 A1 | 3/2019 |
| WO | 2019051007 A8 | 4/2019 |
| WO | 2019063521 A1 | 4/2019 |
| WO | 2019079364 A1 | 4/2019 |

OTHER PUBLICATIONS

Cannesson et al., "Respiratory Variations in Pulse Oximetry Plethysmographic Waveform Amplitude to Predict Fluid Responsiveness in the Operating Room," Anesthesiology 2007; 106:1105-11.

Abraham et al., "The Role of Implantable Hemodynamic Monitors to Manage Heart Failure," Heart Failure Clin 11 (2015)183-189.

Tallaj et al., "Implantable Hemodynamic Monitors," Cardiol Clin 29 (2011) 289-299.

(56) References Cited

OTHER PUBLICATIONS

Tang et al., "Measuring impedance in congestive heart failure: Current options and clinical applications," American Heart Journal 157 (3) 402-411.
Merchant et al., "Implantable Sensors for Heart Failure," Circulation: Arrhythmia and Electrophysiology. 2010; 3:657-667.
Unadkat, Jignesh V., et al. "The Development of a Wireless Implantable Blood Flow Monitor," Ideas and Innovations, American Society of Plastic Surgeons, 136:199 (2015).
Steinhouse, David et al., "Implant Experience with an Implantable Hemodynamic Monitor for the Management of Symptomatic Heart Failure," PACE (Aug. 2005) vol. 28, pp. 747-753.
Braunschweig, Frieder et al. "Dynamic changes in right ventricular pressures during haemodialysis recorded with an implantable haemodynamic monitor," Nephrol Dial Transplant (2006) 21:176-183.
Karamanoglu, Mustafa et al., "Estimation of cardiac output in patients with congestive heart failure by analysis of right ventricular pressure waveforms," BioMedical Engineering OnLine 2011, 10:36.
Spiliopoulos, Sotirios et la., "Beneficial aspects of real time flow measurements for the management of acute right ventricular heart failure following continuous flow ventricular assist device implantation," Journal of Cardiothoracic Surgery (2012) 7:119.
Sharma, Arjun D. et al., "Right Ventricular Pressure During Ventricular Arrhythmias in Humans: Potential Implications for Implantable Antitachycardia Devices," JACC vol. 15, No. 3, Mar. 1, 1990, pp. 648-655.
Kjellstrom, Barbo et al., "Changes in Right Ventricular Pressures Between Hemodialysis Sessions Recorded by an Implantable Hemodynamic Monitor," The American Journal of Cardiology, 2009, 103:119-123.
Zile, Michael R. et al., "Transition From Chronic Compensated to Acute Decompensated Heart Failure," Circulation, American Heart Association (2008) 118:1433-1441.
Plicchi, G. et al., "Pea I and Pea II Based Implantable Haemodynamic Monitor Pre Clinical Studies in Sheep," Europace (2002) 4, 49-54.
Vanderheyden, Marc et al., "Continuous Monitoring of Intrathoracic Impedance and Right Ventricular Pressures in Patients With Heart Failure," Circulation Heart Failure (2010) 3:370-377.
Jacobs, Donald L. et al., "Bedside vena cava filter placement with intravascular ultrasound: A simple, accurate, single venous access method," Technical Note, Journal of Vascular Surgery, vol. 46, No. 6, pp. 1284-1286, Dec. 2007.
Muller, Laurent et al., "Respiratory variations of inferior vena cava diameter to predict fluid responsiveness in spontaneously breathing patients with acute circulatory failure: need for a cautious use," Critical Care 2012, 16:R188.
Blehar, David J. et al., "Identification of congestive heart failure via respiratory variation of inferior vena cava diameter." American Journal of Emergency Medicine (2009) 27, 71-75.
Miller, Joseph B., et al., "Inferior vena cava assessment in the bedside diagnosis of acute heart failure," American Journal of Emergency Medicine (2012) 30, 778-783.
Corl, Keith et al., "Bedside sonographic measurement of the inferior vena cava caval index is a poor predictor of fluid responsiveness in emergency department patients," Emergency Medicine Australasia (2012) 24, 534-539.
Feissel, et al. "The respiratory variation in inferior vena cava diameter as a guide to fluid therapy," Intensive Care Med (2004) 30: 1834-1837.
Nakao, Shoichiro et al., "Effects of Positional Changes on Inferior Vena Caval Size and Dynamics and Correlations with Right-Sided Cardiac Pressure," American Journal of Cardiology (1987; 59:125-132).
Saha, Narayan M., et al., "Outpatient Use of Focused Cardiac Ultrasound to Assess the Inferior Vena Cava in Patients With Heart Failure," American Journal of Cardiology (2015).
Ishizaki, et al. "Measurement of inferior vena cava diameter for evaluation of venous return in subjects on day 10 of a bed-rest experiment," J Appl Physical 96: 2179-2186, 2004.
Carbone et al. "Inferior Vena Cava Parameters Predict Re-admission in Ischaemic Heart Failure", European Journal of Clinical Investigations, 2014, 44(4): 341-349.
Bertram, C.D. et al., "Cross-sectional area measurement in collapsed tubes using the transformer principle", Med. & . Biol, Eng. & Comput, 1989, 27, 357-364.
Moreno, Augusto et al., "Mechanics of Distension of Dog Veins and Other Very Thin-Walled Tubular Structures", Circulation Research, vol. XXVII, Dec. 1970, pp. 1069-1080.
Tafur, Emilio et al., "Simultaneous Pressure, Flow and Diameter of the Vena Cava with Fright and Exercise", Circulation Research, vol. XIX, Jul. 1966., pp. 42-50.
Guntheroth, Warren G., et al., "Effect of Respiration on Venous Return and Stroke Volume in Cardiac Tamponade", circulation Research, vol. XX, Apr. 1967, pp. 381-390.
Bartels, Lambertus et al., "Improved Lumen Visualization in Metallic Vascular Implants by Reducing RF Artifacts", Magnetic Resonance in Medicine 47:171-180 (2002).
Guntheroth, Warren G., "in Vivo Measurement of Dimensions of Veins with Implications Regarding Control of Venous Return", IEEE Transactions on Bio-Medical Engineering, Oct. 1969; pp. 247-253.
Kivelitz, Dietmar et al., "A Vascular Stent as an Active Component for Locally Enhanced Magnetic Resonance Imaging", Investigative Radiology, vol. 38, No. 3, 147-152 (2003).
Reddy, Reddy R.V., et al., "A Catheter-Tip Probe for Dynamic Cross-Section Area Measurement", pp. 149-158. (1973).
Stegall, H. Fred, "Survey of Dimension Transducers", Chronically Implanted Cardiovascular Instrumentation, pp. 107-115 (1973).
D. H. Bergel, "The Measurement of Lengths and Dimensions", Cardiovascular Fluid Dynamics, vol. 1. pp. 91-114 (1972).
Baan, Jan et al., "Dynamic Local Distensibility of Living Arteries and its relation to Wave Transmission", Biophysical Journal, vol. 14, (1974); pp. 343-362.
International Search Report and Written Opinion in connection with PCT/US2016/017902, dated Jul. 27, 2016.
Reems, Miryam et al., Central Venous Pressure: Principles, Measurement, and Interpretation, Vetlearn.com, Jan. 2012, Compendium: Continuing Education for Veterinarians, pp. E1-E10.
Yamauchi, Hideko et al., "Correlation Between Blood Volume and Pulmonary Artery Catheter Measurements", Department of Surgery and Surgical Critical Care, University of Hawaii, 2005.
Abraham, William T. et al., "Wireless pulmonary artery haemodynamic monitoring in chronic heart failure: a randomised controlled trial"; www.thelancet.com, vol. 377, Feb. 19, 2011, pp. 658-666.
Guiotto, Giovanna et al., "Inferior vena cava collapsibility to guide fluid removal in slow continuous ultrafiltration: a pilot study", Intensive Care Med (2010) 36:696-696.
Martens, Pieter et al., "Current Approach to Decongestive Therapy in Acute Heart Failure", Curr Heart Fail Rep (2015) 12:367-378.
Dupont, Matthias et a., "Impact of Systemic Venous Congestion in Heart Failure", Curr Heart Fail Rep (2011) 8:233-241.
Marik, Paul E. et al., "Hemodynamic parameters to guide fluid therapy", Annals of Intensive Care 2011, 1:1; http://www.annalsofintensivecare.com/content/1/1/1.
Silverberg, Donald et al., "The association between congestive heart failure and chronic renal disease", Curr Opin Nephrol Hypertens 13: 163-170, 2004.
International Search Report and Written Opinion dated Mar. 27, 2018, in connection with PCT/US2017/063749.
International Search Report and Written Opinion dated Aug. 29, 2018, in connection with PCT/EP2018/064386.
International Search Report and Written Opinion dated Aug. 21, 2018, in connection with PCT/EP2018/064383.
International Search Report and Written Opinion dated Oct. 19, 2017, in connection with PCT/US2017/046204.
Brennan, J.M., "Handcarried Ultrasound Measurement of the Inferior Vena Cava for Assessment of Intravascular Volume Status in the Outpatient Hemodialysis Clinic"; Clinical Journal of the American Society of Nephrology; pp. 749-753; Jan. 23, 2006.
International Search Report and Written Opinion dated Oct. 20, 2016, in connection with PCT/US2016/045385 filed Aug. 3, 2016.

(56) References Cited

OTHER PUBLICATIONS

International Search Report and Written Opinion dated Feb. 27, 2020, in connection with PCT/IB2019/060669 filed Dec. 11, 2019.
International Search Report and Written Opinion dated Nov. 4, 2019, in connection with PCT/US2019/034657, filed May 30, 2019.
International Search Report and Written Opinion dated Mar. 3, 2020, in connection with PCT/US2019/066589 filed Dec. 16, 2019.
Extended European Search Report dated Jul. 3, 2020, in connection with EP20163433.4.

* cited by examiner

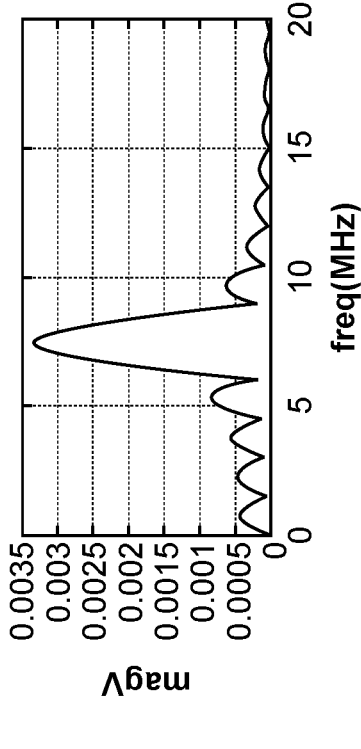
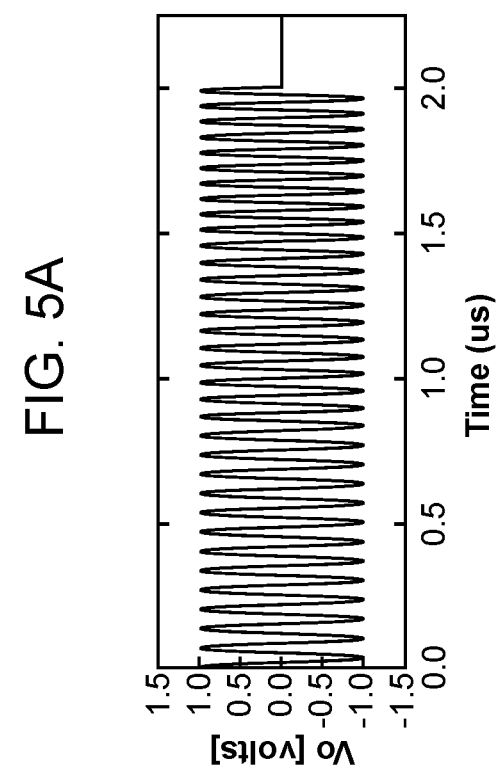
FIG. 5A
FIG. 5B
FIG. 6A
FIG. 6B

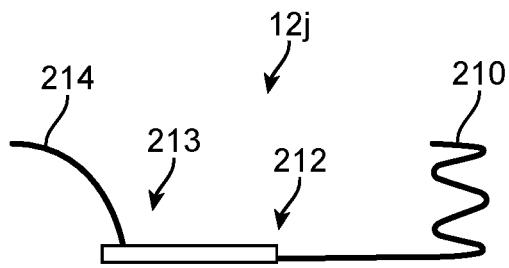
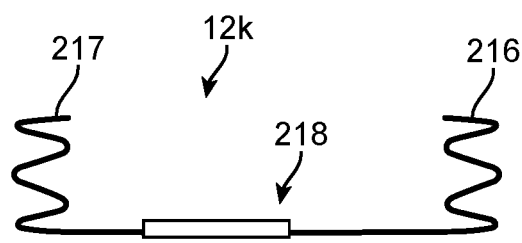
FIG. 16A    FIG. 16B
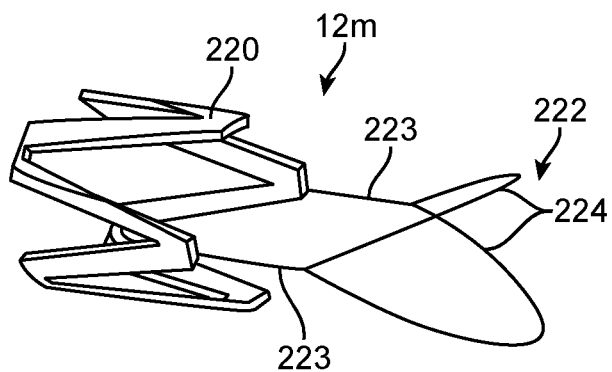
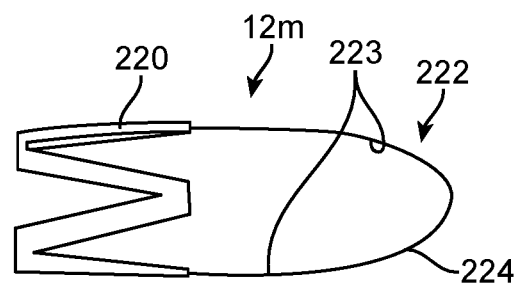
FIG. 17A    FIG. 17B

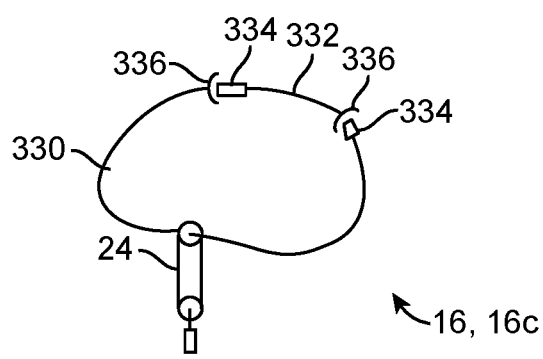
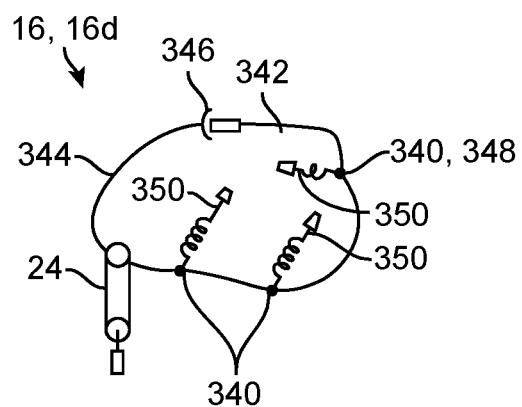
FIG. 27A
FIG. 27B
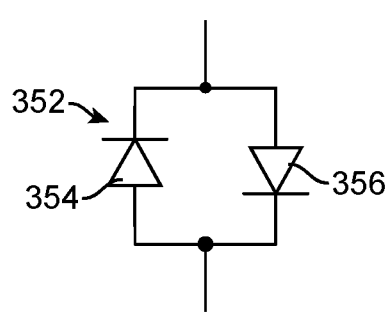
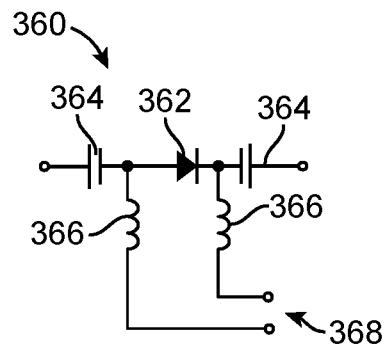
FIG. 28A
FIG. 28B

WIRELESS VASCULAR MONITORING IMPLANTS

RELATED APPLICATION DATA

This application is a continuation of International Patent Application No. PCT/US17/63749, filed Nov. 29, 2017, entitled "Wireless Resonant Circuit and Variable Inductance Vascular Implants for Monitoring Patient Vasculature and Fluid Status and Systems and Methods Employing Same"; which application claims the benefit of priority of U.S. Provisional Patent Application Ser. No. 62/534,329, filed on Jul. 19, 2017; International Patent Application No. PCT/US17/46204, filed Aug. 10, 2017; and U.S. Provisional Patent Application Ser. No. 62/427,631, filed Nov. 29, 2016. Each application is incorporated by reference herein in its entirety.

FIELD OF THE DISCLOSURE

The present invention generally relates to the field of vascular monitoring. In particular, the present invention is directed to wireless vascular monitoring implants, systems, methods, and software. More specifically, embodiments disclosed herein relate to fluid volume sensing in the inferior vena cava (IVC) using wireless, remotely or automatically actuatable implants for monitoring or management of blood volume.

BACKGROUND

Others have attempted to develop vascular monitoring devices and techniques, including those directed at monitoring vessel arterial or venous pressure or vessel lumen dimensions. However, many such existing systems are catheter based (not wireless) and thus can only be utilized in a clinical setting for limited periods of times, and may carry risks associated with extended catheterization. For a wireless solution, the complexity of deployment, fixation and the interrelationship of those factors with detection and communication have led to, at best, inconsistent results with such previously developed devices and techniques.

Existing wireless systems focus on pressure measurements, which in the IVC can be less responsive to patient fluid state than IVC dimension measurements. However, systems designed to measure vessel dimensions also have a number of drawbacks with respect to monitoring in the IVC. Electrical impedance-based systems require electrodes that are specifically placed in opposition across the width of the vessel. Such devices present special difficulties when attempting to monitor IVC dimensions due to the fact that the IVC does not expand and contract symmetrically as do most other vessels where monitoring may be desired. Precise positioning of such position-dependent sensors is a problem that has not yet been adequately addressed. IVC monitoring presents a further challenge arising from the physiology of the IVC. The IVC wall is relatively compliant compared to other vessels and thus can be more easily distorted by forces applied by implants to maintain their position within the vessel. Thus devices that may perform satisfactorily in other vessels may not necessarily be capable of precise monitoring in the IVC due to distortions created by force of the implant acting on the IVC wall. As such, new developments in this field are desirable in order to provide doctors and patients with reliable and affordable wireless vascular monitoring implementation, particularly in the critical area of heart failure monitoring.

SUMMARY OF THE DISCLOSURE

Embodiments disclosed herein comprise wireless vascular monitoring devices, circuits, methodologies, and related techniques for use in assisting healthcare professionals in predicting, preventing, and diagnosing various conditions whose indicators may include vascular fluid status. Using embodiments disclosed, metrics including, for example, relative fluid status, fluid responsiveness, fluid tolerance, or heart rate may be accurately estimated.

In one implementation, the present disclosure is directed to a wireless vascular monitoring implant adapted to be deployed and implanted in a patient vasculature and positioned at a monitoring location in a vascular lumen in contact with the lumen wall. The implant includes a resilient sensor construct configured to dimensionally expand and contract with natural movement of the lumen wall; wherein an electrical property of the resilient sensor construct changes in a known relationship to the dimensional expansion and contraction thereof; and the resilient sensor construct produces a wireless signal indicative of the electrical property, the signal being readable wirelessly outside the vascular lumen to determine a dimension of the vascular lumen; the resilient sensor construct is configured and dimensioned to engage and substantially permanently implant itself on or in the lumen wall; the resilient sensor construct has a variable inductance correlated to its dimensional expansion and contraction along at least one dimension; and the resilient sensor construct produces, when energized by an energy source directed at the construct, a signal readable wirelessly outside the patient's body indicative of the value of the at least one dimension, whereby a dimension of the vascular lumen may be determined; wherein the resilient sensor construct comprises a coil configured to engage at least two opposed points on the vascular lumen wall, the coil having an inductance that varies based on the distance between the two opposed points on the coil corresponding a distance between the points on the lumen wall; wherein the coil is rotationally symmetrical about a longitudinal axis; wherein the resilient sensor construct is configured to expand and contract with the lumen wall along substantially any transverse axis of the vessel to change the variable inductance; wherein the resilient sensor construct, further comprises a frame having at least one resilient portion formed with at least two points configured to be positioned opposite one another so as to engage opposed surfaces of the vascular lumen wall when the sensor construct is positioned at the monitoring location in contact with the lumen wall, wherein the coil is formed on the frame by at least one wire disposed around the frame so as to form plural adjacent wire strands around the frame; wherein the resilient sensor construct comprises a resonant circuit having a resonant frequency that varies with the variable inductance, the signal being correlated with the resonant frequency; wherein the coil comprises a resonant circuit having inductance and a capacitance defining a resonant frequency, wherein the resonant frequency varies based on the distance between the at least two points; and the coil is configured to be energized by a magnetic field directed at the coil from outside the patient's body.

In another implementation, the present disclosure is directed to a wireless vascular sensing system that includes a wireless vascular monitoring implant adapted to be deployed and implanted in a patient vasculature and positioned at a monitoring location in a vascular lumen in contact with the lumen wall, the implant comprising a resilient sensor construct configured to dimensionally expand and contract with natural movement of the lumen wall; wherein an electrical property of the resilient sensor construct changes in a known relationship to the dimensional expansion and contraction thereof; and the resilient sensor construct produces a wireless signal indicative of the electrical property, the signal being readable wirelessly outside the vascular lumen to determine a dimension of the vascular lumen; and further comprising means for excitation of the resilient sensor construct to produce a frequency response signal indicative of a dimension of the lumen at a time correlated to the excitation; an antenna module configured to at least receive the frequency signal from the implant, the antenna module further configured to be disposed outside the patient's body; and a control system communicating with the antenna module to at least receive a representation of the frequency signal from the antenna module and present data interpreting the frequency signal to estimate a dimension of the vascular lumen at the monitoring location.

In still another implementation, the present disclosure is directed to a system for monitoring a patient vascular lumen dimension. The system includes a wireless vascular sensor configured to be positioned in a vascular lumen at a monitoring location in engagement with the lumen wall, the sensor including a resonant circuit with a resonant frequency that varies correlated to expansion and contraction of the sensor with natural movement of the lumen wall in response to changes in patient fluid volume; means for exciting the resonant circuit of the sensor to produce a frequency signal indicative of a dimension of the lumen at a time correlated to the exciting; an antenna module configured to at least receive the frequency signal from the implant, the antenna module further configured to be disposed outside the patient's body; and a control system communicating with the antenna module to at least receive a representation of the frequency signal from the antenna module and present data interpreting the frequency signal to estimate the patient fluid status based on a sensed vascular lumen dimension; comprising a wearable antenna comprising a belt configured to be wrapped around a patient's waist or torso to form a first coil around a first axis; and a wireless sensor comprising a second coil formed around a second axis, the wireless vascular sensor being configured to be implanted in a vessel such that the second axis is generally parallel to the first axis; wherein a current in the first coil produces a first electromagnetic field, the first electromagnetic field passing through the second coil along the second axis, thereby producing a current in the second coil resulting in a signal receivable by the first coil of the wearable antenna; further comprising a control system configured to generate the current in the first coil and receive the signal from the first coil, the control system including a switch for switching between a transmit mode wherein a current is sent to the first coil and a receive mode wherein a signal is received by the first coil; wherein the second coil comprises a resonant circuit with a resonant frequency that varies in correlation to a physiological parameter to be measured and receivable signal comprises a frequency signal produced by the resonant circuit; wherein the wireless sensor is a vascular sensor comprising a resilient sensor construct configured to be positioned within a vascular lumen and substantially permanently implant itself on or in the lumen wall, the sensor construct including a coil configured to expand and contract with the lumen wall along substantially any transverse axis of the vascular lumen to change the variable resonant frequency and wherein the coil is rotationally symmetrical about a longitudinal axis so as to be operable at any rotational position within the vascular lumen.

In still another implementation, the present disclosure is directed to a method for wirelessly monitoring changes in a dimension of a body lumen of a patient. The method includes wirelessly receiving outside the patient's body a variable inductance-based signal from an implant substantially permanently implanted on or in the body lumen wall wherein the variable inductance-based signal varies based on changes in geometry of the lumen wall; further comprising energizing the implant to produce the variable inductance-based signal in response to the energizing; wherein the body lumen comprises a patient vascular lumen and the method further comprises delivering the implant to a monitoring location within the vascular lumen; wherein the delivering comprises: placing the implant within a sheath of a delivery catheter; intravascularly positioning a distal end of the delivery catheter at the monitoring location; and deploying the implant from the delivery catheter with a deployment member slideably disposed in the sheath; wherein: the implant comprises a resiliently expandable and collapsible sensor construct; the placing comprises collapsing the sensor construct to be placed within the sheath; and the deploying comprises forcing the sensor construct out of the distal end of the sheath such that a leading end of the sensor construct expands to contact the vascular lumen wall before a trailing end of the sensor construct leaves the delivery catheter.

In yet another implementation, the present disclosure is directed to a method for wirelessly monitoring changes in a dimension of a body lumen of a patient. The method includes wirelessly receiving outside the patient's body a variable inductance-based signal from an implant substantially permanently implanted on or in the body lumen wall wherein the variable inductance-based signal varies based on changes in geometry of the lumen wall; wherein the variable inductance-based signal varies based on changes in geometry of the wall of a vascular lumen within which the implant is implanted and the method further comprises: processing the signal to determine variations in vascular lumen area over time, wherein the variations in vascular lumen area are correlateable to patient fluid status; and interpreting the determined variations in lumen area over time to assess patient fluid status.

In a further implementation, the present disclosure is directed to a diagnostic method for determining patient fluid status. The method includes wirelessly receiving outside the patient's body a variable inductance-based signal from an implant substantially permanently implanted on or in a wall of a vascular lumen wherein the variable inductance-based signal varies based on changes in geometry of the lumen wall; processing the signal to determine variations in vascular lumen area over time, wherein the variations in vascular lumen area are correlateable to patient fluid status; and interpreting the determined variations in lumen area over time to assess patient fluid status.

These and other aspects and features of non-limiting embodiments of the present disclosure will become apparent to those skilled in the art upon review of the following description of specific non-limiting embodiments of the invention in conjunction with the accompanying drawings.

BRIEF DESCRIPTION OF THE DRAWINGS

For the purpose of illustrating the disclosure, the drawings show aspects of one or more embodiments of the disclosure.

However, it should be understood that the present disclosure is not limited to the precise arrangements and instrumentalities shown in the drawings, wherein:

FIGS. 5A and 5B illustrate fixed frequency RF burst excitation signal wave forms;

FIGS. 6A and 6B illustrate sweep frequency RF burst excitation signal wave forms;

FIGS. 9A, 9B and 9C schematically illustrate aspects of an embodiment of a delivery system for RC-WVM implants as disclosed herein, wherein FIG. 9A shows an overall view of the delivery system and its sub-components, FIG. 9B shows a detail of the distal end with the RC-WVM loaded, and FIG. 9C depicts a partial deployment of an RC-WVM implant from the delivery sheath into the IVC;

FIGS. 12A, 12B, 12C, 13A, 13B, 13C, 13D, 14A, 14B, 15A, 15B, 16A, 16B, 17A, 17B, 18, 19A, and 19B illustrate alternative embodiments of RC-WVM implants according to the present disclosure;

FIGS. 27A and 27B illustrate alternative belt antenna embodiments utilizing variable length of coil features;

FIGS. 28A and 28B illustrate alternative active and passive diode switches for use in antenna element embodiments disclosed herein;

DETAILED DESCRIPTION

Aspects of the present disclosure are directed to wireless, resonant circuit-based vascular monitoring ("RC-WVM") implants, systems, methods, and software, including excitation and feedback monitoring ("EFM") circuits that can be used to energize an RC-WVM implant with an excitation signal and receive characteristic feedback signals produced by the RC-WVM implant. By automatically or manually analyzing the feedback produced by the RC-WVM implant, it is possible to assist healthcare professionals in predicting, preventing, and diagnosing various heart-related, kidney-related, or vascular-related health conditions. For example, the feedback produced by the RC-WVM implant at a particular time can be compared to feedback produced by the RC-WVM implant at other times and/or feedback produced by a baseline RC-WVM implant in order to understand vessel geometry and therefore estimate relative fluid status, fluid responsiveness, fluid tolerance, heart rate, respiration rate and/or other metrics. One or more of these estimations can be generated automatically or manually in order to monitor the status of a patient and provide feedback to a healthcare professional and/or the patient in case of any anomalies or relevant trends.

System Overview

The unique physiology of the IVC presents some distinctive challenges in attempting to detect and interpret changes in its dimensions arising from changes in patient fluid state. For example, the IVC wall in a typical monitoring region (i.e., between the hepatic and renal veins) is relatively compliant compared to other vessels, which means that changes in vessel volume can result in different relative distance changes between the anterior-posterior walls as compared to the lateral-medial walls. Thus, it is quite typical that changes in fluid volume will lead to paradoxical changes in the geometry and motion of the vessel; that is, as the blood volume reduces the IVC tends to get smaller and collapse with respiration, and as the blood volume increases the IVC tends to get larger and the collapse with respiration is reduced. Systems and implants disclosed herein are uniquely configured to compensate for and interpret such paradoxical changes.

Figure 1:
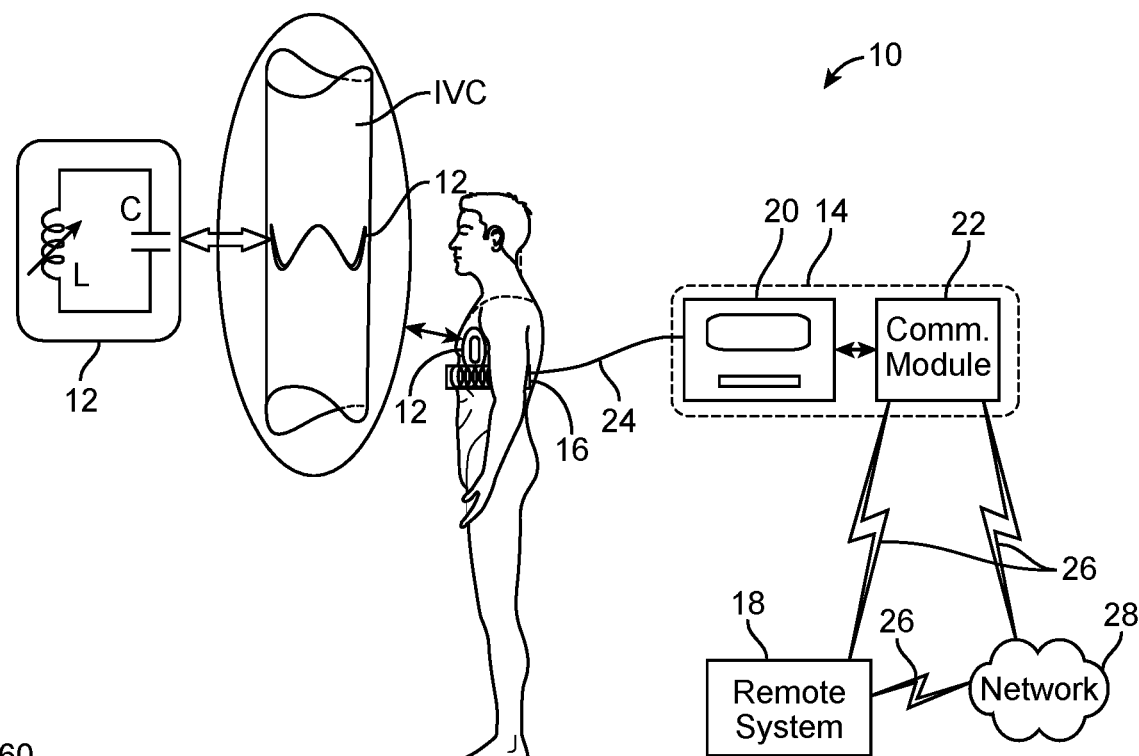
FIG. 1 schematically depicts an embodiment of a wireless resonant circuit-based vascular monitoring ("RC-WVM") system of the present disclosure.

As shown in FIG. 1, systems 10 according to the present disclosure may generally comprise RC-WVM implant 12 configured for placement in a patient's IVC, control system 14, antenna module 16 and one or more remote systems 18 such as processing systems, user interface/displays, data storage, etc., communicating with the control and communications modules through one or more data links 26, which may be wired or remote/wireless data links. In many implementations, remote system 18 may comprise a computing device and user interface, such as a laptop, tablet or smart phone, which serves as an external interface device.

RC-WVM implants 12 generally comprise a variable inductance, constant capacitance, resonant L-C circuit formed as a resiliently collapsible coil structure, which, when positioned at a monitoring position within the patient's IVC, moves with the IVC wall as it expands and contracts due to changes in fluid volume. The variable inductance is provided by the coil structure of the implant such that the inductance changes when the dimensions of the coil change with the IVC wall movement. The capacitive element of the circuit may be provided by a discrete capacitor or specifically designed inherent capacitance of the implant structure itself. Embodiments of RC-WVM implant 12 also may be provided with anchoring and isolation means inherently designed into the implant structure, or with distinct additional such structures, to ensure that the implant is securely and properly positioned in the IVC without unduly distorting the vessel wall so as to distort or otherwise negatively impact measurements determined by the implant. In general, RC-WVM implants 12 are configured to at least substantially permanently implant themselves in the vascular lumen wall where placed upon deployment and do not require a physical connection (for communications, power or otherwise) to devices outside the patient's body after implantation. "Substantially permanently implanted" as used herein means that in normal usage the implant will, throughout its useful, operational life, remain implanted in the vascular lumen wall and may to varying degrees become integrated into the vascular lumen wall by tissue ingrowth, but the implant may be intentionally removed as medically dictated by an intravascular interventional or surgical removal procedure specifically undertaken for the purpose of removing the implant. Details of alternative embodiments of implant 12, shown in FIGS. 2, 2A, 12A, 12B, 12C 13A, 13B, 13C, 13D, 14A, 14B, 15A, 15B, 16A, 16B, 17A, 17B, 18, 19A, and 19B, are provided below. In particular, it should be noted that any of alternative RC-WVM implants 12, specifically any of implant embodiments 12a-k, m, n and p, may be utilized in alternative systems 10 as described herein without further modification of the systems except as may be identified.

Control system 14 comprises, for example, functional modules for signal generation, signal processing and power supply (generally comprising the EFM circuits and indicated as module 20) and communications module 22 to facilitate communication and data transfer to various remote systems 18 through data links 26 and optionally other local or cloud-based networks 28. Details of alternative embodiments of control system 14, modules 20 and 22, and elements of alternative EFM circuits are described below and illustrated in FIGS. 4, 7, 24A, 24B, 25A, 25B, 26A, 26B and 26C. After analyzing signals received from RC-WVM implant 12 after being excited by a transmit coil of an EFM circuit, results may be communicated manually or automatically through remote system 18 to the patient, a caregiver, a medical professional, a health insurance company, and/or any other desired and authorized parties in any suitable fashion (e.g., verbally, by printing out a report, by sending a text message or e-mail, or otherwise).

Antenna module 16 is connected to control system 14 by power and communication link 24, which may be a wired or wireless connection. Antenna module 16 creates an appropriately shaped and oriented magnetic field around RC-WVM implant 12 based on signals provided by the EFM circuitry of control system 14. The magnetic field energizes the L-C circuit of RC-WVM implant 12 causing it to produce a "ring-back" signal indicative of its inductance value at that moment. Because the inductance value is dependent on the geometry of the implant, which changes as mentioned above based on dimensional changes of the IVC in response to fluid state heart rate etc., the ring-back signal can be interpreted by control system 14 to provide information as to the IVC geometry and therefore fluid state. Antenna module 16 thus also provides a receive function/antenna as well as a transmit function/antenna. In some embodiments the transmit and receive functionality are performed by a single antenna, in others each function is performed by a separate antenna. Antenna module 16 is schematically depicted in FIG. 1 as an antenna belt, which embodiment is described in more detail below and shown in FIGS. 3A-D.

Figure 1A:
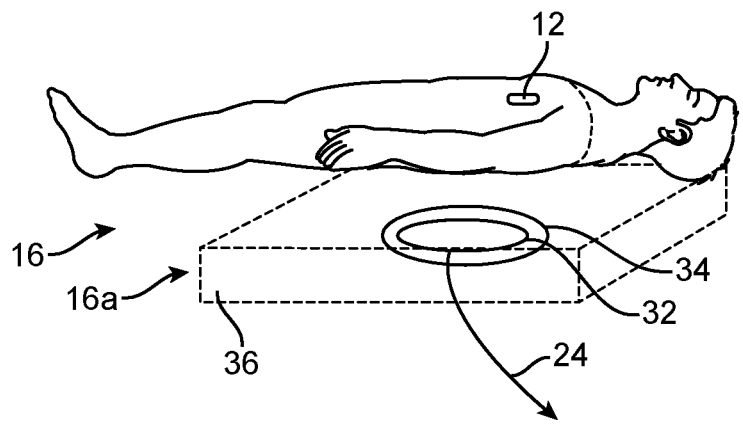
FIG. 1A schematically depicts a portion of an alternative embodiment of a RC-WVM system of the present disclosure.

FIG. 1A illustrates one alternative embodiment of antenna module 16 as antenna pad 16a, in which transmit coil 32 and receive coil 34 are disposed in a pad or mattress 36 on which the patient lays on his/her back with RC-WVM implant 12 (implanted in the IVC) positioned over coils 32, 34. Antenna module 16 as shown in FIG. 1A is functionally equivalent to other alternative antenna modules disclosed herein; it is connected to control system 14 by power and communications link 24 as described above. Further alternative embodiments and components of antenna module 16 are also shown in FIGS. 22A, 22B, 27A, 27B, 28A, 28B, 29A and 29B and described in more detail below. Planar-type antenna modules also may be configured in wearable configurations, e.g., wherein the antenna coil is integrated into a wearable garment such as a backpack or vest. Antenna module 16 may also comprise a coil adapted to be fastened directly to the patient's skin by tape, glue or other means, e.g. over the abdomen or back, or integrated into furniture such as a chair back. As will be appreciated by persons skilled in the art, the various embodiments of antenna module 16 as described herein may be employed with system 10 as shown in FIG. 1 without further changes to the system or antenna module other than as specifically identified herein.

The variable inductance L-C circuit produces a resonant frequency that varies as the inductance is varied. With the implant securely fixed at a known monitoring position in the IVC, changes in geometry or dimension of the IVC cause a change in configuration of the variable inductor, which in turn cause changes in the resonant frequency of the circuit. These changes in the resonant frequency can be correlated to changes in the vessel geometry or dimension by the RC-WVM control and communication system. Thus, not only should the implant be securely positioned at a monitoring position, but also, at least a variable coil/inductor portion of the implant should have a predetermined resilience and geometry. Thus, in general, the variable inductor is specifically configured to change shape and inductance in proportion to a change in the vessel geometry. In some embodiments, an anchoring and isolation means will comprise appropriately selected and configured shape and compliance in the sensor coil structure of the implant so as to move with the vessel wall while maintaining position. Such embodiments may or may not include additional anchoring features as discussed in more detail below. Alternatively, an anchoring and isolation means may comprise a separate structure spaced and/or mechanically isolated from a variable inductor coil structure such that the anchoring function is physically and/or functionally separated from the measuring/monitoring function such that any distortion or constraint on the vessel caused by the anchor is sufficiently distant and/or isolated from the variable inductor so as not to unduly affect measurements.

RC-WVM implant 12 as a variable inductor is configured to be remotely energized by an electric field delivered by one or more transmit coils within the antenna module positioned external to the patient. When energized, the L-C circuit produces a resonant frequency which is then detected by one or more receive coils of the antenna module. Because the resonant frequency is dependent upon the inductance of the variable inductor, changes in geometry or dimension of the inductor caused by changes in geometry or dimension of the vessel wall cause changes in the resonant frequency. The detected resonant frequency is then analyzed by the RC-WVM control and communication system to determine the change in the vessel geometry or dimension. Information derived from the detected resonant frequency is processed by various signal processing techniques as described herein and may be transmitted to various remote devices such as a healthcare provider system or patient system to provide status, or in appropriate instances, alerts or modifications in treatment. In order to facilitate measurement of the detected resonant frequency, it may be desirable to provide designs with a relatively higher Q factor, i.e. resonant circuit configurations that maintain signal/energy for relatively longer periods, especially when operating at lower frequencies. For example, to realize advantages of designs employing Litz wire as further described herein, it may be desirable to operate in a resonant frequency range of below 5 MHz, typically between about 1 MHz and 3 MHz, in which case resonant circuit configuration with a Q factor of at least about 50 or greater may be desired.

An Example of a Complete System Embodiment

Details of one possible embodiment of a complete, exemplary system 10 are discussed hereinafter with reference to FIGS. 2-8C. Thereafter, details of further alternative embodiments of system components are described. However, it is to be understood that the exemplary system is not limited to use of the specific elements or components shown in FIGS. 2-7 and 9A-C and that any alternative component thereafter described may be substituted without change in the overall system except as may be noted. For example, RC-WVM implant 12 or any of alternative RC-WVM implants 12c-k, m, n and p may be substituted for implants 12a or 12b as first described below. Similarly, control system 14 may be provided as shown in any of FIGS. 4, 24A, 24B, 26A, 26B, 26C, 28A, 28B, 29A and 29B and/or antenna module 16 may be provided, for example, as a pad or belt an antenna such as pad antenna 16a, with a single switched antenna coil or separate, decoupled transmit and receive coils, or belt antennas 16b, 16c, 16d, 16e or 16f.

Figure 2:
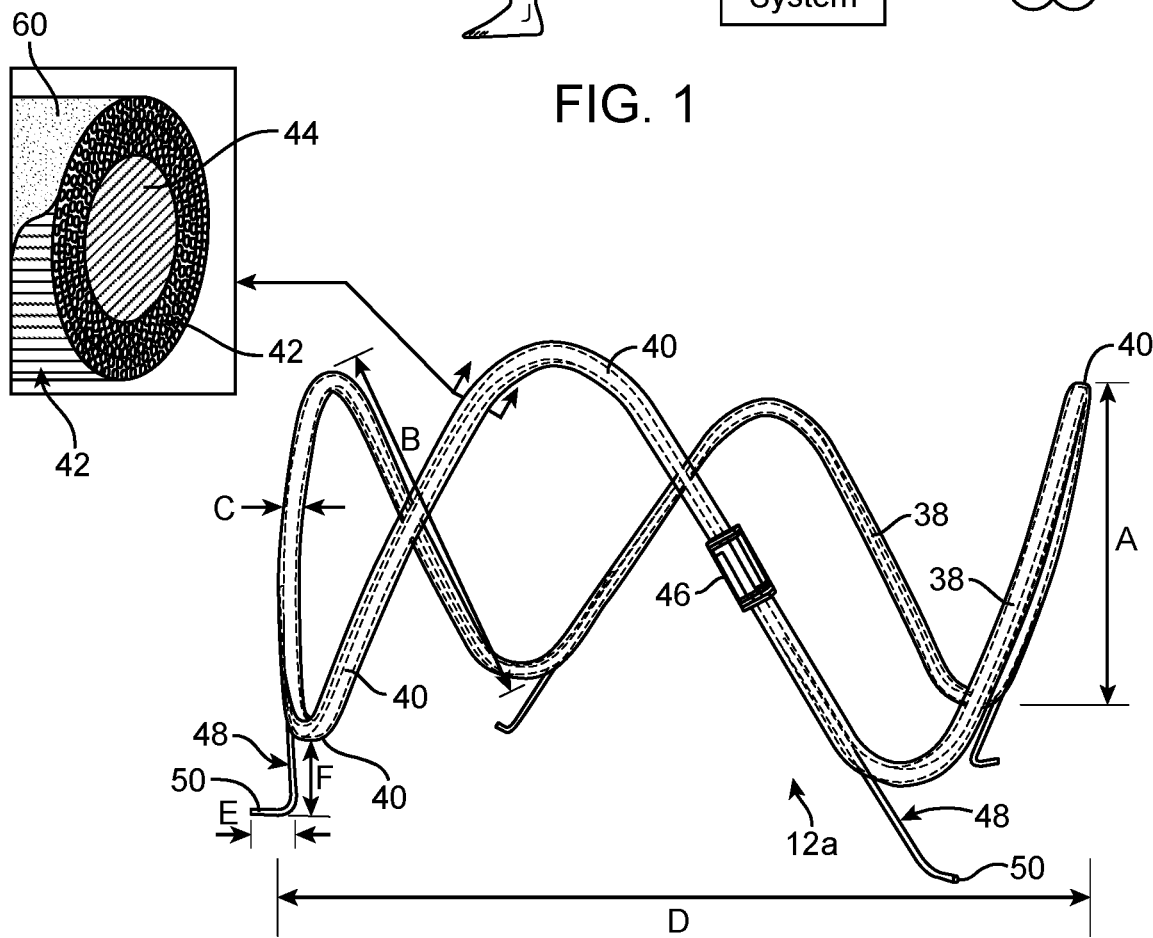
FIGS. 2 and 2A illustrate alternative embodiments of RC-WVM implants made in accordance with the teachings of the present disclosure.

FIG. 2 illustrates one example of RC-WVM implant 12 according to the present disclosure as may be used in exemplary system 10. The enlarged detail in the box of FIG. 2 represents a cross-sectional view taken as indicated. (Note that in the cross-sectional view, individual ends of the very fine wires may not be distinctly visible due to their very small size). In general, RC-WVM implants 12 comprise a resilient sensor construct generally including an inductive coil formed around an open center that to allow substantially unimpeded blood flow there through, wherein the inductive coil changes inductance with changes in the construct geometry as a result of forces applied to it. In this example, implant 12a is formed as a resilient, concentric zig-zag or linked "Z-shapes" structure with a series of straight strut sections 38 joined at their ends by rounded crown sections 40 forming acute angles. The resultant structure may also be considered to be sinusoidal in appearance. This structure may be formed by wrapping conductive wires 42 onto a frame or core 44. In this alternative, RC-WVM implant 12a has a shape set 0.010" nitinol wire frame 44 around which 300 strands of 0.04 mm diameter gold, individually insulated, Litz wire 42 are wrapped in a single loop. With a single loop wrap, the strands of wire 42 appear substantially parallel to the frame at any given point, as can be seen in the cross-section view of FIG. 2. Individual insulation on Litz wires 42 may be formed as a biocompatible polyurethane coating. Also in this particular example, discrete capacitor 46 is provided with a capacitance of approximately 47ηF (nano-Farads); however, the capacitance may be in the range of about 180 pico-Farads to about 10 micro-Farads, to cover all potential allowable frequency bands (from about 148.5 kHz to about 37.5 MHz) for RC-WVM implants 12. In one alternative, rather than a relatively large number of wire strands in a single loop, a relatively few number of strands, e.g. in the range of about 10-20 strands, or more particularly about 15 strands, may be arranged in a relatively larger number of loops, e.g. in the range of about 15-25 loops, or more particularly about 20 loops. In this embodiment the discrete capacitor element is replaced with an inherent coil capacitance that arises based spaces between the parallel strands of wire.

Figure 2A:
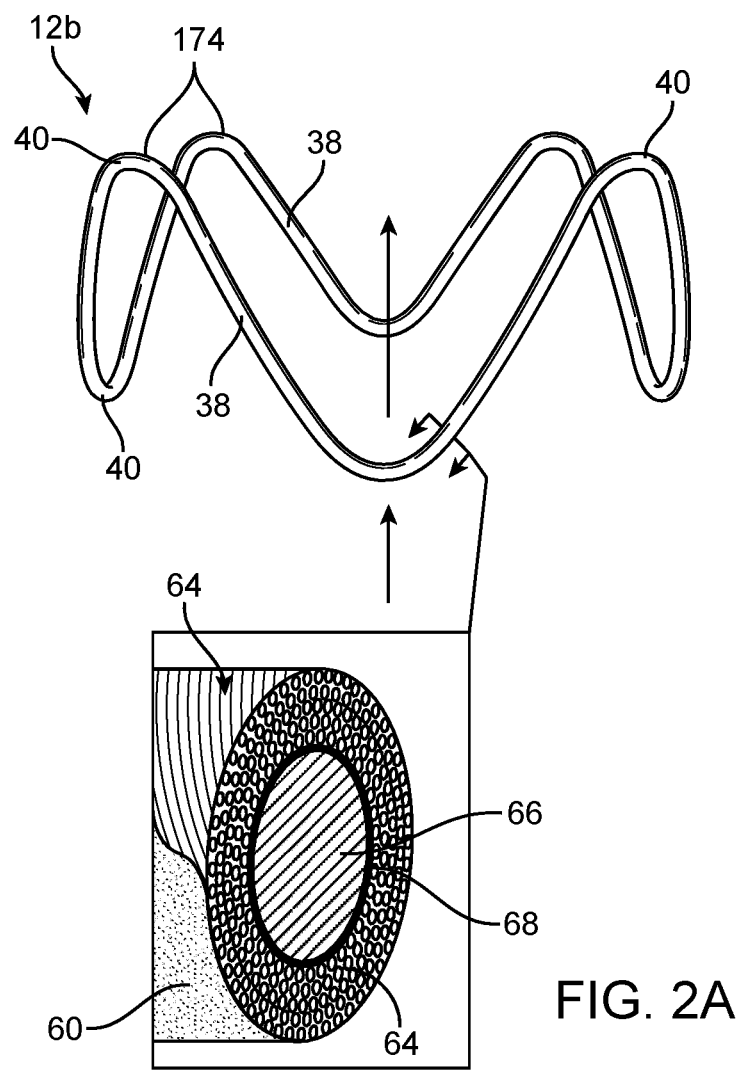
Figure 2B:
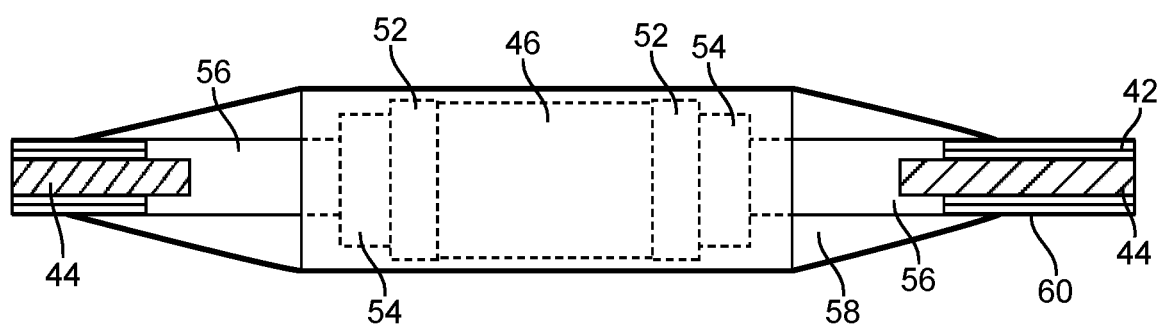
FIG. 2B is a schematic, detailed view of the capacitor section of the RC-WVM implant illustrated in FIG. 2.

With reference also to FIG. 2B, Litz wire 42 is formed around a shape set nitinol frame 44. The two ends of Litz wire 42, which may be covered with a layer of PET heat shrink tubing 60, are joined together with a capacitor 46 to form a loop circuit. Capacitor 46 includes capacitor terminals 52 connected to Litz wires 42 by solder connection 54 to gold wire contacts 56. Gold wire contacts 56 are formed by removing (or burning away) the individual insulation from a short section at the end of Litz wires 42 and joining those ends to form solid contacts, which then may be joined to capacitor terminals 52 by solder connections 54. The capacitor, capacitor terminals and gold wire contacts are encapsulated in an appropriate biocompatible insulating material 58 such as a reflowed polymer or epoxy. In alternative embodiments, the entire structure may then be covered by a layer of PET heat shrink insulation 60. Alternatively, if determined that a short circuit through the frame should not be created, a gap may be provided in the frame at the capacitor or elsewhere.

RC-WVM implant 12a is also optionally provided with anchors 48 to help prevent migration of the implant after placement in the IVC. Anchors 48 also may be formed of nitinol laser cut sections or shape set wire and bonded to each strut section 38. Barbs 50 extend outwardly at the end of anchors 48 to engage the IVC wall. In one embodiment, anchors 48 are bi-directional in both the cranial and caudal directions; in other embodiments the anchors may be in one direction, a mixture of both directions or perpendicular to the vessel.

The overall structure of RC-WVM implants 12 presents a balance of electrical and mechanical requirements. For example, an ideal electrical sensor is as close to a solenoid as possible with strut lengths as short as possible and ideally zero, whereas mechanical considerations of deployment and stability dictate that implant strut lengths be at least as long as the diameter of the vessel into which it is to be deployed to avoid deployment in the wrong orientation and maintain stability. Dimensions of elements of RC-WVM implant 12a are identified by letters A-F in FIG. 2, and examples of typical values for those dimensions, suited for a range of patient anatomies, are provided below in Table I. In general, based on the teachings herein, persons skilled in the art will recognize that the uncompressed, free-state (overall) diameter of RC-WVM implants 12 should not significantly exceed the largest anticipated fully extended IVC diameter for the patient in which the RC-WVM implant is to be used. RC-WVM implant height generally should be selected to balance implant stability at the monitoring position with geometry/flexibility/resilience providing the ability to fit in the intended region of the IVC without impacting either the hepatic or renal veins in the majority of the population, which could compromise sensing data produced by the implant. Height and stability considerations will be influenced, among other factors, by specific RC-WVM implant design configuration and whether or not distinct anchor features are included. Thus, as will be appreciated by persons skilled in the art, primary design considerations for RC-WVM implants 12 according to the present disclosure are provision of structures forming variable inductance L-C circuits with the ability to perform the measuring or monitoring function described herein, and which are configured to securely anchor the structures within the IVC without distortion of the IVC wall by providing adequate but relatively low radial force against the IVC wall.

TABLE I

RC-WVM Implant 12a & 12b
Example Dimensions

| Dim. | Element Name | Approximate Size (in millimeters) |
|---|---|---|
| A | Height | 10-100, typically about 20 |
| B | Strut length | 10-100, typically about 25 |
| C | Strut diam. | 0.1-2, typically about 1.5 |
| F | Anchor Length (extending) | 1-10, typically about 5 |
| E | Anchor Length (barb) | 0.25-3, typically about 1.8 |
| D | Overall Diameter | Three Sizes: 20 mm/25 mm/32 mm +/−3 mm |

Another alternative structure for RC-WVM implant 12 is illustrated by RC-WVM implant 12b as shown in FIG. 2A. Once again, the enlarged detail in the box of FIG. 2A represents a cross-sectional view taken as indicated. In this embodiment, implant 12b has an overall structure that is similar to that of implant 12a, formed on a frame with straight strut sections 38 and curved crown sections 40. In this embodiment, the discrete capacitor for the previous embodiment is replaced with distributed capacitance between the bundles of strands of wire. Multiple (for example, approximately fifteen) strands of wire 64 are laid parallel to each other and twisted into a bundle. This bundle is then wrapped, multiple times, around the entire circumference of wire frame 66 (which may be, for example, a 0.010" diameter nitinol wire) resulting in multiple turns of parallel bundles of strands. The insulation between the bundles results in a distributed capacitance that causes the RC-WVM to resonate as previously. Overall dimensions are similar and may be approximated as shown in Table I. An outer, insulation layer or coating 60 may be applied either as previously described or using a dipping or spraying process In this case, the L-C circuit is created without a discrete capacitor, but instead by tuning the inherent capacitance of the structure through selection of materials and length/configuration of the wire strands. In this case, 20 turns of 15 strands of wire are used along with an outer insulation layer 60 of silicone to achieve a capacitance inherent in implant 12b in the range of approximately 40-50 ηF.

Unlike implant 12a, frame 66 of implant 12b is non-continuous so as to not complete an electrical loop within the implant as this would negatively impact the performance. Any overlapping ends of frame 66 are separated with an insulating material such as heat shrink tubing, an insulating epoxy or reflowed polymer. RC-WVM implant 12b (may or) may not include anchors. Instead, the implant is configured to have a compliance/resilience to permit it to move with changes in the IVC wall geometry or dimension while maintaining its position with minimal distortion of the natural movement of the IVC wall. This configuration can be achieved by appropriate selection of materials, surface features and dimensions. For example, the strut section length of the frame must balance considerations of electrical performance versus stability, wherein shorter strut section length may tend to improve electrical performance but longer strut section length may increase stability.

In order to energize RC-WVM implant 12 and receive the signal back from the implant, antenna module 16 will functionally include a transmit and a receive antenna (or multiple antennas). Antenna module 16 thus may be provided with physically distinct transmit and receive antennas, or, as in the presently described exemplary system 10, provided by a single antenna that is switched between transmit and receive modes. Antenna belt 16b, shown FIGS. 3 and 3A-D, illustrates an example of antenna module 16 employing a single, switched antenna.

In terms of mechanical construction, belt antenna 16b generally comprises stretchable web section 72 and buckle 74 with a connection for power and data link 24. In one embodiment, in order for size antenna belt to accommodate patients of different girths (e.g., a patient girth range of about 700-1200 cm), a multi-layer construction made up of a combination of high-stretch and low-stretch materials may be employed. In such an embodiment, base layer 76 is a combination of high-stretch sections 76a and low-stretch section 76b, which are joined such as by stitching. Outer layer 78, with substantially the same profile as base layer 76, may be comprised entirely of the high-stretch material, which may be a 3D mesh fabric. Within each section, antenna core wire 82 is provided in a serpentine configuration with an overall length sufficient to accommodate the total stretch of the section. Core wire 82 should not itself stretch. Thus, the stretchability of the fabric layers is paired with the core wire total length to meet the desired girth accomodation for a particular belt design. Outer layer 78 is joined along the edges to base layer 76. Stitching covered by binding material 80 is one suitable means for joining the two layers. The layers may be further bonded together by a heat fusible bonding material placed between the layers. End portions 81 of web section 72 are configured for attachment to buckle 74.

Core wire 82, which forms the antenna element, is disposed between the layers and provided with an extendable, serpentine configuration so that it may expand and contract with the stretch of the belt. A mid-section 84 of core wire 82, which corresponds to low-stretch section 76b, has a greater width. This section, intended to be placed in the middle of the patient's back with antenna belt 16b worn approximately at chest level at the bottom of the rib cage, provides greatest sensitivity for reading the signal from RC-WVM implant 12. As one possible example, core wire 82 may be made up of 300 strands of twisted 46 AWG copper wire with a total length in the range of approximately 0.5-3 m. For an antenna belt configured to accommodate patient girths in the range of about 700 to 1200 mm, the total length of core wire 82 may be approximately 2 m.

Many ways of providing a workable buckle for such an antenna belt may be derived by persons of ordinary skill based on the teachings contained herein. Factors to be considered in designing such a buckle include physical security, ease of manipulation by persons with reduced dexterity and protection from electrical shock by inadvertent contact with the electrical connectors. As an example, buckle 74 is comprised of two buckle halves, inner half 74a and outer half 74b. Buckle 74 provides not only physical connection for the belt ends, but also electrical connection for the antenna circuit formed by core wire 82. With respect to the physical connection, buckle 74 is relatively large in size to facilitate manipulation by persons with reduced dexterity. A magnetic latch may be employed to assist closure, for example magnetic pads 86a on inner buckle half 74a connect to magnetic pads 86b correspondingly disposed on buckle outer half 74b. If desired, the system can be configured to monitor for completion of the belt circuit and therefore detect belt closure. Upon confirmation of belt closure, the system may be configured to evaluate the signal strength received from the implant and an assessment made if the received signal is sufficient for a reading to be completed. If the signal is insufficient, an instruction may be provided to reposition the belt to a more optimal location on the patient.

Electrical connection of core wire 82 may be provided by recessed connector pins disposed on opposed connector halves 88a and 88b. Connection of power and data link 24 may be provided, for example, through a coaxial RF cable with coaxial connectors (e.g., SMA plugs) on buckle 74 and control system 14. As just one possible example, a convenient length for the power and data link, using a conventional, 50 Ohm coax cable, is about 3 m.

As mentioned above, use of a single coil antenna as in antenna belt 16b requires switching the antenna between transmit and receive modes. Such switching is executed within control system 14, an example of which is schematically depicted as control system 14a in FIG. 4. In this embodiment, control system 14a includes as functional modules 20 a signal generator module 20a and a receiver-amplifier module 20b. These functional modules, along with transmit/receive (T/R) switch 92 provide for the required switching of antenna belt 16b between the transmit and receive modes.

Figure 3:
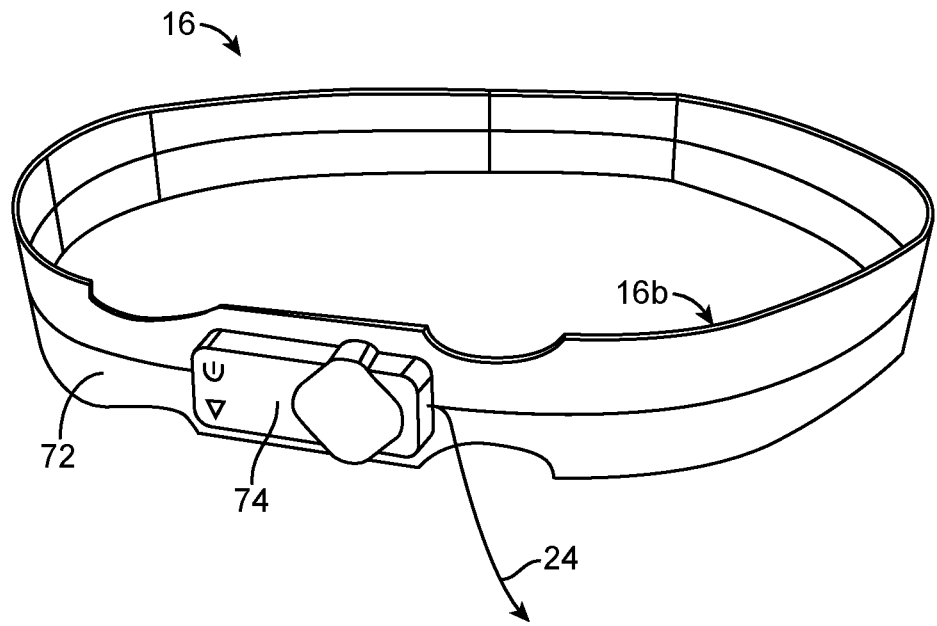
FIGS. 3, 3A, 3B, 3C and 3D illustrate an embodiment of a belt antenna as depicted schematically in the system of FIG. 1.
Figure 3A:
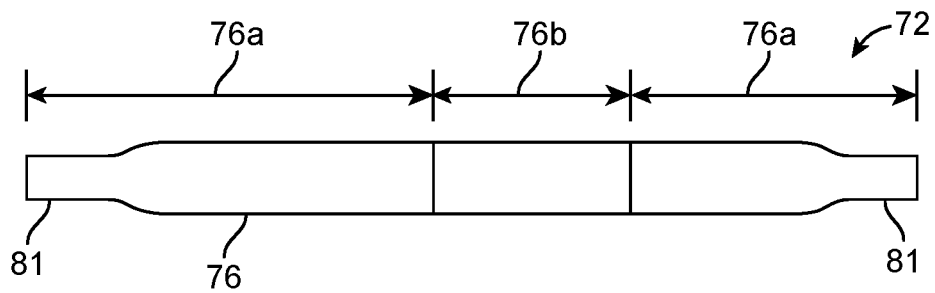
Figure 3B:
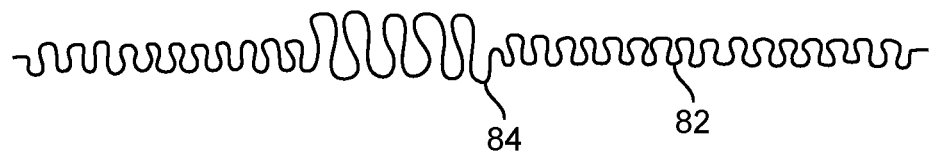
Figure 3C:
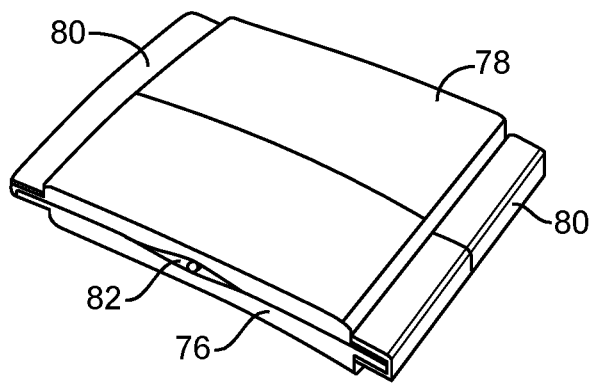
Figure 3D:
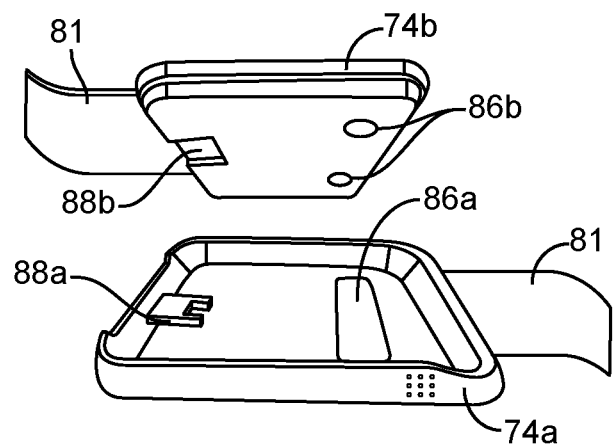
Figure 3E:
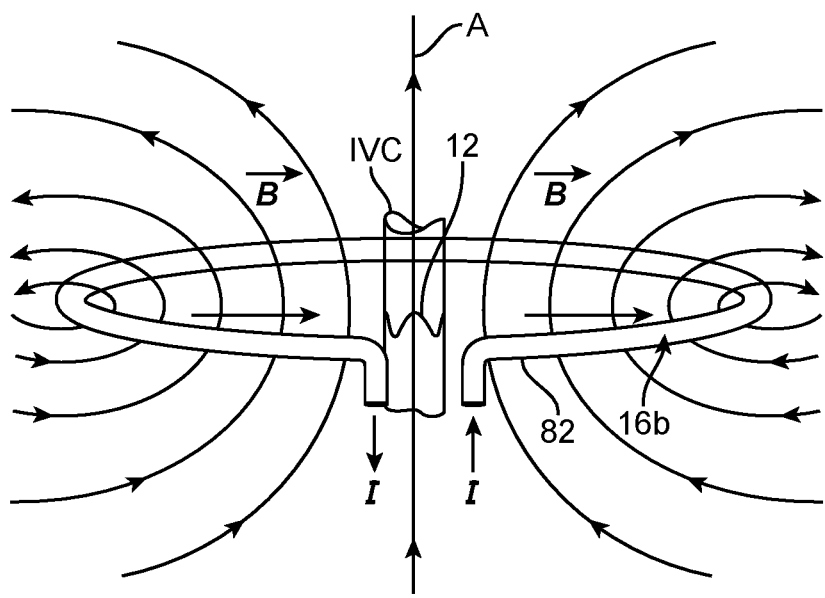
FIG. 3E schematically depicts the orientation of the antenna belt and magnetic field generated thereby with respect to an implanted RC-WVM implant.

FIG. 3E schematically illustrates the interaction of the magnetic field $\vec{B}$, created by antenna belt 16b, with RC-WVM implant 12. Both antenna belt 16b and implant 12 are generally disposed around an axis (A). For best results with a belt-type antenna, the axes around which each are disposed will lie in a substantially parallel orientation and, to the extent practicable, will lie coincident as shown in FIG. 3E. When properly oriented with respect to one another, current (I) in core wire 82 of antenna belt 16b generates magnetic field $\vec{B}$, which excites the coil of implant 12 to cause it to resonate at its resonant frequency corresponding to its size/geometry at the time of excitation. An orientation between the antenna belt 16b and implant 12 as shown in FIG. 3E minimizes the power necessary to excite the implant coil and produce a readable resonant frequency response signal.

As with any RF coil antenna system, the antenna and system must be matched and tuned for optimum performance. Values for inductance, capacitance and resistance and their interrelationship should be carefully considered. For example, the coil inductance determines the tuning capacitance while the coil resistance (including the tuning capacitance) determines the matching capacitance and inductance. Given the relatively low power of the disclosed systems, special attention is given to these aspects to ensure that an adequately readable signal is generated by RC-WVM implant 12 upon actuation by the driving magnetic field. With an adjustable girth belt such as antenna belt 16b (or with different size antenna belts), additional considerations are presented because of the variable or different lengths of antenna coil controlled by the control system. To address these considerations, separate tuning-matching circuits 94, 96, as are understood in the art, are provided in signal generator module 20a and receiver-amplifier module 20b, respectively.

Using conventional coax cable for RF-power transmission, as is described above in one embodiment of power and data link 24, optimal RF power transfer between the antenna and the control system is achieved when the system and antenna impedances are matched to 50 Ohm real resistance. However, in the embodiment described above, resistance of antenna belt 16b is generally far below 50 Ohm. Transformation circuits, as part of tuning-matching circuits, 94, 96 can be used to transform the antenna resistance to 50 Ohm. In the case of antenna belt 16b it has been found a parallel capacitor transformation circuit is efficient for this purpose.

In one example of tuning using the system components heretofore described, a series capacitor was used, which, in conjunction with a matching capacitor, forms the total resonance. Using measured values as set forth below in Table II, a target resonance frequency was computed at 2.6 MHz based on the inductance and capacitance. Considering the inductance variation with stretching of antenna belt 16b at 2.6 MHz, the resonance frequency was measured to vary only from about 2.5 MHz to about 2.6 MHz for change in length between 1200 mm and 700 mm circumferences of antenna belt 16b, respectively. Considering the resistance of 11.1 Ohm, the Q-factor of the cable/belt assembly computes to be 3. Such a low Q-factor translates to a full width of the pulse at half maximum of 600 kHz. This is far less than the variation of the resonance frequency due to stretching of the belt from 700 mm to 1200 mm circumference. Tuning values for antenna belt 16b were thus determined at 2.6 MHz with $C_{match}$=2.2 nF and $C_{tune}$=2.2 nF.

TABLE II

Example of measured values for antenna belt 16b
Belt stretched to 28 cm dia. around water bottle

| Point of measurement | Resistance [Ohm] | Inductance [$10^{-6}$H] |
|---|---|---|
| Measured at buckle terminals with no cable connected | 0.3 | 1.69 |
| Measured at output of T/R switch 92 with 3 m coax cable connected | 11.1 | 3.03 |

While it could be expected that a variable length antenna, such as included in antenna belt 16b might present difficulties in tuning and maintaining the antenna tuning as the length changed, it was discovered that with the present configuration this was not the case. As described above, by intentionally employing a cable for power and data link 24 that has a relatively large inductance compared to the antenna inductance, the proportional change in the inductance due to changes in belt diameter are small enough not to degrade performance.

Referring again to FIG. 4 in addition to tuning-matching circuit 94, signal generator module 20a includes components that produce the signal needed for excitation of RC-WVM implant 12. These components include direct digital synthesizer (DDS) 98, anti-aliasing filter 100, pre-amplifier 102 and output amplifier 104. In one embodiment, the signal generator module 20a is configured to produce an RF burst excitation signal with a single, non-varying frequency tailored to a specific RC-WVM implant that is paired with the system (exemplary waveforms illustrated in FIGS. 5A and 5B). The RF burst comprises a predefined number of pulses of a sinusoidal waveform at the selected frequency with a set interval between bursts. The RF burst frequency value selected corresponds to the natural frequency of the paired RC-WVM implant 12 that would produce a lowest amplitude in the implant reader output. By doing this, optimum excitation is achieved for the worst case of implant response signal.

In an alternative implementation, control system 14 excites antenna module 16 at a pre-determined frequency that is within an expected bandwidth of the paired RC-WVM implant 12. The system then detects the response from the paired RC-WVM implant and determines the implant natural frequency. Control system 14 then adjusts the excitation frequency to match the natural frequency of the paired implant and continues to excite at this frequency for a complete reading cycle. As will be appreciated by persons of ordinary skill, frequency determination and adjustment as described for this embodiment may be implemented via software using digital signal processing and analysis.

In another alternative implementation, each individual RF burst comprises a continuous frequency sweep over a pre-defined range of frequencies equal to the potential bandwidth of the implant (FIG. 6A). This creates a broadband pulse that can energize the implant at all possible natural frequencies (FIG. 6B). The excitation signal can continue in this "within burst frequency sweep mode" or the control system can determine the natural frequency of the sensor and adjust to transmit solely at the natural frequency.

In a further alternative implementation, the excitation comprises a transitory frequency sweep over a set of discrete frequency values covering the potential bandwidth of the paired RC-WVM implant 12. The frequency is sequentially incremented for each RF burst and the RMS value of the RC-WVM implant response is evaluated after each increment. Control system 14 then establishes the frequency that produces the maximum amplitude in RC-WVM implant response and continues exciting the paired RC-WVM implant at that frequency until a drop of a predefined magnitude is detected and the frequency sweep is re-started.

In yet another implementation, the excitation signal is composed of a pre-defined set of frequencies, wherein each remain constant. Control system 14 excites antenna module 16 (and hence the paired implant) by applying equal amplitude at all frequency components. The system detects the response from the paired implant and determines its natural frequency. Control system 14 then adjusts the relative amplitude of the excitation frequency set to maximize the amplitude of the excitation frequency that is closest to the natural frequency of the paired implant. The amplitude of the other frequencies are optimized to maximize the response of the paired implant while meeting the requirements of electromagnetic emissions and transmission bandwidth limitations.

Figure 7:
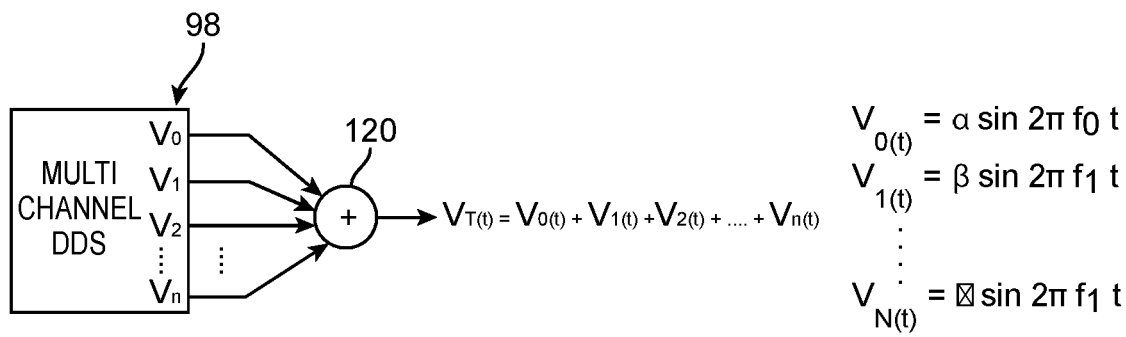
FIG. 7 is a block diagram depicting a multi-channel, direct digital synthesizer used in signal generation modules of control systems in embodiments disclosed herein.
Figure 7A:
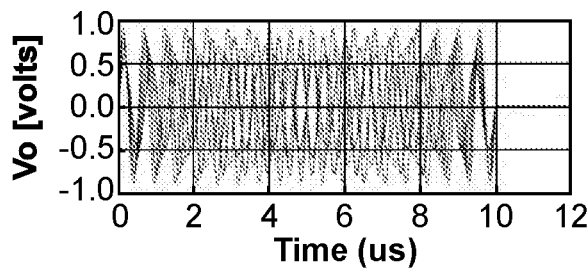
FIGS. 7A and 7B illustrate multi-frequency RF burst excitation signal wave forms.
Figure 7A:
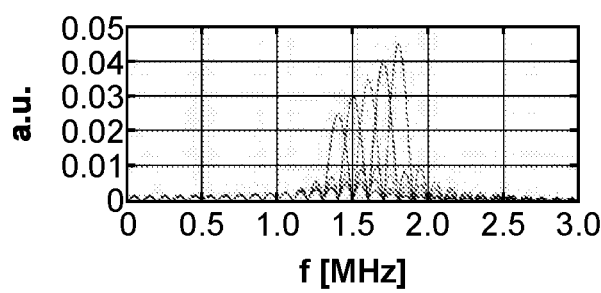
Figure 7B:
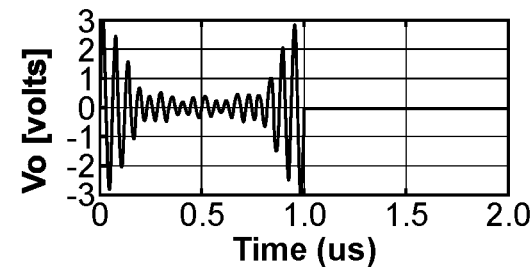
Figure 7B:
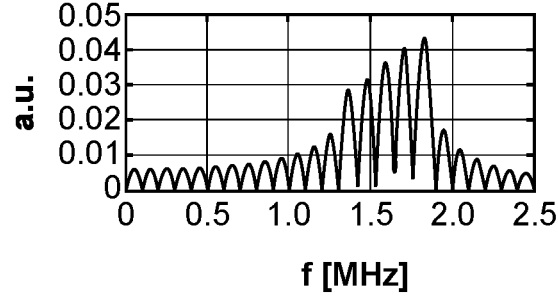

In another implementation, direct digital synthesizer (DDS) 98, diagrammed in FIG. 7, may be provided as a multi-channel DDS system to generate a simultaneous pre-defined number of discrete frequencies belonging to the estimated operational bandwidth of the paired RC-WVM implant 12 as shown in FIGS. 7A and 7B. The magnitude of each frequency component thus may be independently controlled to provide the optimum excitation to a specific RC-WVM implant 12 based on its individual coil characteristics. Additionally, the relative amplitude of each frequency component can be independently controlled to provide optimum excitation to the implant, i.e., the amplitude of the frequency component is selected in such a way that in the worst case for the paired implant to transmit a response signal (i.e., most compressed) the excitation signal is maximized. In this arrangement all outputs from the multi-channel DDS system 98 are summed together using summing amplifier 120 based on a high speed operational amplifier as shown in FIG. 7.

Figure 8:
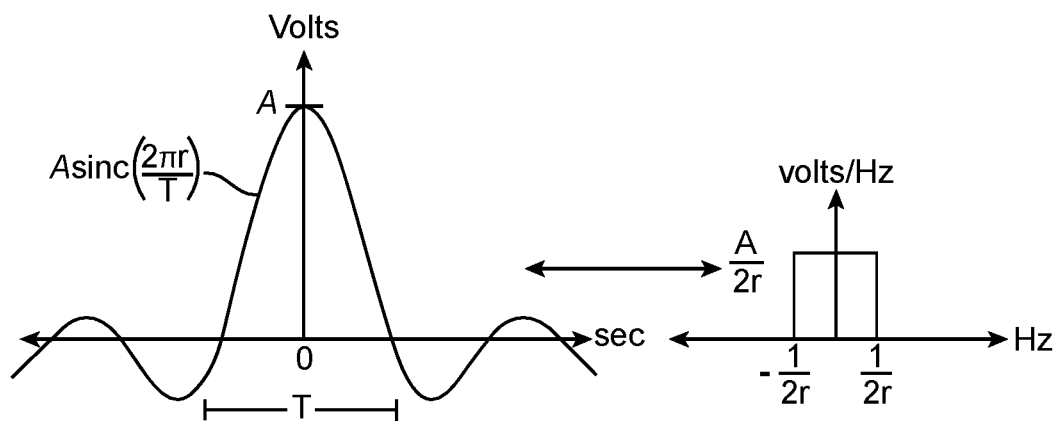
FIG. 8 illustrates waveform pulse shaping.

In yet another implementation, signal generator module 20a can be configured to provide pulse shaping as illustrated in FIG. 8. Arbitrary waveform generation based on direct digital synthesis 98 is employed to create a pulse of a predefined shape, the spectrum of which is optimized in order to maximize the response of the paired RC-WVM implant 12. The magnitude of the frequency components that result in decreased ring back signal amplitude is maximized while the magnitude of the frequency components that result in increased ring back signal amplitude is reduced, in order to obtain an approximately constant output signal amplitude and thus improved response from RC-WVM implant 12.

Referring again to FIG. 4, receiver-module 20b, in addition to tuning-matching circuit 96, includes components, e.g., single end input to differential output circuit (SE to DIFF) 106, variable gain amplifier (VGA) 108, filter amplifier 110 and output filters 112, for implant response detection, data conversion and acquisition for signal analysis. During the receive period, the T/R switch 92 connects the antenna belt 16b to the receiver-amplifier 20b, via the tuning and matching network 96. The response signal induced by the implant 12 in the antenna belt 16b is applied to a unity-gain single ended to differential amplifier 106. Converting from single-ended to differential mode contributes to eliminate common mode noise from the implant response signal. Since the amplitude of the implant response signal is in the microvolts range, the signal is fed, following conversion from single-ended to differential, into a variable gain differential amplifier 108 that is able to provide up to 80 dB (10000 times) voltage gain. The amplified signal is then applied to a active band-pass filter-amplifier 110 to eliminate out-of-band frequency components and provide an additional level of amplification. The resulting signal is applied to passive, high-order low pass filters 112 for further elimination of out-of-band high frequency components. The output of the filter is fed into the data conversion and communications module 22. The data conversion and communications module 22 includes components to provide data acquisition and transfer from the electronic system to the external processing unit. A high-speed analog-to-digital converter (ADC) 114 converts the output signal of the receiver module 20b into a digital signal of a predefined number of bits (e.g., 12 bits). This digital signal is transferred in parallel mode to microcontroller 116. In one implementation, a level shifter circuit is used to match the logic levels of the ADC to the microcontroller. The data outputted by the ADC is sequentially stored in internal flash memory of the microcontroller. To maximize the data throughput, direct memory access (DMA) is used in this process. Microcontroller 116 is synced with the direct digital synthesizer 98, so data acquisition starts when an RF burst is transmitted for excitation of implant 12. Once triggered, the microcontroller captures a predefined number of samples (e.g. 1024). The number of samples multiplied by the sampling period defines the observation window over which the response signal from implant 12 is assessed. This observation window is matched to the length of the response signal from implant 12, which depends on the time constant of the signal decay.

As a means of noise reduction, the response signal of the implant 12 is observed a predefined number of times (e.g., 256), and the average response is then computed. This approach greatly contributes to increasing the signal-to-noise ratio of the detected signal.

The average response is then transmitted to an external interface device 18 (e.g., laptop computer) by means of communications module 118. Different approaches can be taken for this. In one embodiment, the communication is performed using the UART interface from the microcontroller and external hardware is employed to convert from UART to USB. In a second embodiment, a microcontroller with USB driving capabilities is employed, and in this case connection with the external interface device is achieved by simply using a USB cable. In yet another implementation, the communication between the microcontroller and the external interface device is wireless (e.g. via Bluetooth).

The system is to be powered by a low voltage power supply unit (PSU), consisting of a AC-DC converter with insulation between mains input and output providing a minimum of 2 Means of Patient Protection (MOPP) as per Clause 8 of IEC 60601-1:2005+AMD1:2012. In this way, the power supply provides protection from electrocution to the user. The PSU is able to accommodate a wide range of mains voltages (e.g., from 90 to 264 VAC) and mains frequencies (e.g., 47 to 63 Hz) to allow operation of the system in different countries with different mains specifications.

Control system 14a as described above utilizes a software-based frequency detection. Thus, in terms of signal transmission, once the excitation frequency is optimized, system 10 employing control system 14a with signal generator module 20a operates in open loop mode, i.e., frequency or frequencies and amplitude of the transmit signal are not affected by RC-WVM implant 12 response. On the receive side, using amplifier-receiver module 20b, control system 14a detects the response signal from RC-WVM implant 12 and such signal is digitized using a high-speed data converter. The raw digitized data is subsequently transferred to a processing unit (e.g., laptop computer or other equipment microcontroller) and digital signal analysis techniques (e.g. Fast Fourier Transform) are applied to establish the frequency content of the signal. Thus, one advantage of using these software-based techniques is that phased-lock loop (PLL) circuits or similar circuits are not used or required in control system 14a.

Figure 9A:
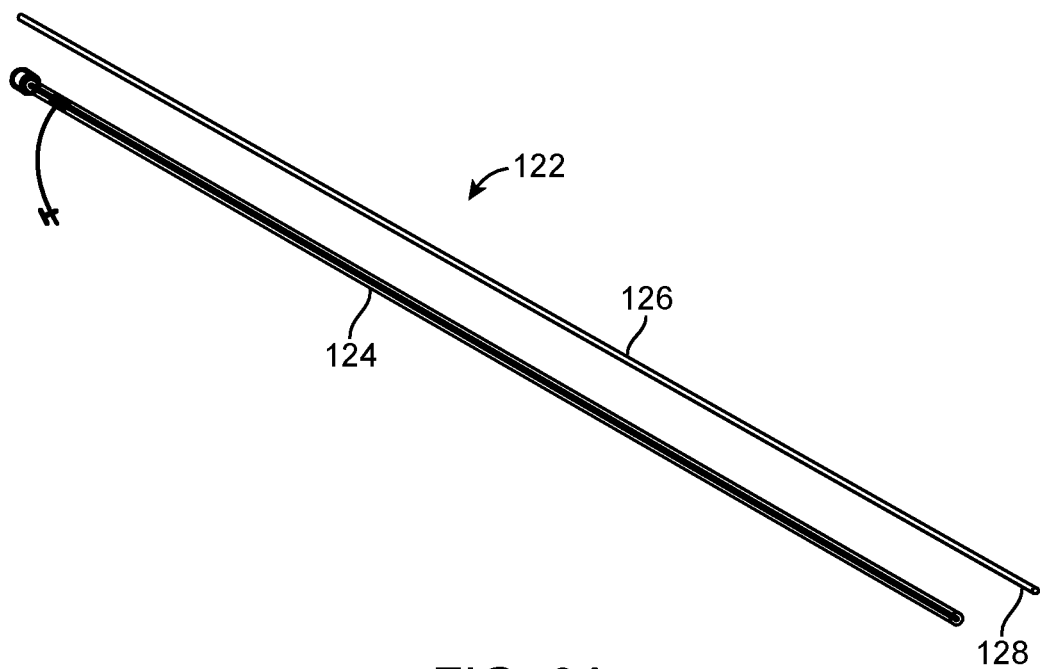
Figure 9B:
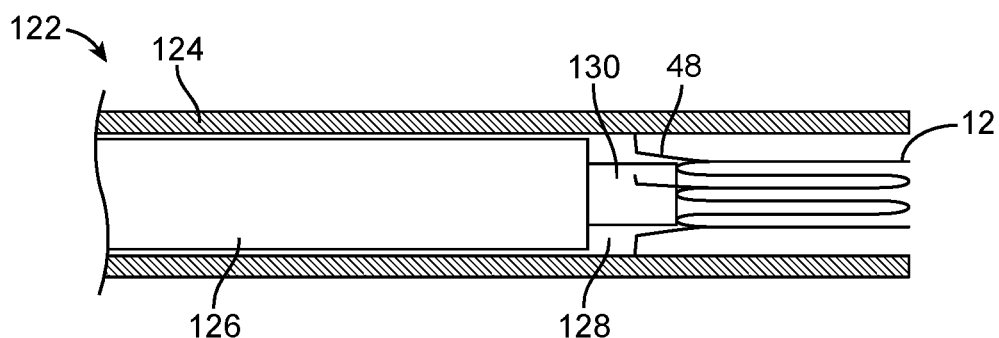
Figure 9C:
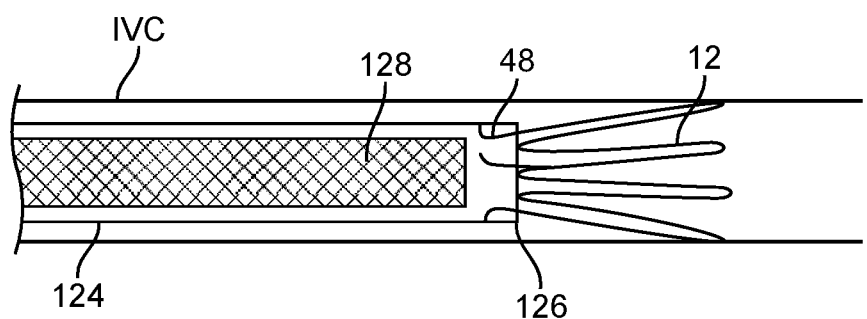

A further component of the overall RC-WVM system as described herein is the RC-WVM implant delivery system. FIGS. 9A-C illustrate aspects of an intravascular delivery system for placing RC-WVM implants 12 at a desired monitoring location within the IVC, which may generally comprise delivery catheter 122 including outer sheath 124 and pusher 126 configured to be received in the lumen of outer sheath 124. In general, insertion of devices into the circulatory system of a human or other animal is well known in the art and so is not described in detail herein. Those of ordinary skill in the art will understand after reading this disclosure in its entirety that RC-WVM implants 12 can be delivered to a desired location in the circulatory system using, e.g., a loading tool to load a sterile RC-WVM implant into a sterile delivery system, which may be used to deliver an RC-WVM implant to the IVC via a femoral vein or other peripheral vascular access point, although other methods may be used. Typically RC-WVM implant 12 will be implanted using a delivery catheter, delivery catheter 122 being an illustrative example thereof, and the RC-WVM implant will be optimized for delivery through as small a catheter as possible. To facilitate this, bends at the implant crowns (or ears as later described, collectively "sensor construct end portions") may be small-radius bends to facilitate a low profile when packed into the delivery catheter as shown, for example in FIG. 9B. In one alternative, pusher 126 may be provided with a stepped distal end 128 having a reduced diameter end portion 130 configured to engage the inner perimeter of RC-WVM implant 12 when compressed for delivery. For implant embodiments employing anchors (e.g., anchors 48 in FIG. 2), end portion 130 may be configured to engage an inner perimeter defined by the anchors in the compressed configuration as illustrated in FIG. 9B. Alternatively, pusher distal end 128 may be provided with a straight, flat end or other end shape configured to cooperate with a specific RC-WVM implant and anchor design.

In one deployment option, a RC-WVM implant may be inserted from a peripheral vein such as the femoral or iliac vein into the IVC to be positioned at a monitoring location between the hepatic and renal veins. It will be understood that the implant also may be introduced from other venous locations. Depending on implant configuration, when placed in the IVC for fluid status monitoring, specific orientation of RC-WVM implant 12 may be required to optimize communication with the belt reader antenna coil. To facilitate desired placement or positioning, the length and diameter of RC-WVM implant 12 may be designed so that it gradually expands as it is held in position with the pusher 126 and the sheath 124 is withdrawn, as schematically illustrated in FIG. 9C. Here, RC-WVM implant 12 is shown partially deployed with the distal crowns already engaging the IVC wall while the proximal crowns are still contained within sheath 124.

Such a gradual, partial deployment helps ensure that RC-WVM implant 12 is properly positioned in the IVC. The sensor length to vessel diameter ratio (where the length is always greater than the vessel diameter) is also an important design factor to ensure that the sensor deploys in the correct orientation in the IVC. In a further alternative, distal end 128 of pusher 126 may be configured to releasably retain the anchors or a proximally oriented portion of the implant before it is fully deployed from outer sheath 124 so that it may be retracted for repositioning as needed. For example, small, radially extending studs may be provided near the end of end portion 130, which engage behind the proximal crowns of implant 12 so long as it is compressed within outer sheath 124 whereby the implant may be pulled back in from a partially deployed position as shown in FIG. 9C, but self-releases from the studs by expansion when fully deployed after positioning is confirmed. Conventional radiopaque markers may be provided at or near the distal ends of outer sheath 124 and/or pusher 126, as well as on RC-WVM implant 12 to facilitate visualization during positioning and deployment of the implant. Typically, where anchor features are employed, the implant will be positioned with the anchor features proximally oriented so the anchors are the last portion deployed in order to facilitate correct orientation within the IVC and potentially allow for pull back and repositioning as may be needed. Once the implant is fully deployed, delivery catheter 122 may be withdrawn from the patient, leaving implant 12 as a discrete, self-contained unit in the vessel without attached wires, leads, or other structures extending away from the monitoring location.

Example 1

Figure 4:
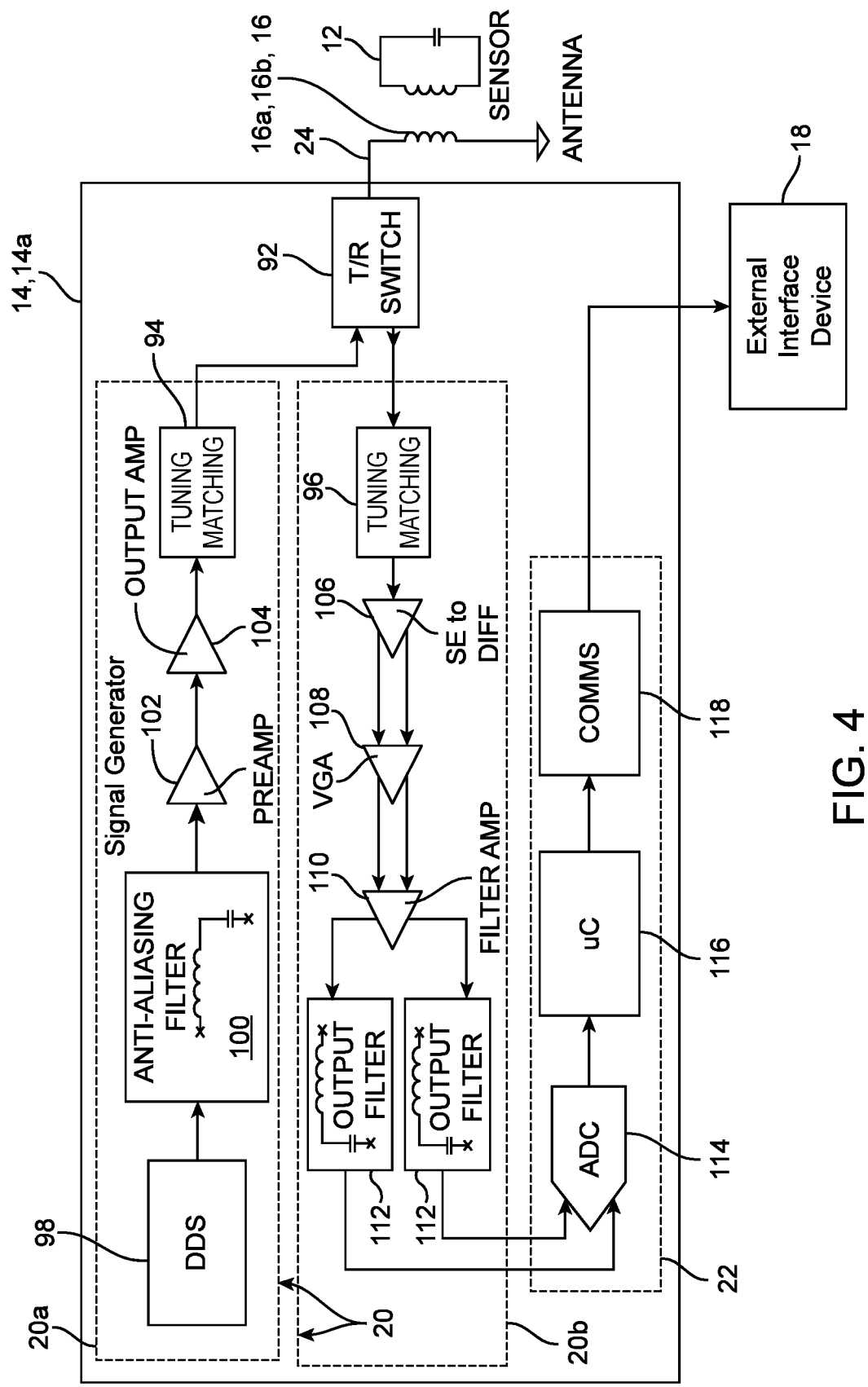
FIG. 4 is a block diagram illustrating an embodiment of system electronics.

Systems as described herein have been evaluated in pre-clinical testing using RC-WVM implant 12a (as in FIG. 2), an antenna belt similar to antenna belt 16b (as in FIG. 3) and control system 14a (as in FIG. 4). The implants were deployed into ovine IVCs using delivery systems 130 (as in FIG. 9B) using standard interventional techniques. Deployment was confirmed angiographically, using intravascular ultrasound and using the antenna belt.

Figure 10A:
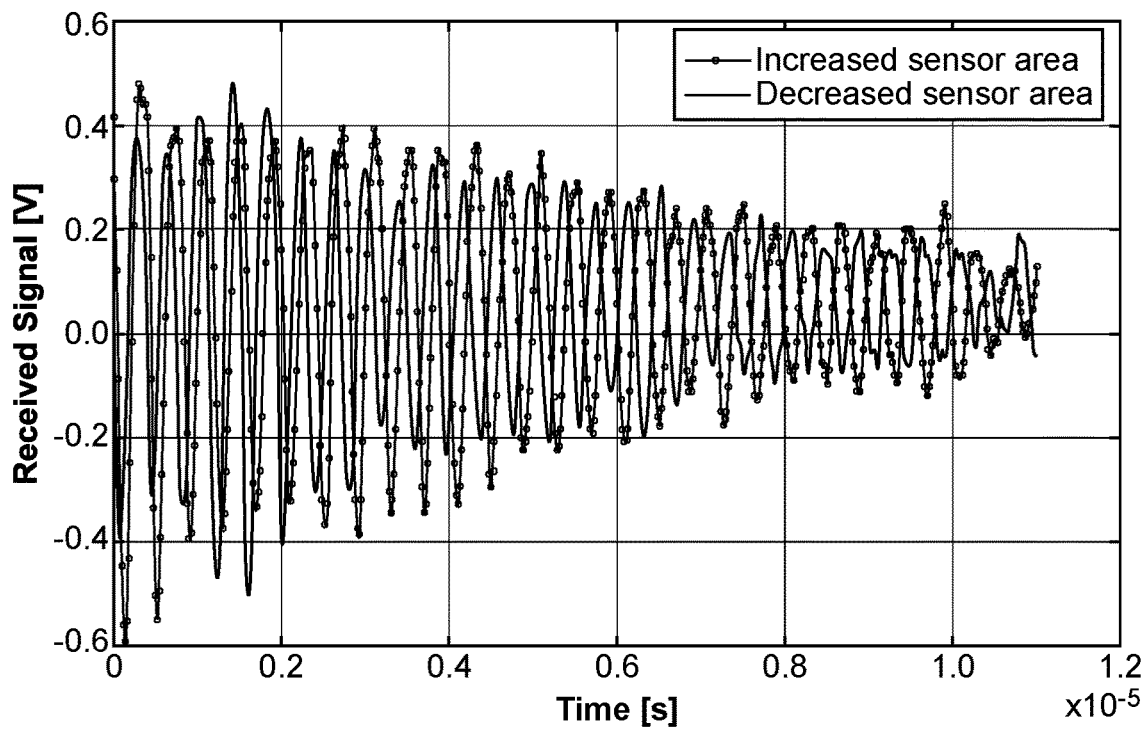
FIGS. 10A, 10B, 10C, 10D and 10E illustrate signals obtained in pre-clinical experiments using a prototype system and an RC-WVM implant as shown in FIGS. 1 and 2.
Figure 10B:
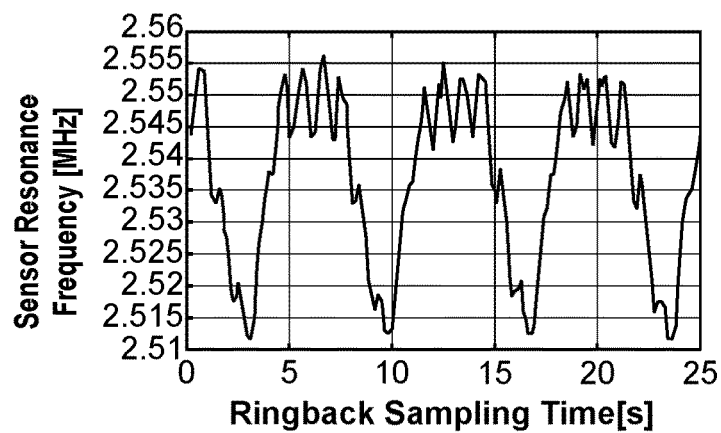
Figure 10C:
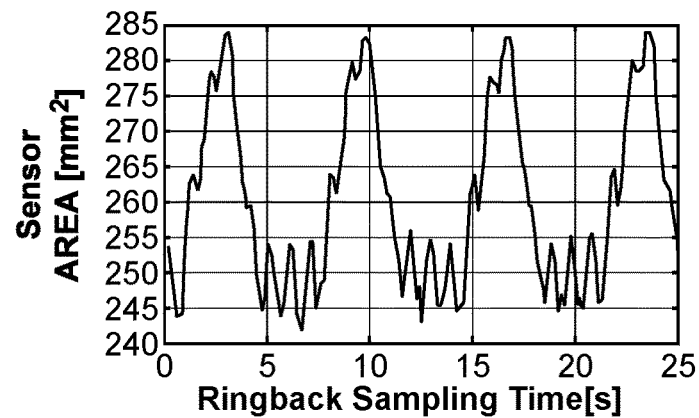

FIGS. 10A, 10B and 10C illustrate, respectively, the raw ring down signal, detection of the maximum frequency and conversion of this to an IVC area using a reference characterization curve. FIG. 10A shows the raw ring down signal in the time domain with the resonant response of the RC-WVM implant decaying over time. Modulation of the implant geometry results in a change in the resonant frequency which can be seen as the difference between the two different plotted traces. FIG. 10B shows the RC-WVM implant signal as converted into the frequency domain and plotted over time. The maximum frequency from FIG. 10A is determined (e.g., using fast Fourier transform) and plotted over time. The larger, slower modulation of the signal (i.e., the three broad peaks) indicate the respiration-induced motion of the IVC wall, while the faster, smaller modulation overlaid on this signal indicate motion of the IVC wall in response to the cardiac cycle. FIG. 10C shows the frequency modulation plotted in FIG. 10A converted to an IVC area versus time plot. (Conversion in this case was based on a characterization curve, which as determined through bench testing on a range of sample diameter lumens following standard lab/testing procedures.) FIG. 10C thus shows variations in IVC area at the monitoring location in response to the respiration and cardiac cycles.

Figure 10D:
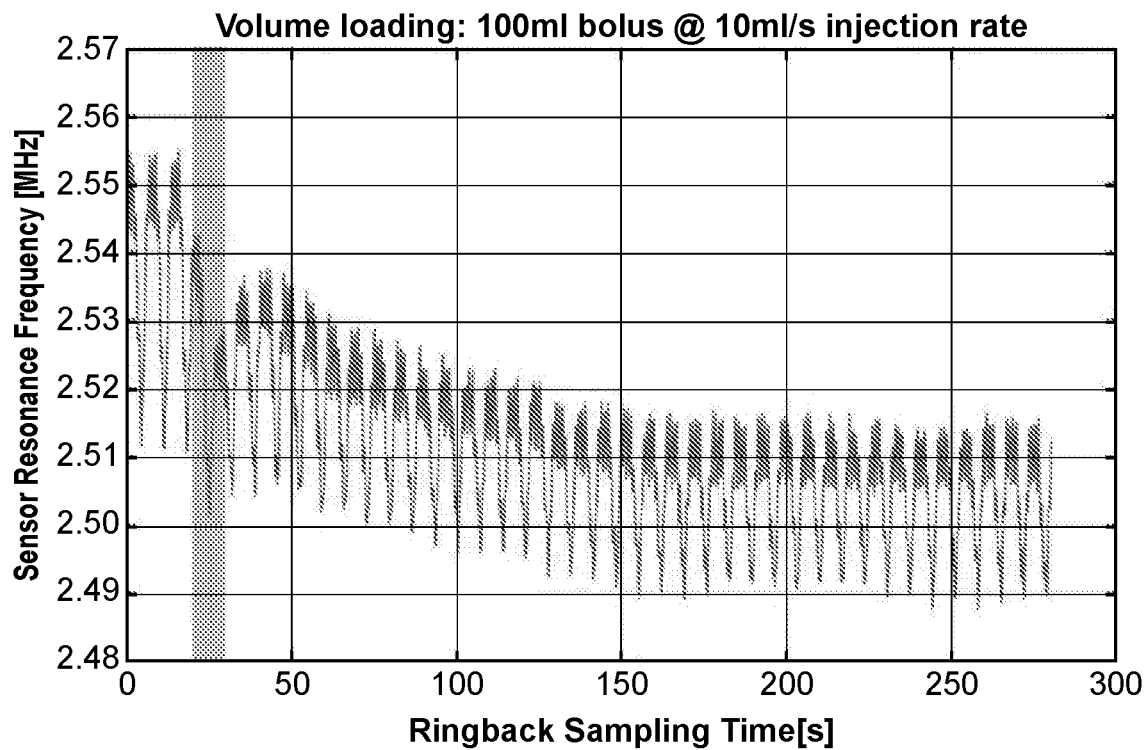
Figure 10E:
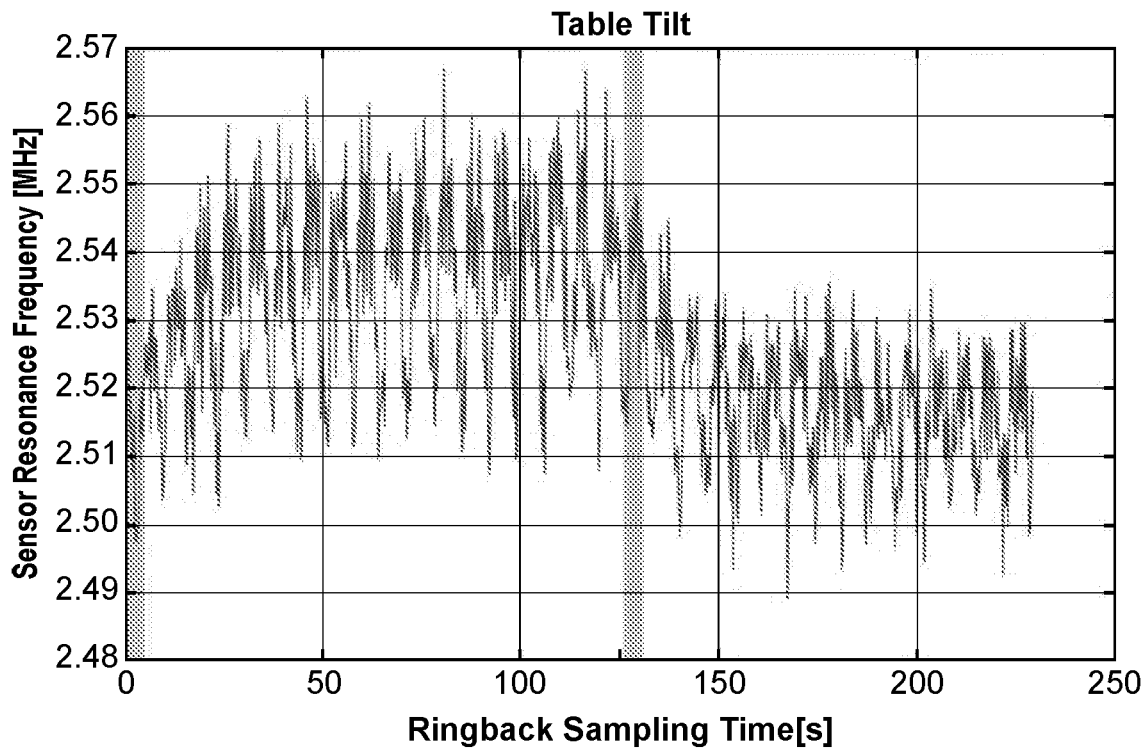

The ability of RC-WVM implant 12 (in this case, implant 12a) to detect IVC area changes as a result of fluid loading is demonstrated in FIGS. 10D and 10E. In one example, the results of which are shown in FIG. 10D, after placement of RC-WVM implant 12 in the ovine IVC and confirmation of receipt of the implant signal, a fluid bolus of 100 ml at 10 ml/s was added to the animal. The grey band in FIG. 10D indicates the administration of the fluid bolus. As reflected by the decreasing frequency ring-back signal from RC-WVM implant 12, the added fluid volume caused the IVC to expand, and with it the implant, which in turn causes a change in the inductance of the implant thus changing the frequency of its ring-back response to excitation. In another example, with results shown in FIG. 10E, the operating table was tilted to shift fluid within the animal. Starting from the left in FIG. 10E, the first grey band indicates the time when the table was initially tilted. Tilting of the table caused fluid to shift away from the IVC, causing the IVC to reduce in diameter, and thus increasing the frequency of the ring-back signal of RC-WVM implant 12 as it moved to a smaller diameter with the IVC. The second grey band indicates the time when the table was returned from tilted to flat. At this point, fluid shifts back into the IVC, causing it to increase in size with the added fluid volume and thus reduce the frequency of the ring-back signal as explained above.

These output signals thus demonstrate the detection of modulation of the IVC with respiration. In particular, it will be appreciated that embodiments of the present invention can thus provide an unexpectedly powerful diagnostic tool, not only capable of identifying gross trends in IVC geometry variations, but also capable of discriminating in real-time between changes in IVC geometry arising from respiration and cardiac function.

Alternative Patient Care Systems Based on RC-WVM Implants Disclosed Herein

Figure 11A:
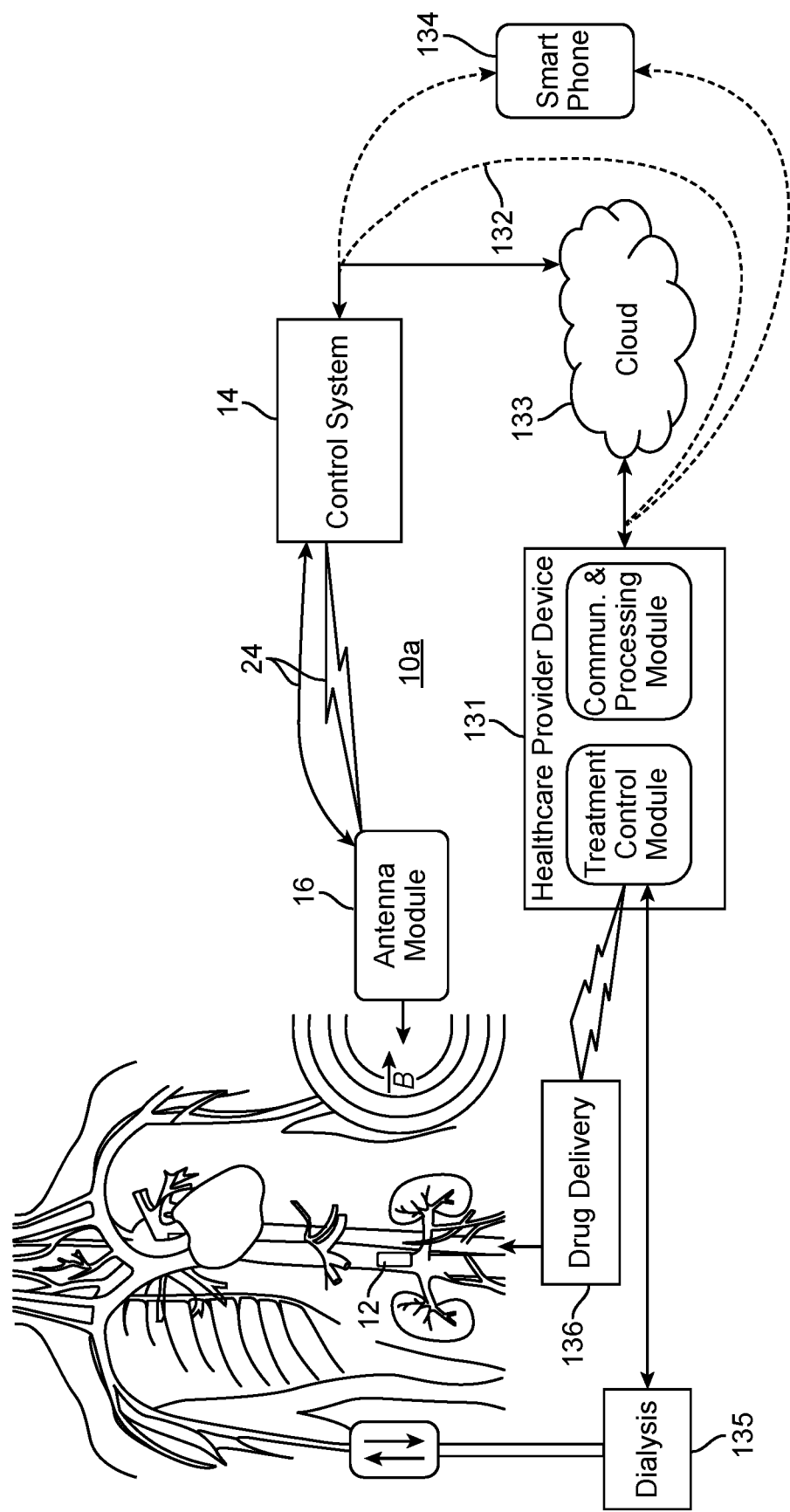
FIGS. 11A and 11B schematically depict components and possible arrangements of alternative clinical or home systems employing RC-WVM implants and control systems as disclosed herein.

FIG. 11A schematically illustrates an alternative system 10a configured to provide patient care based on fluid status monitoring using an RC-WVM implant 12 positioned at a monitoring location in the IVC as elsewhere described herein. Using RC-WVM implant 12, measurements of IVC diameter or area by implant 12 may be made continuously over one or more respiratory cycles to determine the variation in patient fluid volume over this cycle. Further, these measurement periods may be taken continuously, at preselected periods and/or in response to a remotely provided prompt from a health care provider/patient.

Antenna module 16 may be configured to communicate via wireless or wired connection 24 with control system 14, as elsewhere described herein. Data and information collected by control system 14 may be communicated ultimately to a healthcare provider device 131 via hard wired links such as telephone or local area networks 132 or through Internet or cloud-based systems 133. Personal communication devices 134, such as smart phones or tablets, also may be used for communication with, or as alternatives to, other communications devices and modes described herein. Healthcare provider device 131 may be configured with an appropriate user interface, processing and communications modules for data input and handling, communications and processing, as well as treatment and control modules, which may include treatment algorithms as described herein for determining treatment protocols based on collected IVC diameter or area measurements, and systems for automated remote control of treatment devices based on determined treatment protocols as elsewhere described herein. Examples of such treatment devices include, but are not limited to, dialysis machine 135 and drug delivery devices 136. Examples of treatments include, when measured dimensions fall within the hypovolemic warning zone, administration of fluids or vaso-constricting drugs, and when measured dimensions fall within the hypervolemic warning zone, dialysis or administration of diuretics or vasodilating drugs.

IVC physical dimension data and/or fluid volume state information derived therefrom may also be communicated directly to the patient themselves, along with therapy advice based on this data and using pre-determined algorithms/ implanted medical devices. Communications protocols throughout the system may include bidirectional communications to permit a healthcare provider (or other appropriately trained operator at another point in the system) to alter overall monitoring protocols executed at the monitoring device or, for example, to request additional queries by the monitoring device outside the current operational protocol.

Other embodiments include systems for patient self-directed therapy, for example with IVC volume metrics data utilized directly by the patient with or without clinician overview, e.g., for self-administration of drugs or other therapies. Such systems may also be implemented for home dialysis and/or peritoneal dialysis. Wireless communication between the IVC monitor and the patient's or healthcare provider's cell phone or computer would allow continuous or periodic transmission of IVC data and the use of software applications to provide alarms or reminders, graphically present trends, suggest patient actions, drug dosage options, or treatment system settings, and allow communication with physicians.

Figure 11B:
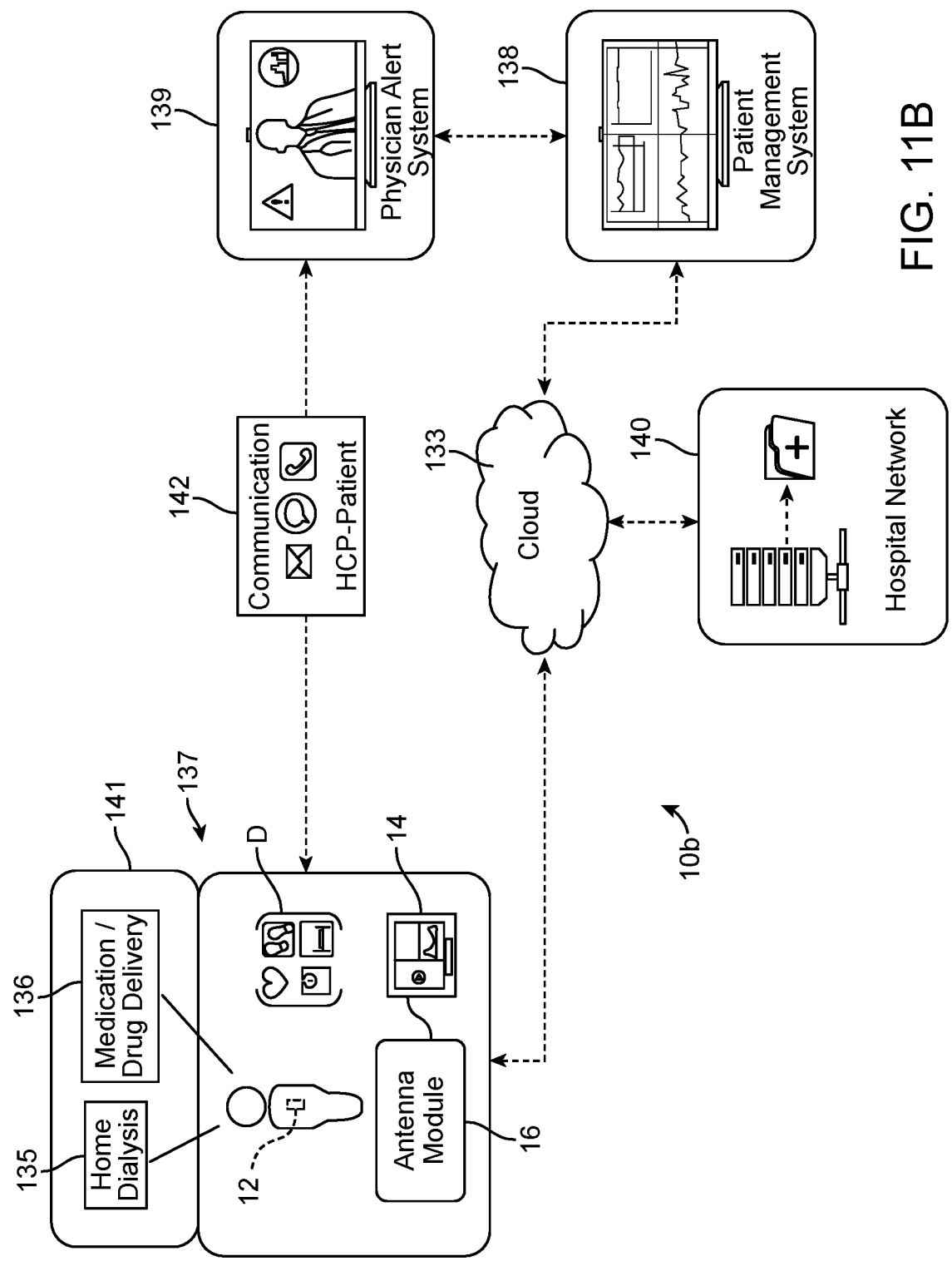

FIG. 11B schematically illustrates another exemplary system, which may, in one alternative, incorporate patient self-directed therapy. As shown in FIG. 11B, system 10b provides for communication between the patient home system 137, cloud storage 133, a patient management system 138, a physician alert system 139, and optionally a hospital network 140. Data transmission from the patient home system 137 to the cloud 133 for storage and access facilitates remote access for clinical and nursing teams. In patient self-directed therapy embodiments, patient's home may include home therapy devices 141, which may independently access cloud storage 133, and based on predetermined limits/treatment algorithms, indicate patient self-administration of medications or drug delivery 136 or home dialysis machines 135. In such a system a patient with wireless implant 12 may receive prompts from a cell phone or other device in the home at specific time intervals or may utilize data (D) generated by other patient monitoring devices such as blood pressure, heart rate or respiration monitors that also communicate with the home device as inputs to decision-making algorithms, and may transmit data to cloud 133 for storage. System 10b may also include communication links (direct, networked or cloud-based) with such other monitoring devices to receive data (D) inputs used in setting warning zones and alert limits and assessing patient fluid state. Further inputs may be made by a user through a user interface, which may be, for example, configured as part of patient management system 138. User inputs may include additional patient-specific information such as patient age, sex, height, weight, activity level, or health history indicators.

In response to a prompt from system 10b to take a reading, the patient would position him/herself with respect to or on antenna module 16 as appropriate to communicate with selected RC-WVM 12. A user interface of control system 14, or, in one possible alternative, personal communication device 134 may provide sequential prompts and/or instructions to the patient.

Varying levels of response may be generated by home system 137 depending on IVC measurements received from RC-WVM implant 12 and as may be interpreted in light of other patient data (D). Minimal responses may be provided if the patient fluid status is within acceptable ranges and no action is required. Mid-level responses may include warnings or to contact healthcare providers or prompts for medication administration or changes in home drug delivery, or home dialysis. Consistently out-of-range or increasing readings would prompt response escalation to clinical intervention. Patient treatment protocols, in general, may be based on the applicable standards of care for disease state management as informed by diagnostic information reported by RC-WVM implant 12 and system 10. Specific examples of treatment protocols designed to take advantage of the unique capabilities of RC-WVM implant 12 are provided in Applicant's co-pending international application no. PCT/US2017/046204, filed Aug. 10, 2017, entitled "Systems And Methods For Patient Fluid Management", which is incorporated by reference herein. When home dialysis or drug delivery is prompted, it may be controlled directly in a closed-loop system as described above or may be controlled by the patient with prompts from the system. Patient data (D) and IVC measurements from RC-WVM implant 12 also may be communicated continuously or periodically by system 10b to cloud storage 133 and further communicated to a remote patient management system 138. Functionality for system 10b may be largely contained in home system 137 or in patient management system 138 or appropriately distributed across the network. Optionally, patient-related data including sensor results and patient health and fluid states also may be communicated to or accessible by a hospital network 140. System 10b also may receive patient-related data, including for example, medical records related to past therapies and medical history.

When a patient condition is recognized by system 10b as outside acceptable limits, an alert may be generated by physician alert system 139. Information supporting the alert condition may be communicated, for example, through patient management system 138 to physician alert system 139. Physician alert system 139 may reside at a healthcare provider office and/or may include a mobile link accessible by the healthcare provider remotely to permit communication 142 between the healthcare provider and the patient. Communication 142 between healthcare provider and patient may be network, Internet or telephone-based and may include email, SMS (text) messaging or telephone/voice communication. Physician alert system 139 allows the healthcare provider to review logs of IVC measurements and medication changes over time and make decisions regarding therapy titration, and in critical cases, hospital admissions, remote from the patient.

Exemplary system embodiments 10a and 10b are each illustrated, respectively, in FIGS. 11A and 11B with various system functions assigned to particular functional elements of the systems. For the sake of clarity of the disclosure, not all possible distributions or combinations of functions in functional elements across the system are described. As will be appreciated by persons of ordinary skill, other than the function of the RC-WVM implant itself, all functions may be distributed among functional elements in any number of arrangements as best suited to a home or clinical application and the intended location of sensor reading function, e.g., in a home or hospital setting. For example, all system functions (except implant-specific functions as mentioned) may be contained in a single functional unit in the form of a stand-alone patient management system. Alternatively, functions may be highly distributed among mobile devices networked with secure cloud computing solutions. For example, control system 14 may communicate directly with a patient-owned smart phone to receive signals indicating IVC physical dimension measurements and, in turn, transmit those signals via WiFi or cell network to the cloud for distribution to further mobile devices in the possession of healthcare providers. Hand-held devices 134, such as tablets or smart phones, may communicate directly with controlled-treatment delivery devices, or such devices may be controlled by a self-contained patient management system. Further, processing necessary for operation of the system also may be distributed or centralized as appropriate, or may be duplicated in multiple devices to provide safety and redundancy. Thus, the specific arrangement of the functional elements (blocks) in the schematic presentations of the illustrative examples in FIGS. 11A and 11B are not to be considered as limiting with respect to possible arrangements for distribution of disclosed functions across a network.

As mentioned above, various care algorithms may be developed based on systems 10a and 10b. For example, in one scenario, a first, home-care algorithm governs interactions in the home system including periodic IVC diameter/area measurements using RC-WVM implant 12 and dictates whether to maintain current therapies or to change therapies within the scope of home-care team capabilities. As long as IVC volume metrics stay within predefined limits, the first, home-care algorithm continues to govern monitoring and treatment. However, if monitored parameters, for example IVC volume metrics, exceed the predefined limits, then an alert is generated that engages a second, healthcare-provider algorithm. Such an alert may be generated internally by home system 137, or may be generated in patient management system 138 (or physician alert system 139) based on monitored data communicated by home system 137 and received by the other systems either periodically or on a continuous basis. In one embodiment, an alert is received initially by a physician's assistant or heart failure nurse who can triage the situation through patient management system 138 locally or remotely. At this initial level the assistant or nurse may elect to generate a message for communication 142 to the patient through the network related to modulation of therapy or other parameters such as level of physical activity. However, if triage indicates the alert to represent a more critical event, the physician may be alerted through physician alert system 139. Multiple layers of care and review based on measured IVC volume metrics are thus provided to efficiently manage patient fluid status and where possible avoid hospitalizations.

RC-WVM Implant Design Considerations and Alternative Implant Embodiments

It will be appreciated that the measurement of dimensional changes in the IVC presents unique considerations and requirements arising from the unique anatomy of the IVC. For example, the IVC is a relatively low pressure, thin-walled vessel, which changes not simply its diameter, but its overall shape (cross-sectional profile) in correspondence to blood volume and pressure changes. Rather than dilating and constricting symmetrically around its circumference, the IVC expands and collapses primarily in the anterior-posterior direction, going from a relatively circular cross-section at higher volumes to a flattened oval-shaped cross-section at lower volumes. Thus embodiments of RC-WVM implants 12 must monitor this asymmetrical, low-pressure collapse and expansion in the A-P direction without excessive radial constraint, yet must also engage the vessel walls with sufficient force to anchor the implant securely and prevent migration. Accordingly, RC-WVM implant 12 must be capable of collapsing with the vessel in the A-P direction from a generally circular cross-section to an oval or flattened cross-section without excessive distortion of the vessel's natural shape. These requirements are achieved according to various embodiments described herein by appropriate selection of material compliance and configuration such that the coil measurement section of RC-WVM implant 12 is maintained in contact against the IVC wall without undue radial pressure that may cause distortion thereof. For example, RC-WVM implants 12 according to embodiments described herein may exert a radial force in the range of about 0.05N-0.3N at 50% compression. In another alternative, potentially increased security of positioning may be achieved without compromising measurement response by physically separating anchoring and measurement sections so as to move possible distortions of the vessel wall due to anchoring a sufficient distance spaced from the measurement section so as not to affect measurements.

RC-WVM implants 12 as described may be configured in various structures such as collapsible loops or tubes of formed wire with resilient sinusoidal or "Z-shaped" bends, or as more complex collapsible shapes with more resilient regions such as "spines" joined by relatively less resilient regions such as "ears." Each structure is configured based on size, shape and materials to maintain its position and orientation through biasing between resilient elements of the implant to ensure contact with the vessel walls. Additionally or alternatively, anchors, surface textures, barbs, scales, pin-like spikes or other securement means may be placed on the structure to more securely engage the vessel wall. Coatings or coverings also may be used to encourage tissue in-growth. In some embodiments it may be preferable to configure specific portions of the structure, for example the coil spines, as the position-maintaining engagement portion in order to reduce any effect of the biasing force on movement of the vessel walls as sensed at the coil ears, or vice-versa. In yet other embodiments, separate anchoring structures may be coupled to a coil-measurement portion of the implant. Such anchoring structures may comprise hooks, expandable tubular elements, or other tissue-engaging elements which engage the vessel upstream or downstream of the coil portion so as to minimize any interference with the natural expansion or contraction of the vessel in the area of the coil itself. Sensing modalities and positioning is described in more detail below.

When RC-WVM implant 12 is energized it must generate a signal of sufficient strength to be received wirelessly by an external system. In the case of a variable induction circuit, the coil which transmits the signal to the external receiver must maintain a tubular shape or central antenna orifice of sufficient size, even when the vessel is collapsed, such that its inductance is sufficient to generate a field strong enough to be detected by an external antenna. Thus, in some embodiments, it may be desirable that the variable inductor have a collapsing portion which deforms with the expansion and collapse of the vessel, and a non-collapsing portion which deforms relatively little as the vessel collapses and expands. In this way, a substantial portion of the coil remains open even when the vessel is collapsed. In other embodiments, the coil may be configured to deform in a first plane containing the anterior-posterior axis while deflecting relatively little in a second orthogonal plane containing the medial-lateral axis. In still other embodiments, a first inductive coil may be provided to expand and collapse with the vessel, and a separate transmit coil, which deforms substantially less, provided to transmit the signal to the external receiver. In some cases the transmit coil also may be used as an anchoring portion of the implant.

Figure 12A:
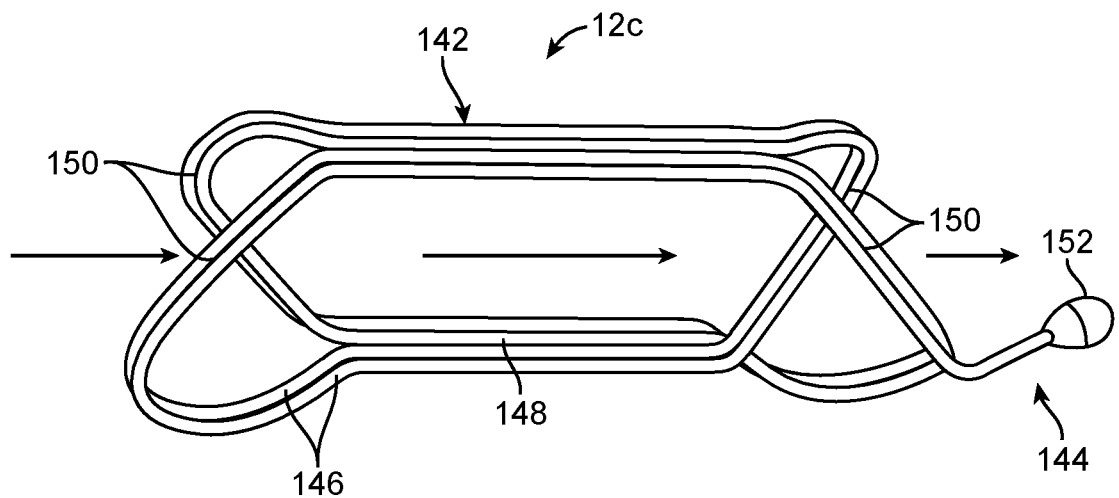

Turning to specific alternative RC-WVM implant embodiments disclosed herein, a first exemplary alternative embodiment is RC-WVM implant 12c, shown in FIG. 12A. Implant 12c may comprise a "dog-bone-like" shape as shown with coil portion 142 and capacitor portion 144. Implant 12c may comprise an electrically conductive wire or bundle of wires that is wound or otherwise formed into a single continuous coil comprising multiple turns or loops having an oval or rounded rectangular shape. It may be advantageous to use "Litz" wire, which has multiple independently insulated strands of wire, for the coil, since that may enhance the inductance of the implant. The coil is configured to be oriented such that the longer dimension of the generally rectangular loops extend longitudinally in a cranial-caudal direction within the IVC. The wire or group of wires may be wound multiple times in a continuous overlapping manner such that the rectangular loops each are defined by two or more parallel strands or bundles of wire about their periphery. The rectangular loops have central regions bounded by two or more longitudinal wires 146 forming spines 148 approximately defining a central plane running longitudinally in a cranial-caudal direction. This central region is configured to be disposed in a plane generally perpendicular to the anterior-posterior axis of the vessel, and remains relatively un-deformed as the vessel collapses and expands in the anterior-posterior direction. The longitudinal elements may engage opposing walls of the vessel. At the caudal and cranial ends of the central regions of the rounded rectangles, the wire or wires form two lobes or a pair of coil ears 150 that flare outwardly away from each other and from the central plane of the implant in the anterior and posterior directions, as shown in FIG. 12A. Coil ears 150 are configured to engage opposing anterior and posterior walls of the vessel and to leave the central lumen of the vessel completely unobstructed for flow of blood as indicated by the arrows.

As the IVC changes shape, the longitudinal wires may move closer together or farther apart, and coil ears 150 may also move closer together or farther apart, thereby changing the inductance of the coil. The ears may be separated by about 1 cm to about 5 cm at the apex of the curved ends of the ears. RC-WVM implant 12c, as adapted for an average IVC size, may be about 2.5 cm to 10 cm long. It may be appreciated that as the IVC collapses in the anterior-posterior direction, coil ears 150 deform inwardly thereby changing the inductance of the coil. However, the central region of the coil remains relatively un-deformed and maintains sufficient size that the inductance of the coil is high enough to produce a field sufficiently strong for external detection. Capacitor portion 144 in this embodiment includes discrete capacitor 152 to complete the L-C circuit. Capacitor portion 144 may be alternatively located in a number of locations, such as distal to coil ears 150, or along one of spines 148.

As described above, the IVC in a typical monitoring region between the hepatic and renal veins is relatively compliant, and tends to collapse into a non-circular oval-shaped cross-section, which is wider in the medial-lateral direction than it is in the anterior-posterior direction. A feature of "dog-bone" style implant such as RC-WVM implant 12c is that spines 148 create more stiffness in the plane of the central region of the coil which causes the device to rotationally auto-orient around the longitudinal axis of the vessel with the two spines along the medial and lateral walls, and coil ears 150 flaring anteriorly and posteriorly. Typically, a RC-WVM implant 12 thusly configured will assume an unbiased implanted configuration in which the distance between the spines preferably corresponds to the natural medial-lateral dimension of the IVC at current blood volume such that the implant does not distort the vessel from its natural shape. In one alternative, overall the diameter of RC-WVM implant 12 may be somewhat oversized as compared to the vessel diameter at its secured location so it is always relatively biased outward against the vessel walls. In such a case, when the IVC collapses, the A-P dimension reduces and the M-L dimension increases, although the M-L increase is generally much less than the A-P collapse, the oversizing maintains vessel wall contact and secure positioning. As elsewhere discussed, resiliency of the coil/wires forming the implant must be selected in this case also so as to move with the vessel without distorting measurements based on vessel wall movement.

Figure 12B:
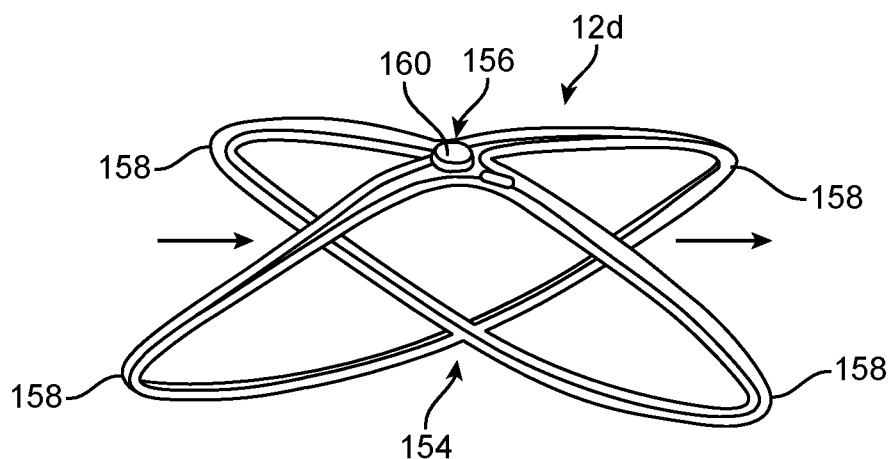

A further alternative embodiment of RC-WVM implant 12 is the "x-bow" shaped implant 12d, shown in FIG. 12B. Like "dog-bone"-shaped RC-WVM implant 12c, "x-bow"-shaped RC-WVM implant 12d may comprise an electrically conductive wire or group of wires of types previously described formed into coil portion 154 and capacitor portion 156. However, rather than being formed into a rounded rectangular shape as in RC-WVM implant 12c, "x-bow"-shaped RC-WVM implant 12d may be wound or otherwise formed into two ellipsoid shapes disposed in intersecting planes to form two sets of coil ears 158 as shown. In one implementation, an "x-bow"-shaped RC-WVM implant 12d may be formed by winding on a mandrel or otherwise forming an ellipsoid shape with one or more wires in a single plane and then bending one or more turns of the one or more wires out of that plane into an ellipsoid shape in another plane to form an overall shape like that illustrated in FIG. 12B. A capacitor element such as discrete capacitor 160 may be conveniently placed in capacitor portion 156 at one of the intersections of the "X" or at one of the ends of ears 158. An implant configured as RC-WVM implant 12d might preferably be placed in the IVC with coil ears 158 oriented as described above (against the anterior-posterior walls of the IVC). Blood flow through the open central lumen of the implant would follow the direction of the large arrows in FIG. 12B.

Similar to "dog-bone"-shaped RC-WVM implant 12c, "x-bow"-shaped RC-WVM implant 12d deforms with the vessel walls in the anterior-posterior direction while having relatively little deformation in the medial lateral direction. RC-WVM implant 12d is thus able to deform with the IVC as it collapses but retains an open coil shape in the medial-lateral direction to maintain a high level of inductance, thus being capable of producing a field of sufficient strength to be detected by an external receiver.

In other embodiments, a tether or stent-like structure may be used to anchor RC-WVM implant 12 in a predetermined location while allowing it to very gently press against the walls of the vessel desired to be monitored. An important issue that must be taken into consideration is the fact that implants in veins or arteries can modify the flexibility or resiliency of the vein or artery to the point that changes in the shape of the veins or arteries that may be expected to be measurable using such implants may not take place or may be severely attenuated due to the shape of, function of, or vascular response to the implant. Accordingly, it is important that the implant have sufficient stiffness to anchor itself in the vessel while simultaneously allowing natural expansion and contraction of the vessel walls at the location(s) where the implant is measuring vessel dimension. In the implants described above, for example, the wall-engaging ears of the coils must have sufficient compliance/flexibility and resilience to move in and out with the vessel walls without excessive distortion or attenuation of the natural wall motion.

Figure 12C:
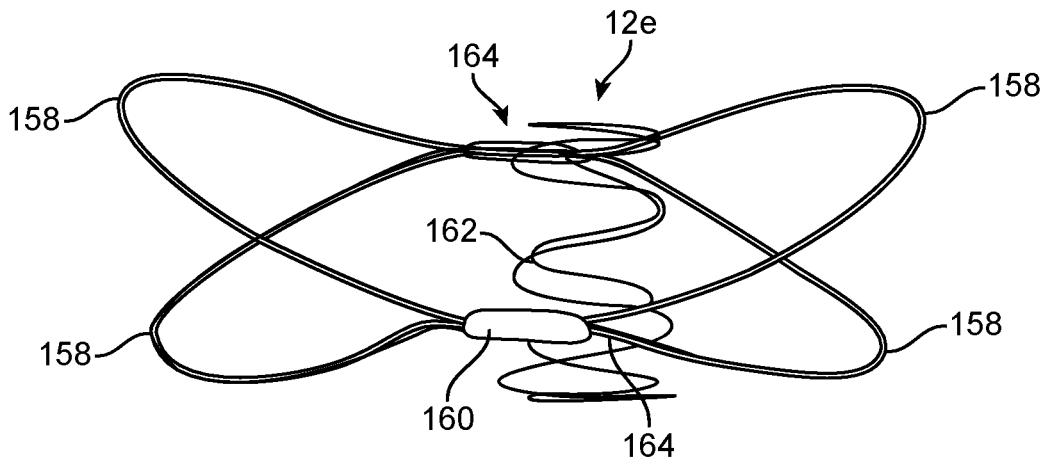

As shown in FIG. 12C, RC-WVM implant 12e is an example of an alternative implant embodiment employing a stent-like structure for additional stability or anchoring security. RC-WVM implant 12e is formed as an "x-bow" type implant similar to RC-WVM implant 12d, discussed above, but with added sinusoidal, expandable and collapsible wire support 162 around the center of the implant and secured at the opposed coil wire crossing points 164. Wire support is insulated from the coil wires forming coil ears 158 so as not to interfere with the electrical performance of the implant. As one example, wire support 162 may be formed of a nitinol wire or laser cut shape as used for the frame of the implant itself (see, e.g. frame 44 in FIGS. 2 and 2B or frames 244 or 246 in FIG. 20A or 20B, respectively). The stent-like structure of wire support 162 allows it to expand and collapse with the implant and assists in uniform expansion and localization of anchoring force away from coil ears 158.

Figure 13A:
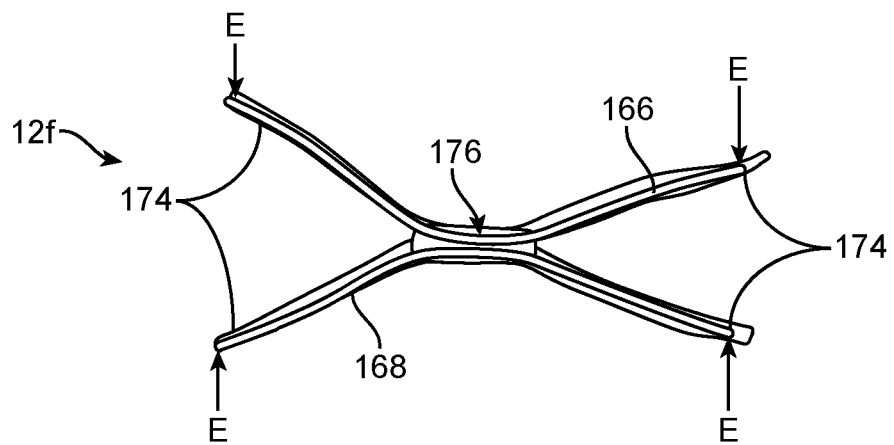
Figure 13B:
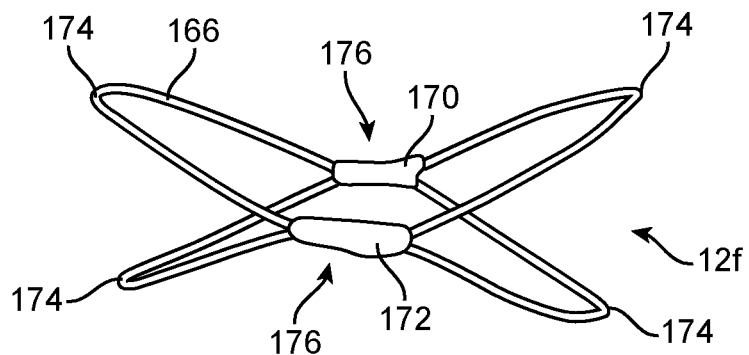
Figure 13C:
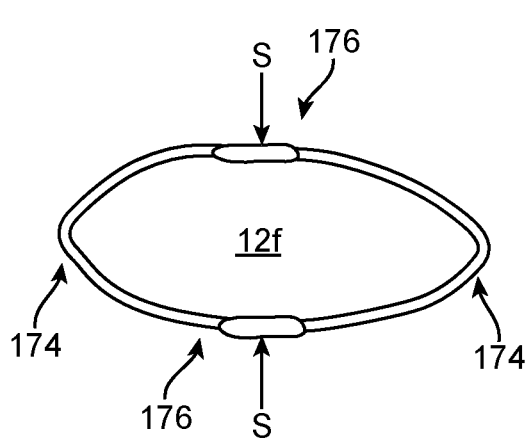
Figure 22A:
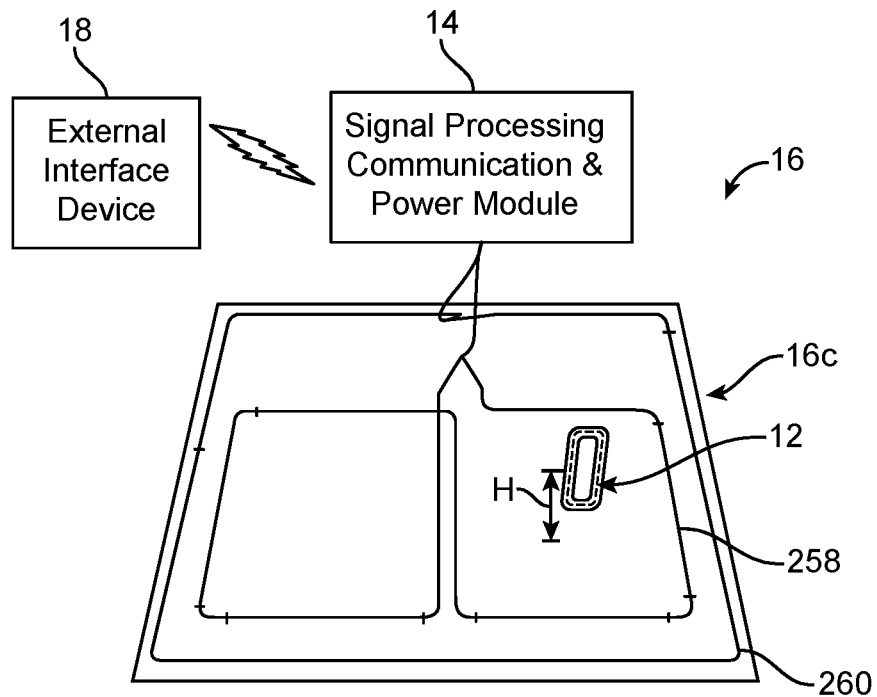
FIG. 22A illustrates an alternative system in accordance with the present disclosure for energizing and communicating with RC-WVM implants, including a planar antenna module with send and receive coils.
Figure 22B:
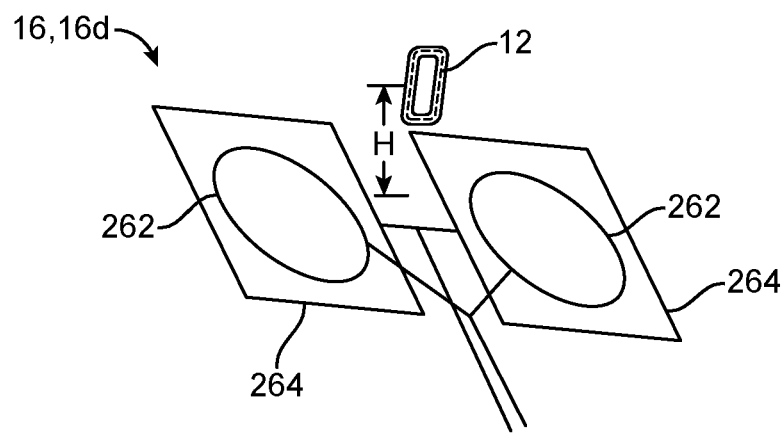
FIG. 22B schematically depicts a further alternative antenna module.

In another RC-WVM implant 12 alternative embodiment, an "x-bow"-shaped RC-WVM implant similar to RC-WVM implant 12d shown in FIG. 12B may be formed with two separate coils in orthogonal planes to allow measurement of the vessel dimension in two axes, i.e. in both the anterior-posterior direction and the medial-lateral direction. FIGS. 13A, 13B and 13C illustrate such an alternative embodiment. As shown therein, RC-WVM implant 12f is formed with two separate coils 166, 168 to form two separate, independent resonant circuits tuned to two different frequencies. RC-WVM implant 12f thus includes two capacitors 170, 172, one for each circuit. With two separately tuned coils, RC-WVM implant 12f has the ability to discriminate between changes in dimension along two perpendicular axes, one through coil ears 174, indicated by arrows E in FIG. 13A, and the other through coil spines 176, indicated by arrows S in FIG. 13C. The two separate resonant circuits can be separately energized so as to resonate independently. The two measurements may need to be taken using two input waveforms having different frequencies so that the outputs subsequently generated by RC-WVM implant 12f can be differentiated by the external receive antenna. Alternatively, coils of different geometry, or capacitors of different capacitance, could be used to produce different resonant frequencies for a given input waveform. An antenna module 16 with planar antenna coils, for example as shown in FIG. 22A or 22B may be preferred with such a two coil type implant such as RC-WVM implant 12f. With the implant shaped as shown in FIGS. 13A-C, coupling is anterior-posterior. Use of two separately tuned coils also provides an opportunity to exploit the mutual inductance of the coils. With two coils together as disclosed, the inductance of each coil may stay constant or equal compared to one another. Mutual inductance equals the first inductance multiplied by the second inductance and a coupling factor (M=L1*L2*k).

Figure 13D:
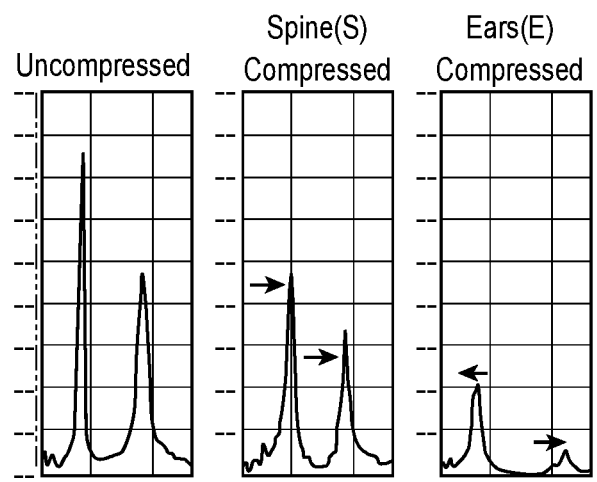

FIG. 13D shows signal response of a prototype RC-WVM implant 12f. The prototype was constructed with two 0.010" Nitinol frames, each insulated with PET heatshrink material. The overall frame size was approximately 25-30 mm diameter and approximately 60 mm long. A first coil on one frame comprised three turns of 60 strand 46 AWG copper Litz wire, with a soldered connection to a 15 ηF capacitor. A second coil opposite frame comprised four turns of 60 strand 46 AWG copper Litz wire, with a soldered connection to a 5.6 ηF capacitor. PET heatshrink insulation was provided around each coil and the two coils joined together in the x-bow configuration shown in FIGS. 13A-C with epoxy. The three plots in FIG. 13D represent (from left to right) the signal response for the uncompressed implant, the signal response for compression along the spines (arrows S) where the two frequency peaks increase in unison, and the signal response for compression at the coil ears (arrows E) where the gap between the frequency peaks increases. The independent response from each of the two coils is clearly represented by the two distinct frequency peaks in each plot and therefore the A-P and M-L distensions of the IVC can be understood.

Figure 14A:
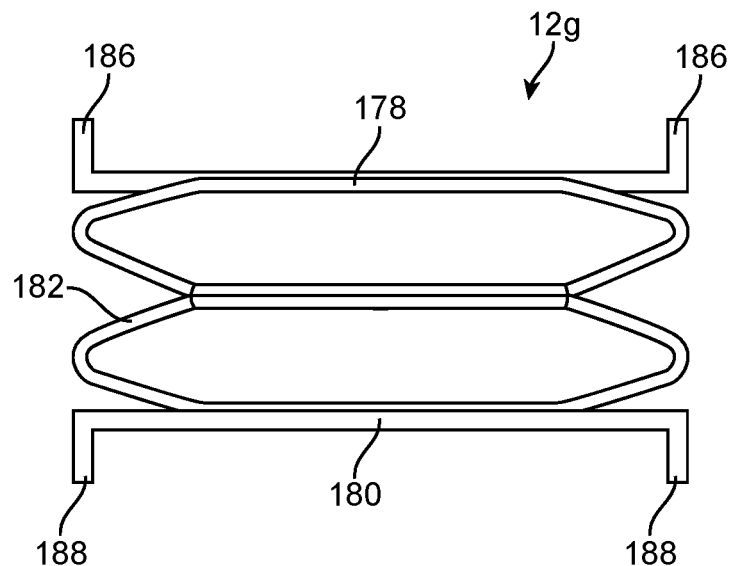
Figure 14B:
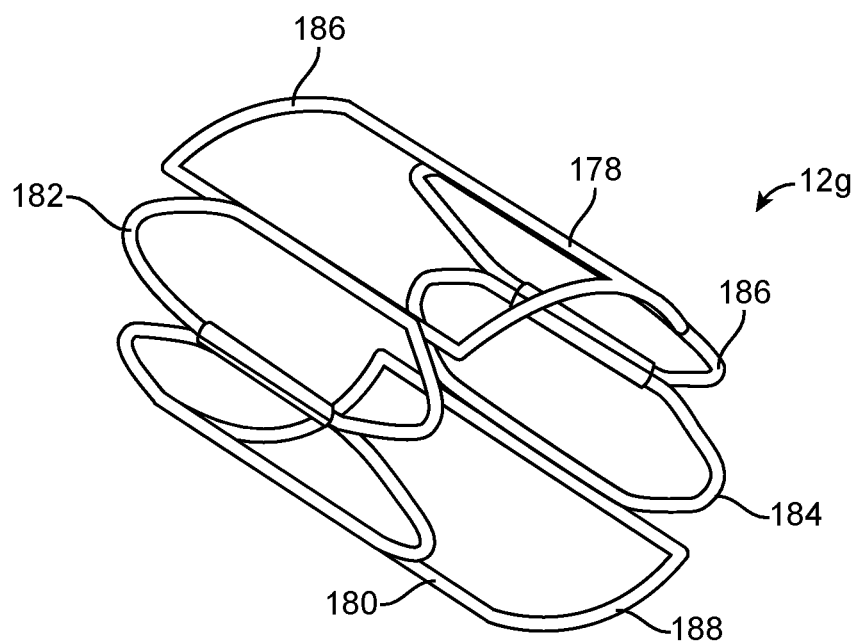

FIGS. 14A and 14B illustrate another alternative RC-WVM implant 12g, also with two separate coils that may be tuned to different frequencies. In this embodiment, coils 178 and 180 are mounted on resilient/compressible frame members 182 and 184. Coils 178 and 180 may be formed on frames with multiple turns of fine Litz wire as with other RC-WVM implant embodiments described herein and are generally rectangular in shape with slightly upturned ends 186 and 188. Coils 178 and 180 run perpendicular to loops in frame members 182 and 184. Frame members 182 and 184 also have electrical breaks as described above with respect to, e.g., frame 44. RC-WVM implant 12g as shown does not include discrete capacitors and hence relies on the inherent capacitance of the implant coils to complete the L-C circuit. However, discrete capacitors could be added in each coil as an alternative.

Other embodiments of RC-WVM implant 12 may be adapted to balance the anchoring and measuring requirements by providing separate, longitudinally spaced measurement and anchor sections. Such embodiments split the anchoring and measurement into two discrete regions longitudinally separated from each other a sufficient distance that the anchoring section does not distort or constrain the vessel in the region being measured. The radial force characteristics of the measurement and anchoring sections will determine the spacing required, in certain embodiments, where the radial force of both sections is relatively low, the spacing can be reduced to as little as 5 mm. Examples of RC-WVM implant embodiments with separate measurement and anchor sections are shown in FIGS. 15A-B, 16A-B and 17A-B. One such alternative embodiment is RC-WVM implant 12h, shown in FIG. 15A. As shown therein, anchor section 190 (also an antenna section as explained below) can be stiffer, of different geometry, with its expanded shape set to a larger diameter than measurement section 192 to securely anchor RC-WVM implant 12h. Anchor section 190 may be comprised of nitinol or other suitable material to increase resilience and/or stiffness while still allowing collapse for deployment. In some embodiments, a separate antenna coil may be integrated with or coupled to the anchor section, as described below, to enable separation of vessel measurement from signal transmission/reception.

Figure 15A:
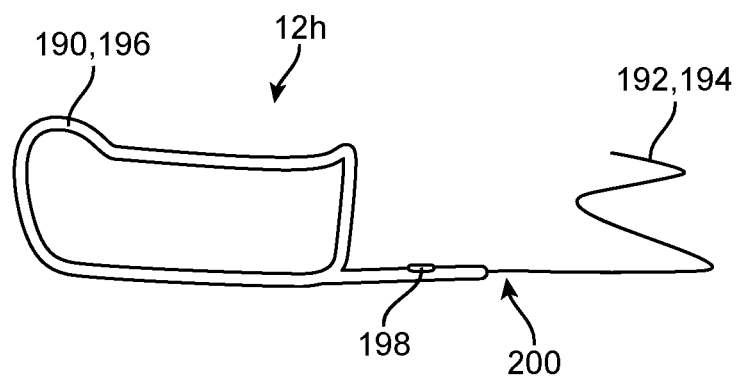
Figure 15B:
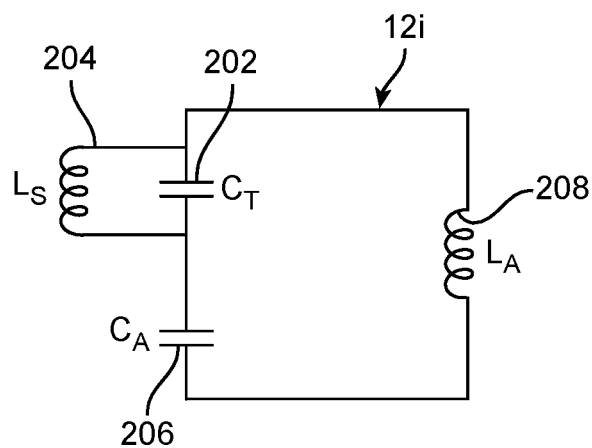

As mentioned, embodiments of RC-WVM implant 12 with separate anchor and measurement sections also may employ the anchor section as an antenna coil. RC-WVM implant 12h, shown in FIG. 15A, is an example of such an embodiment. Anchor section 190 and measurement section 192 are provided as two mechanically separate, but electrically continuous coils, one for vessel measurement and a second as an antenna for signal reception and/or transmission. Advantageously, separation of the measurement coil 194 from antenna coil 196 allows the antenna coil to be less affected by changes in vessel size and to have a shape and size selected to maximize the transmitted signal (i.e. magnetic field) generated by it. Moreover, antenna coil 196 may be configured to anchor the implant in the vessel, or may be integrated or coupled to an anchoring element, without affecting the performance of measurement coil 194. Antenna coil 196 may thus have more turns of more strands of Litz wire and a different geometry and size than measurement coil 194 to optimize both anchoring and communication with the external antenna. In the RC-WVM implant 12h example, anchor section 190 is formed as multiple loops in a generally oval shape, shaped to engage the inner walls of the vessel. Measurement section 192 is formed, for example, as a sinusoidal "z" shape, which may comprise a thinner, lower radial force nitinol frame, with fewer turns of higher gauge (thinner) wire, or fewer strands of Litz wire than antenna coil 196. Measurement section 192, forming measurement coil 196, is highly compliant and minimizes distortion of the vessel's natural expansion and collapse so as to accurately perform the measurement function. Measurement coil 194 may have a variety of other geometries, such as sinusoidal, square wave, or other open-cell designs, but in general will not have closed-cells or other electrical connections between the successive loops of the coil, which could create problematic eddy currents. RC-WVM implant 12h is also provided with discrete capacitor 198 on strut section 200 joining the anchor/antenna section and measurement section/coil.

A further alternative embodiment for RC-WVM implant 12 involves the use of two capacitors to "double tune" the device. One example of such an embodiment is RC-WVM implant 12i, shown in FIG. 15B. In this embodiment, first capacitor ($C_T$) 202 is associated with measurement coil ($L_S$) 204, while second capacitor ($C_A$) 206 is associated with antenna coil ($L_A$) 208, allowing independent tuning of the measurement and antenna circuits to optimize dynamic range, field strength and signal duration. These capacitors can be selected such that the deflection of measurement coil 204, which is a low percentage of the overall inductance of RC-WVM implant 12i and would normally result in only a small shift of the resonant frequency, can be made to have a larger dynamic range and therefore produce a more detectable shift in this frequency. At the same time, the resonant frequency of antenna coil 208 can be optimized for reception by the external antenna. With such an arrangement antenna coil 208 also may be configured as an anchor section as discussed above.

FIGS. 16A-B illustrate further alternative RC-WVM implants 12j and 12k. RC-WVM implant 12j, in FIG. 16A, includes sinusoid element sensor 210 composed as previously described with respect to other similarly shaped sensor coils. Sensor element 210 is attached via elongate isolation connector 212 to anchor section 213. Sensor element 210 also communicates with antenna module 16. Anchor section 213 is provided with a curved wire anchor element 214 configured to engage with the IVC wall and fix the implant at a monitoring location. Isolation connector 212 isolates sensor element 210 from any distortions or irregularities that the IVC wall may be subjected to by anchor section 213. Alternative RC-WVM implant 12k, shown in FIG. 16B, employs two separate sinusoid elements 216, 217, formed in one continuous coil using techniques as described herein. Sinusoid element 216 exerts a lower radial force in resistance to diameter changes and is thus designed to operate as the RC-WVM sensor coil. Sinusoid element 217 is configured to exert a higher radial force and thus forms an anchor section and also may be configured for communication with antenna module 16. Anchor isolation means 218 may be formed as a wire connection portion between elements 216 and 217.

FIGS. 17A-B illustrate a further alternative RC-WVM implant 12m, wherein FIG. 17A shows an oblique view and FIG. 17B shows a normal view. Coil sensor element 220 is provided as elsewhere described herein; in this case having a somewhat wider cross-section as a result of coil wires formed around a rectangular cross-section laser cut frame. Anchor section 222 is displaced from sensor element 220 by anchor isolation means 223. Both anchor section 222 and anchor isolation means 223 may be formed, for example, from nitinol wire. Locating anchor section 222 separately from sensor element 220 allows for the use of higher radial force in the anchor section without impacting the sensed region of the IVC. Anchor section 222 may rely on radial force alone for fixation or may incorporate individual, pointed anchors. Anchor section 222 may be configured as in many embodiments, including any other anchor/anchor section disclosed herein. As shown in FIGS. 17A-B, anchor section 222 employs "ears" 224 that are self-biasing outward to widen and engage with the vessel wall.

Figure 18:
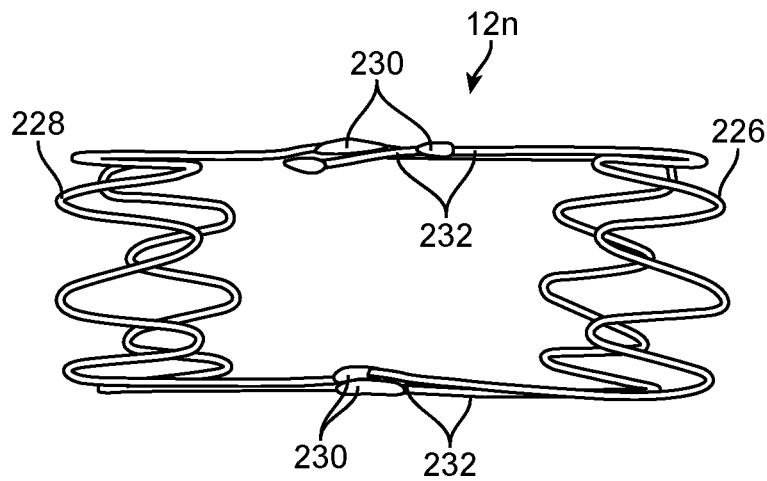

FIG. 18 illustrates a further alternative RC-WVM implant 12n. In this embodiment, two sinusoidal, "Z"-shaped coils 226, 228 are joined at connections 230 by two pairs of elongate members 232. Coils 226, 228 may be formed on different thicknesses frames of nitinol wire thus resulting in different radial forces, i.e., a lower force end for measurement and a higher force end for anchoring. Elongate members 232 thus also serve as anchor isolation means between sensor and anchor coils. The sensor coil may be a two turn coil, constructed from multi-strand Litz wire (as elsewhere described herein) and the anchor coil may also have a large area to further provide strong communication with antenna module 16.

Figure 19A:
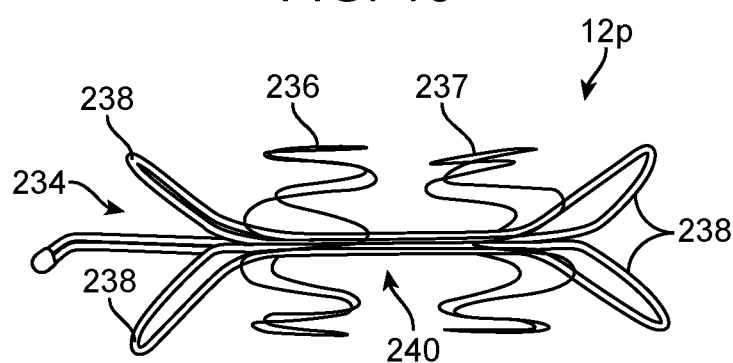
Figure 19B:
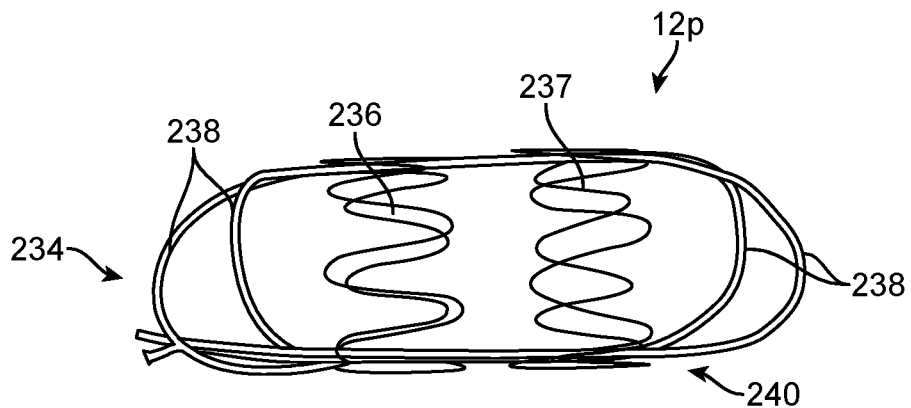

FIGS. 19A and 19B illustrate a further alternative RC-WVM implant 12p. In this embodiment, two turn coil 234, which may be formed from wrapped Litz wire as elsewhere described, is separated from dual sinusoidal nitinol anchoring structure 236, 237. Outwardly curved "ears" 238 of coil 234 are configured to engage the IVC wall with less force to form the sensor or measurement element, and relatively, the large area of coil 234 optimizes communication with antenna module 16. Dual nitinol anchoring structures 236, 237, provide a separated, higher radial force, anchoring portion. Thus, a flat portion 240 of coil 234 provides an anchor isolating function.

In any embodiment of RC-WVM implant 12 described herein, it may be advantageous to form the coil portion of the implant with multi-stranded wire or cable comprising a plurality of separately insulated strands wound or braided together to optimize the performance with high frequency alternating current. In some embodiments, the electrically conductive wire or wires used in the implant may comprise Litz wire in which the separately insulated strands of wire are braided or wound together in a particular prescribed pattern to optimize AC current transmission by optimizing for the high frequency "skin effect". The individual wire insulation could be PTFE, polyester, polyurethane, nylon, or polyimide, among others. An additional insulated jacket may be provided around the entire multi-stranded wire or cable in order to provide electrical insulation from blood, which could otherwise render the implant suboptimal or unreliable under some circumstances, and to bind the Litz wire to the frame. Such additional insulation may be provided in the form of PET (polyethylene terephthalate), ETFE, FEP, PE/PP, TPE, polyurethane, silicone, polyimide, or other material, and may be provided on the wires of an RC-WVM implant and/or to encase RC-WVM implant 12 in its entirety. Due to the use of high frequency electromagnetic signals, more, or different, insulation may need to be provided for the electrical portions of RC-WVM implant 12 than may be required for other types of implants or electrical devices.

Figure 20A:
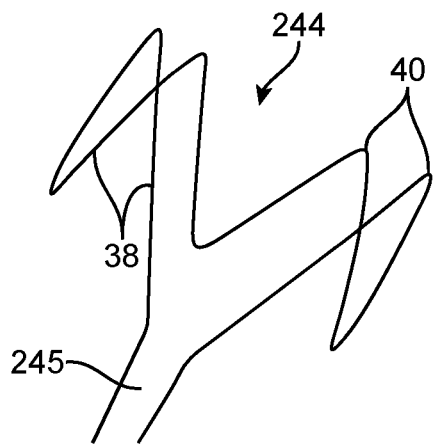
FIGS. 20A and 20B illustrate alternative frame structures for use in an RC-WVM implant as disclosed herein.
Figure 20B:
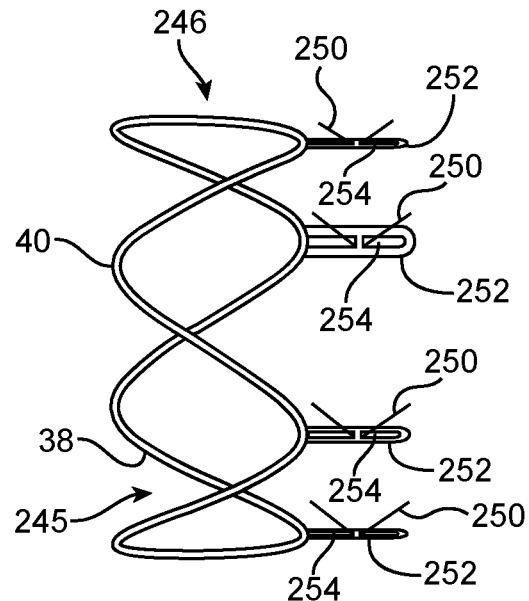

In some embodiments, nitinol frame such as frames 244 and 246, shown in FIGS. 20A and 20B, respectively, may be used to provide structural support and enhanced anchoring, and to facilitate the crimping or compression and deployment or expansion of RC-WVM implant 12 into/from the delivery sheath. For example, the nitinol frame may be formed in the desired shape of the coil (using formed wire 244 or a laser cut tube or thin plate 246), and the conductive wire may then be wound coextensively with the nitinol frame to form the coil. Alternatively, nitinol wire and Litz wire may be co-wound or braided and then the composite cable used to form the coil, so that the electrical inductance of the nitinol wire is added to that of the Litz wire. The structure may then be insulated with, e.g., silicone tubing or moulding. In other embodiments, a nitinol tube with Litz wire disposed coaxially within it (or vice versa) could be used; such a tube may have, for example, about a 0.020" to 0.050" inner diameter with walls having a thickness of, for example, about 0.005" to 0.020". In other embodiments, the coil may be formed with gold-coated nitinol wire and/or a drawn-filled tube. Any exposed surfaces of any non-insulated portions of RC-WVM implant 12 are preferably made from or plated with biocompatible polymers or metals such as gold, platinum, palladium/molybdenum or plated in these materials to prevent undesirable effects or health issues. Nitinol wire frame 244 includes strut sections 38 and crown sections 40 as previously described. As a wire formed frame, frame 244 has a natural break 245 that occurs where the wire ends are brought together. Where needed, to avoid creating an electrical loop through the frame, the break can be bonded together with an insulating material such as epoxy to complete the frame structure.

Laser cut frame 246, as shown in FIG. 20B, is cut from a nitinol tube which is expanded and shape set to size including integral anchor elements 250, formed by laser cutting orifices 254 and shape setting the anchor elements 250. Frame 246 is electro-polished after cutting, before coil wires are wrapped as described below. When formed by cutting from a tube, frame 246 will be a continuous member and thus must be cut at location 38 during a pre-coil wrapping stage to avoid forming an electrical loop within the frame which could negatively impact the performance of the coil. The cut section may then be re-joined by bonding with an insulating material such as epoxy or over-moulding with a polymer. Anchors 250 may be located on extending posts 252 with openings 254 from which anchor elements 250 are formed. Such anchor elements may extend bi-directionally as shown or only in a single direction. While relatively short compared to other frame dimensions, anchor elements 250 should be long enough to protrude past wire and insulation when added to frame 246 to engage with the vessel wall for fixation. Typically, when anchor elements 250 are formed only on one end of the fame, they will be on the proximal end of the frame so as to deploy last when deployed from the delivery catheter as explained above. However, alternatively, anchor elements 250 may be formed on both ends of the frame. As shown in FIG. 20B, anchor attachment elements 250 are provided on each proximal crown section 40 joining strut sections 38 of frame 246. Alternatively, extending posts 252 o4 other anchor attachment points may be provided on fewer than all crown sections, for example on every other crown section.

Figure 21A:
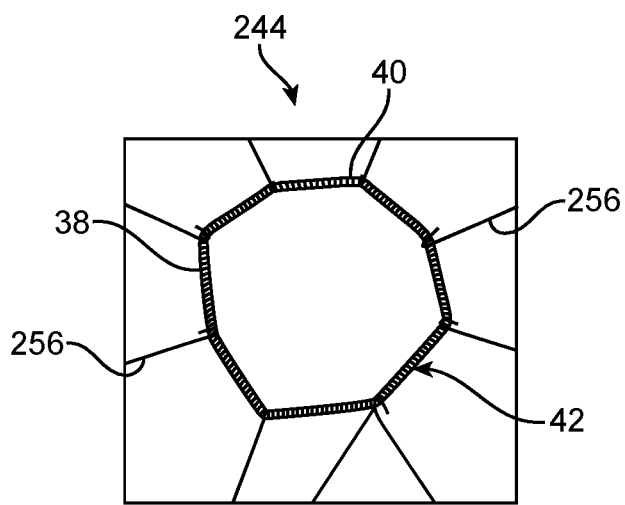
FIGS. 21A and 21B illustrate an example of a method of making an RC-WVM implant embodiment according to the present disclosure.
Figure 21B:
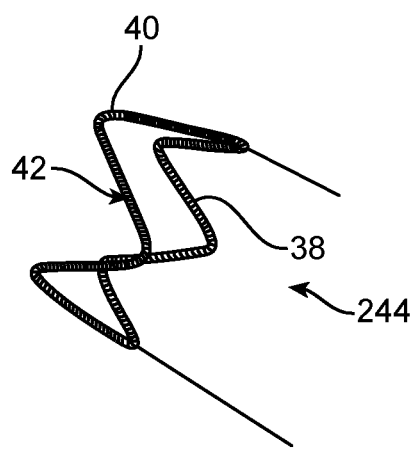

FIGS. 21A and 21B illustrate aspects of one example of a method for making an RC-WVM implant using a wire frame such as wire frame 244 shown in FIG. 20A. After formation of the frame, it is expanded on a fixture, such as by hooks 256, to approximately a maximum diameter. The selected wire, such as Litz wire 42, is then wrapped around the frame. Multiple parallel wraps may be made, which may have turns between crown sections 40 to distribute the wire evenly and cover the frame. The wrapping objective is to achieve an evenly distributed wire, covering the strut and crown sections 38, 40 with a consistent but thin wire coating. In one alternative technique, the first and last wraps may be radial to bind wire 42 to the frame. After wrapping is complete, the structure is insulated by a dip, spray or heatshrink process. Typical insulation materials may include silicone, TPU, TPE or PET. The method steps heretofore described contemplate use of individually insulated Litz wire strands. If uninsulated wire strands are to be used, then an additional pre-wrapping step of insulating the frame itself before applying the wire may be desired. FIG. 21B illustrates the wrapped frame 244 after it is removed from fixture hooks 256. Another technique involves laying the multiple strands of thin wire next to each other in a continuous loop with as many turns as called for in the design. Such loops may be wrapped around the frame only a small number of times compared to the method above, e.g. as few as one or two times. The entire assembly may then be held together with a suitable external insulation as described.

The number of turns of wire used to form a coil portion of RC-WVM implant 12 embodiments may be optimized to provide enough conductive material to allow the use of lower capacitance value capacitors in order to enable the use of a physically smaller capacitor, thereby minimizing implant size. The preferred number of turns will depend on various factors including the diameter of the coil, the size and number of strands of wire or cable, the strength of the field produced by the transmit antenna, the sensitivity of the receive antenna, the Q value of the capacitor, and other factors. Such coils could have anywhere from 1 to 10 or more turns (each turn being a complete 360 degree loop of the wire around the frame), and preferably have at least 2 such turns. For example, Litz wire used in an RC-WVM implant 12 embodiment may have 180 strands of 46 AWG (0.04 mm wire), but could include anywhere from 1 to 1000 strands, and the strands could be about 0.01 to 0.4 mm in diameter.

Alternative System Embodiments, Components and Modules

Alternative embodiments 16c and 16d for antenna module 16 are illustrated, respectively, in FIGS. 22A and 22B. As shown, in FIG. 22A, control system 14 generates input waveforms and receives signals back from RC-WVM implant 12 as elsewhere described herein. In particular, signal generator module within control system 14 drives figure-eight transmit coil 258, which energizes RC-WVM implant 12. Due to the LC circuit formed by the wires of RC-WVM implant 12, the implant will then resonate and produce magnetic fields of its own as a consequence of the induced current. The magnetic fields produced by RC-WVM implant 12 can then be measured using receive coil 260, which is monitored via amplifier-receiver module within control system 14, which may then deliver data to remote system 18. In alternative antenna embodiment 16c, receive coil 260 comprises a single, square coil lying in the same general plane as the transmit coils so as to be properly oriented to generate a current when a magnetic field is generated by the implant. Under the well-known right-hand rule, when a current flows through the transmit coils, a magnetic field will be generated in a direction perpendicular to the plane of each coil. By causing the current to flow in opposite directions around each transmit coil, the magnetic field forms a toroidal shape flowing from one transmit coil into the patient's body, through the inductive coil of the implant, and back out of the patient through the other transmit coil. This arrangement produces a geometric decoupling of the transmit and receive coils, as is described in greater detail below in connection with FIG. 25B. Also, as discussed elsewhere in more detail, it will be noted that the implant should be oriented such that the field produced by the transmit coils passes through the center of the implant's inductive coil. This generates a current flowing through the inductive coil which, due to the capacitor in the circuit, resonates at a specific frequency based upon the size and shape of the coil. This current in turn generates a field which passes out of the implant perpendicular to the plane of the inductive coil, and through the external receive coil, generating a current therein. The frequency of this current can be measured and correlated with vessel diameter. In alternative antenna embodiment 16d, transmit coil 262 also comprises two square coils, but in this case receive coil 264 comprises two round coils, one each disposed within a transmit coil. Again, the transmit and receive coils are disposed in the same plane as described above.

Example 2

Systems as described herein have been evaluated in pre-clinical testing using RC-WVM implant 12c as shown in FIG. 12A, and antenna module 16d as schematically depicted in FIG. 22B. The implants were deployed into porcine IVCs using femoral access and standard interventional technique. Deployment was confirmed angiographically and using intravascular ultrasound. External antenna module 16d was placed under the animal and ring-back signal obtained.

Figure 23B:
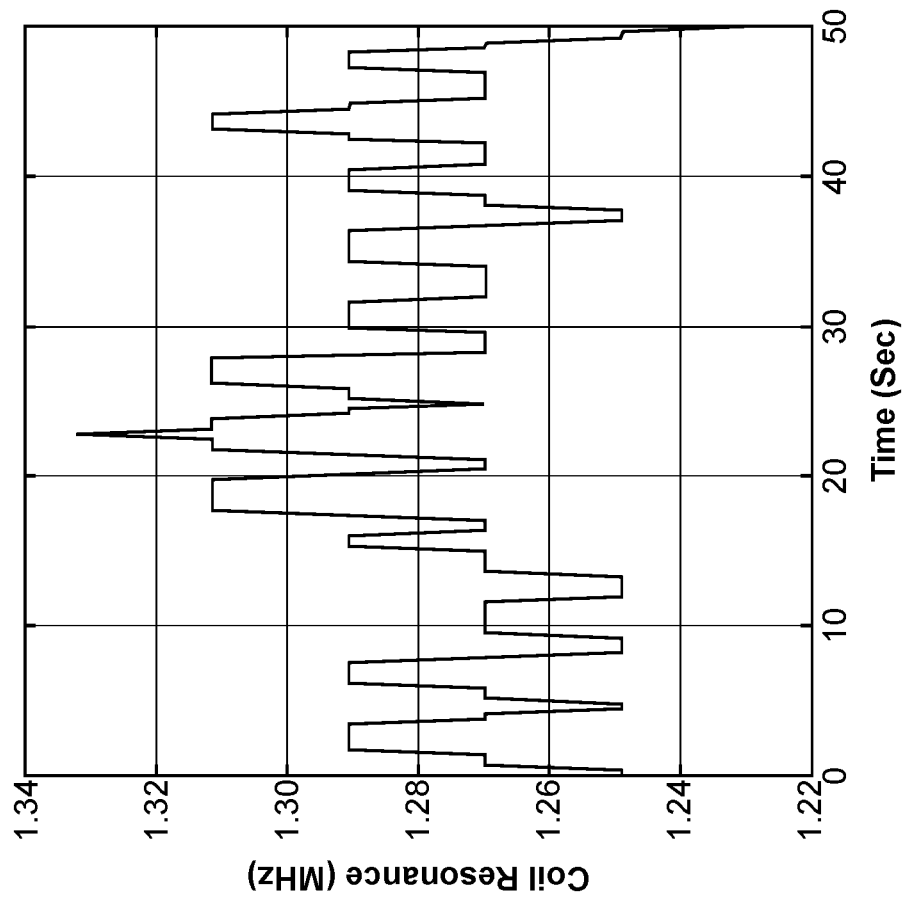
FIGS. 23A and 23B illustrate signals obtained in pre-clinical experiments using the prototype implant shown in FIG. 12A and antenna module configuration shown in FIG. 22B.
Figure 23A:
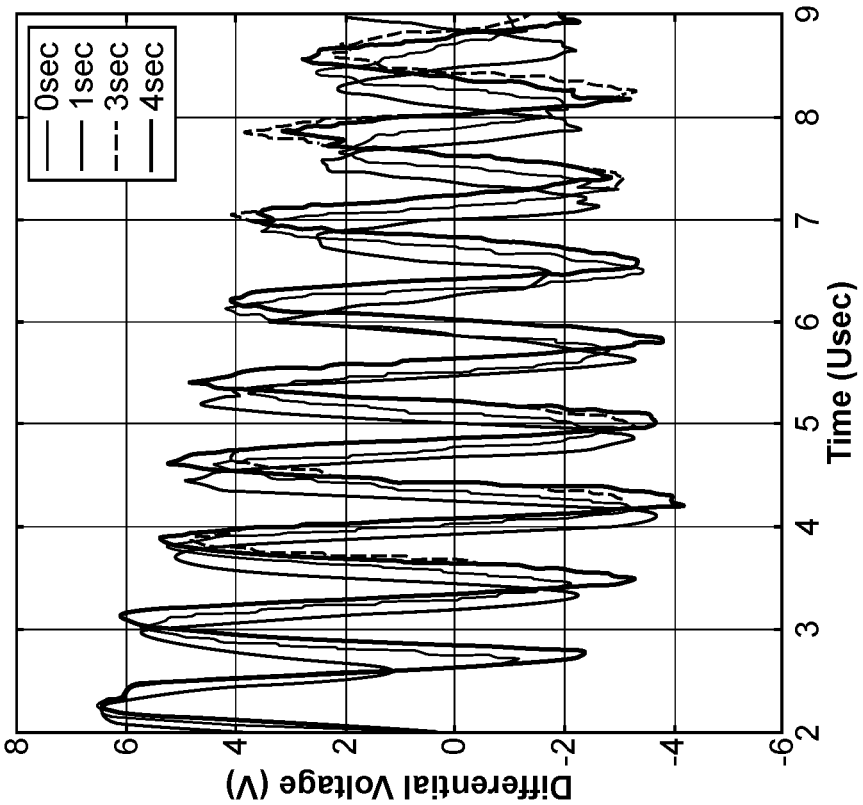

FIG. 23A illustrates the raw ring-back signal obtained in pre-clinical testing at multiple time points, and FIG. 23B illustrates how this signal can be converted from frequency to time domain using Fourier transform. The coil resonance modulation can then be converted to vessel dimension through calibration. In FIG. 23B, the frequency modulates between approximately 1.25 to 1.31 MHz. It was then possible to correlate this frequency shift to an IVC dimensional change by characterizing the compression of the coil under specific displacements (and their associated resonant frequencies) as described below. The step nature of the frequency signal may be improved by increasing the Q of the signal, providing longer ring-down and facilitating better resolution of the signal. The strength of the signal will also be optimized with iterations of Litz wire and insulation.

The raw voltage signal in FIG. 23A is as received from the RC-WVM implant, which was positioned in an anterior-posterior orientation of the spines. An antenna module as depicted schematically in FIG. 22B, employing a figure-eight circular shape coil was used as transmit coil and a figure-eight square coil as receive coil "TX" and "RX", respectively. These were coupled and an Arduino controller (or any other microcontroller could be used) was used to switch the receive coil on and off resonance to improve transmit and receive decoupling. The decompressed resonance frequency of the implant coil was 1.24 MHz at 25 mm diameter. Fully compressed, the resonance frequency of the implant coil was 1.44 MHz. FIG. 23B shows the resonance frequency as determined for each measurement as a function of time with a clear variation of frequencies in the expected compression range between 1.24 and 1.44 MHz-1.25 MHz being nearly fully decompressed (24 mm diameter=only 1 mm of compression) and 1.31 MHz being about 50% compressed (16.25 mm diameter=8.75 mm of compression). Based on these results, modulation of resonant frequency of the RC-WVM correlated with IVC diameter variation was observed.

Figure 24A:
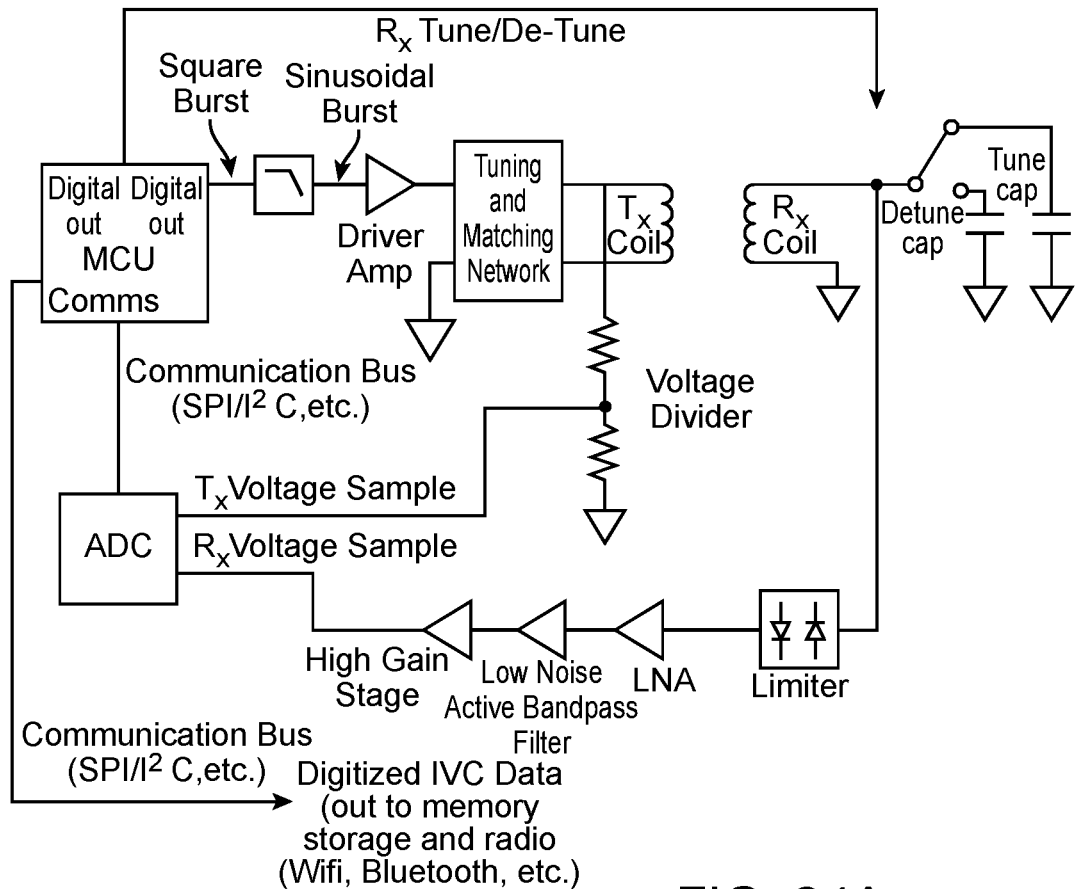
FIG. 24A is a circuit diagram of an example excitation and feedback monitoring ("EFM") circuit that can be used with embodiments of RC-WVM implants and systems as described herein.
Figure 24B:
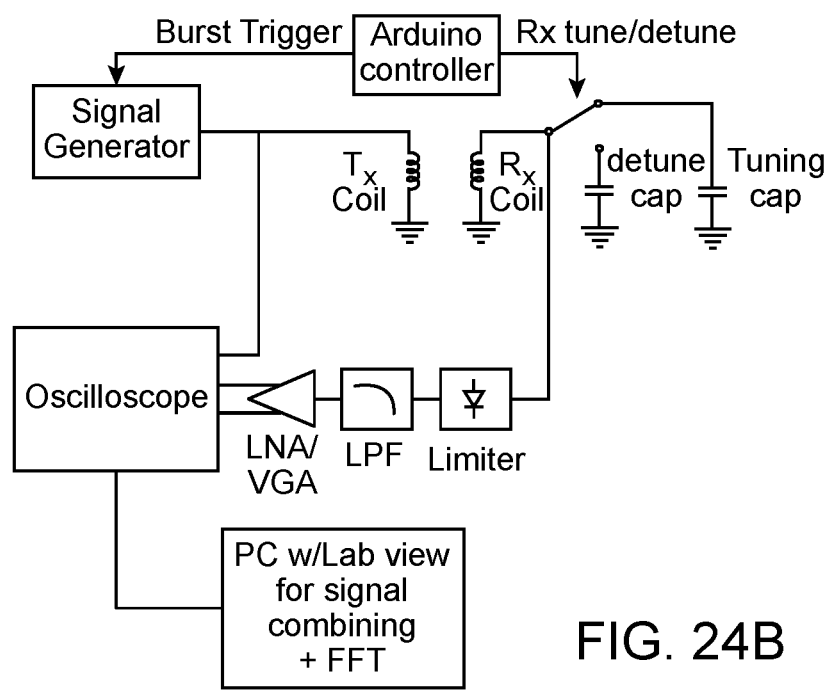
FIG. 24B is a circuit diagram of another example EFM circuit that can be used with embodiments of RC-WVM implants and systems as described herein.
Figure 25A:
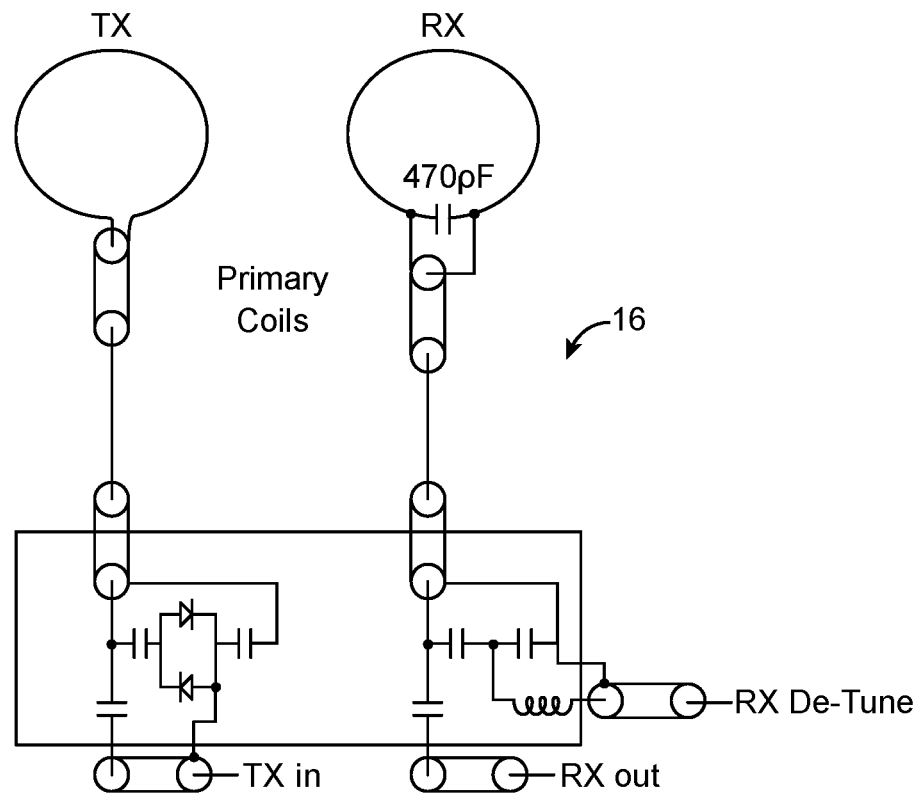
FIG. 25A is a circuit diagram of an antenna module tuning and detuning network that can be used with an EFM circuit like that of FIG. 24A or 24B.
Figure 25B:
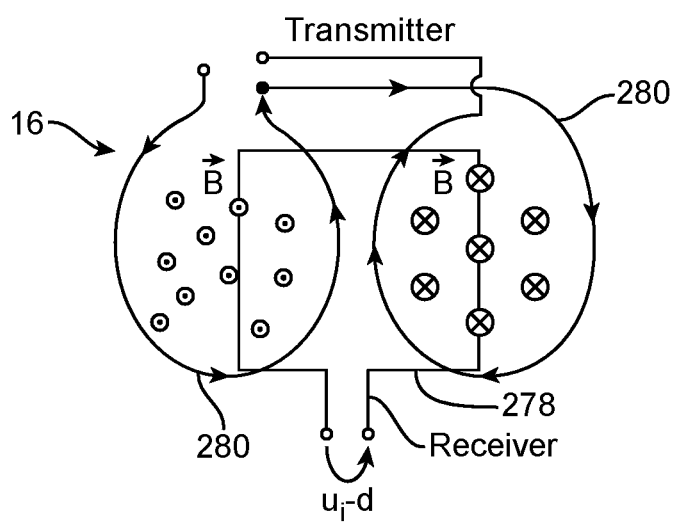
FIG. 25B schematically depicts a further embodiment of antenna module coils arranged to provide geometric decoupling of the transmit and receive signals.

Further alternative examples of configurations and components for control system 14 and antenna module 16 are shown in FIGS. 24A through 26C. FIGS. 24A and 24B illustrate examples of excitation and feedback monitoring ("EFM") circuits that can be used to excite the L-C circuit in a RC-WVM implant and monitor the response of the RC-WVM implant to that excitation. These circuits may be used as components in alternative control systems 14. After the receive coil in an EFM circuit receives signals corresponding to the response of the RC-WVM implant to the excitation previously generated using the EFM circuit, those signals may be processed digitally to convert the signal to the frequency domain using a Fast Fourier Transform ("FFT") algorithm, a zero-crossing algorithm, or other methods. After such processing is complete, the frequency having the highest magnitude within the calibration frequency range of the implant (i.e. all possible frequencies that the implant can contain such as for instance 1.4 to 1.6 Mhz) is determined and should correspond to the resonant frequency of the LC circuit in the RC-WVM implant. By continually monitoring the frequency having the highest magnitude in signals received from the LC circuit of the RC-WVM implant in response to discrete excitations of a transmit coil connected to the EFM circuit, the EFM circuit can be calibrated to translate a frequency shift in signals received from the L-C circuit of the RC-WVM implant into a dimension, area and/or collapsibility index of the vein or artery in which the RC-WVM implant is disposed. In some implementations, a heartbeat and/or other physiological signals (e.g. respiration, cardiac heart beat) can be derived from small variations in frequency or magnitude or shape of signals received from the RC-WVM implant after being excited by a transmit coil attached to an EFM circuit. In some embodiments, magnitude variations in the signals received from the RC-WVM implant can be used to validate frequency variations in the signals received from the RC-WVM implant through cross-correlation or other methods of correlating signals. FIG. 25A illustrates one example of a tuning and detuning network, which may be used in antenna module 16 in conjunction with excitation and feedback monitoring ("EFM") circuits as exemplified by FIGS. 24A and 24B, discussed. In an antenna module 16 with this configuration, TX coil transmits the excitation signal to RC-WVM implant 12 and RX coils receives the ring-back signal from the implant.

In some embodiments, where a single antenna-coil may be used for both the transmit and receive signals, antenna module 16 includes a switching mechanism to alternate between transmission and reception, thereby eliminating interference between the transmitted signal and the received signal. Examples of such switches are the passive and active diode switches shown in FIGS. 28A and 28B. In other embodiments, in which antenna module 16 employs separate transmit and receive coils, the receive coil may be geometrically decoupled from the transmit coil to eliminate interference between the two, even when operating simultaneously. In one such embodiment, shown in FIG. 25B, receive coil 278 forms a single square shape surrounding all or a portion of both transmit coils 280 resulting in a geometric decoupling of the coils. (A similar arrangement is also depicted schematically in FIG. 22A.) Use of a smaller antenna for transmit reduces emissions, while use of a larger receiver coil maximizes signal-to-noise ratio. Such an arrangement exploits the optimum geometry for transmitting from a planar, figure-eight loop into an orthogonally oriented RC-WVM implant while the receive function can be used to maximize the magnetic flux caught from the implant in the receive coil. This arrangement can be helpful where loop-to-loop coupling is not possible, e.g., when a belt antenna is not used. The coils are tuned to resonance frequency and matched to source impedance (e.g., 50 Ohm).

Advantageously, this allows simultaneous transmission and reception of fields to/from the implant to maximize signal strength and duration, and potentially eliminate complex switching for alternating between transmission and reception. Notably, in some implementations, single or plural circular or other-shaped transmit and/or receive coils may be used, the transmit and receive coils may be disposed in the same plane or different planes, and the area enclosed by the transmit coil may be larger or smaller than the area enclosed by the receive coil. The transmit and receive coils may be formed using copper tape or wire or could be implemented as a portion of a printed circuit board.

The transmit and receive coils used for exciting RC-WVM implant 12 and receiving the implant ring-back signal in response to that excitation, respectively, should be tuned (matched and centered) on the particular RC-WVM implant's L-C circuit resonant frequency range. In exemplary embodiments, a signal generator may be used to generate a sine wave burst of 3 to 10 cycles at 20 Vpp with a frequency selected to maximize the response of the RC-WVM implant L-C circuit. The signal generator may transmit a burst at whatever rate provides a clinically adequate measurement of the variation in the vessel dimensions; this could be every millisecond, every ten milliseconds, or every tenth of a second. It will be understood that a variety of waveforms may be used including pulse, sinusoidal, square, double sine wave, and others so long as the waveform contains the spectral component corresponding to the resonant frequency of the implant. Geometric decoupling, damping, detuning, and/or switching may be used to prevent the transmit pulse signals from being picked up by the receive coil while the transmit coil is transmitting.

Figure 26A:
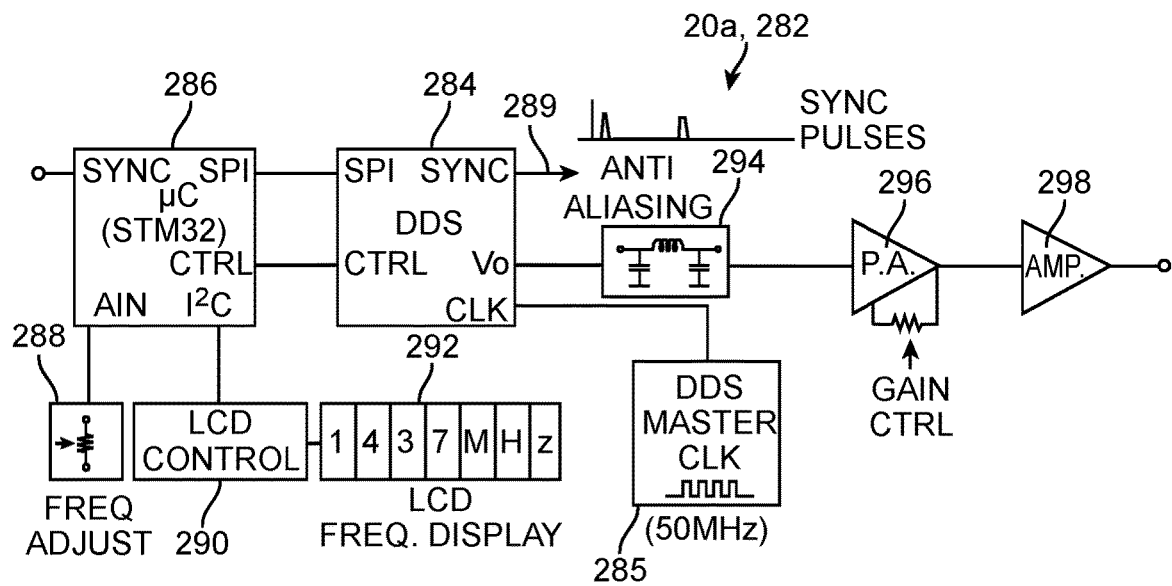
FIG. 26A illustrates an alternative signal generation module for systems according to embodiments disclosed herein.

FIG. 26A schematically depicts an alternative signal generation module 20a as excitation waveform generator 282, which generates the RF energizing signal transmitted to RC-WVM implant 12 (not shown) by antenna module 16 (not shown). In this embodiment, Direct Digital Synthesis (DDS) waveform synthesizer 284 (with clock signal from clock 285) provides a low voltage RF burst signal the parameters of which are configurable by external input through microcontroller 286 using frequency adjustment control 288. Microcontroller 286 also includes sync connection 289 to receiver-amplifier module 20b. LCD controller 290 communicates with microcontroller 286 to cause LCD display 292 to display the selected frequency. Microcontroller 286 thus initializes and programs the DDS 284 allowing configuration of output waveform parameters (e.g., frequency, number of cycles per RF burst, interval between burst, frequency sweep, etc.). Output from DDS 284 (low amplitude RF signal) is applied to high order, anti-aliasing low pass filter 294. The filtered signal from filter 294 is applied to an amplification chain, which may comprise preamplifier 296 and output amplifier 298 in order to present a flat frequency response over the frequency band of interest.

Figure 26B:
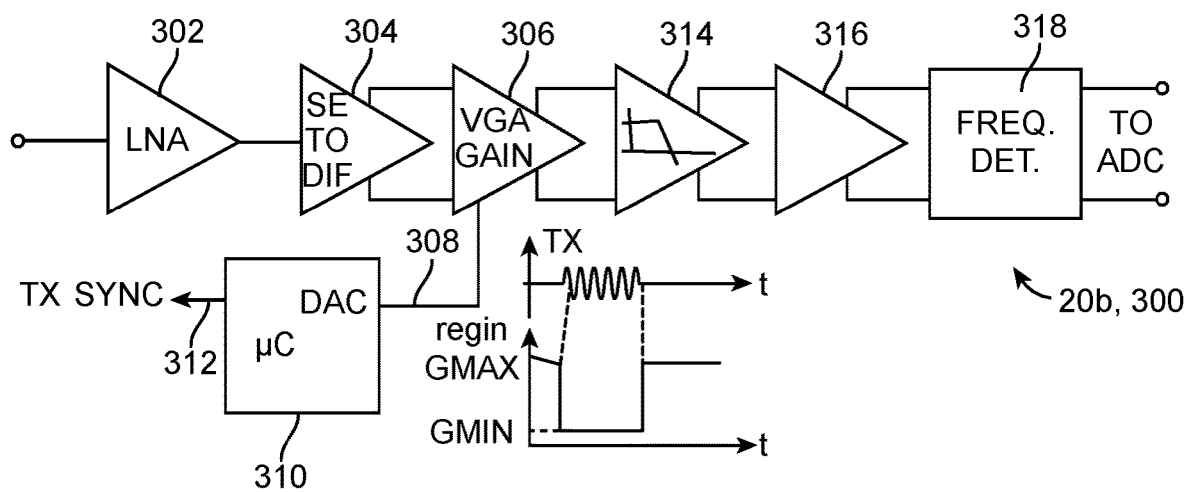
FIG. 26B illustrates an alternative receiver chain signal conditioning module for use in systems according to embodiments disclosed herein.

FIG. 26B schematically depicts an alternative receiver-amplifier module 20b as receiver chain 300, which conditions the ring-back signal received from RC-WVM implant 12 (not shown) by antenna module 16 (not shown) after excitation by signal generation module 20a. In this example, a single-ended low-noise preamplifier (not shown) provides flat response over the frequency band of interest and input to low noise amplifier 302 is matched to the receiver antenna of antenna module 16 (not shown). Unity gain amplifier 304 provides single-ended to differential conversion of the signal into a programmable gain, differential to differential stage in order to provide a high level of amplification. Variable gain amplifier 306 is controlled by the Digital-to-analog (DAC) output 308 of microcontroller 310, which is synced to signal generation module 20a, for example excitation wave form generator 282 shown in FIG. 26A, at sync connection 312 so that the gain is minimized during the excitation period to minimize coupling of excitation signal in the receiver circuitry. A low-pass or band-pass differential filter/amplifier 314 of an order of at least four (4) provides rejection of noise and unwanted signals. Output differential amplifier 316, the gain of which is selectable so that the magnitude of the output signal covers as much dynamic range as possible of the data conversion stage communicates with hardware-based frequency detection 318 to assert the frequency of the response signal provided by the sensor. Frequency detection 318 provides an output to an analog-to-digital converter (not shown).

Figure 26C:
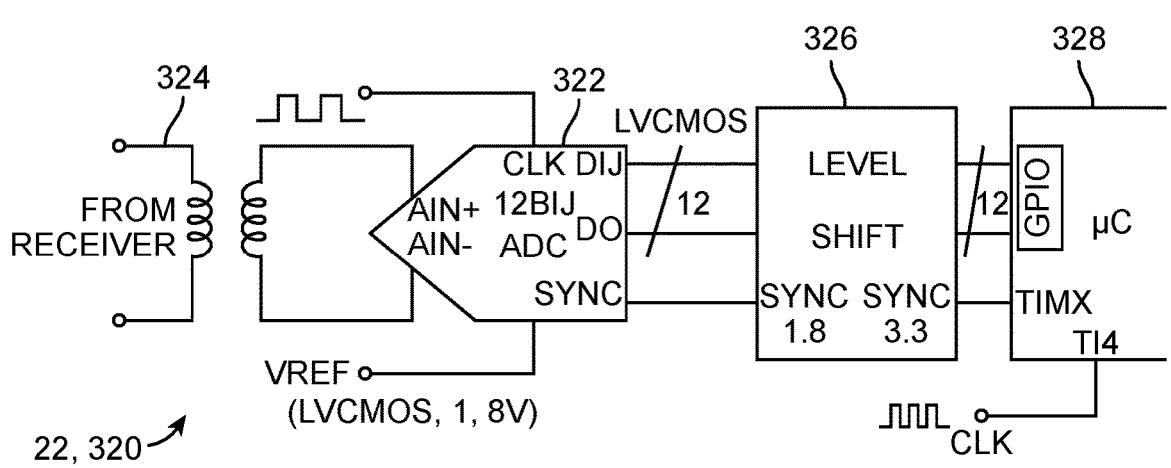
FIG. 26C illustrates an alternative data conversion module for use in systems according to embodiments disclosed herein.

FIG. 26C schematically depicts an alternative communication module 22 as data converter 320, which processes the signal from receiver-amplifier module 20b to allow for interpretation of the measurement signals from RC-WVM implant 12 (not shown). In this example, data conversion is achieved by means of high-speed, high-resolution, parallel output Analog-to-Digital converter (ADC) 322. Coupling from receiver-amplifier module 20a to ADC 322 is performed by coupling transformer 324 to minimize noise. ADC 322 may be specified to provide LVCMOS or CMOS compatible output to easily interface with a wide range of commercially available microcontrollers. In one embodiment, low voltage CMOS (LVCMOS) to CMOS level shifter 326 is employed for interfacing purposes with microcontroller 328. ADC 322 provides a conversion complete signal to sync with the data capture stage.

FIGS. 27A and 27B show further alternative embodiments for antenna module 16 as alternative belt antennas 16c and 16d, respectively. In order to accommodate patients of different girth, belt antenna 16c includes fixed portion 330 and one or more extension portions 332 of varying lengths. Fixed portion 330 includes male and female connectors 334, 336, which may connect directly to form a smallest size belt by both mechanically securing the belt and electrically completing the antenna coil. Extension portions also include male and female connectors 334, 336 so they may be connected into a fixed belt portion thus providing different sizes and completing mechanical and electrical connections. In order to tune the antenna and match it to the RC-WVM implant and signal generation circuitry (e.g. modules 20a), one option is to provide fixed portion 330 and each different length extension portion 332 with a fixed inductance, resistance and capacitance such that total parameters for the completed belt antenna 16c are known corresponding to each set length. Signal generation module 20a of control system 14 (not shown) can thus be adjusted as needed for a particular length belt and patient girth to provide necessary tuning and matching. Instead of different length extension portions, belt antenna 16d uses multiple connection points 340 for closure portion 342. Each connection point 340 corresponds to a different length belt to accommodate a range of patient girths. At one end, main portion 344 and closure portion 342 include clasp 346 with male and female connectors to provide mechanical closure and electrical circuit completion. Closure portion 342 includes connector 348 opposite clasp 346, which is connectable to each connection point 340 to change the belt length. Each connection point 340 also includes fixed compensation inductor circuit 350 matched and tuned to the corresponding belt length to provide automatic tuning and matching without the need to compensate with control system 14.

FIGS. 28A and 28B illustrate diode switches suitable as transmit/receive (T/R) switch 92 of control system 14 for use when an antenna module 16 is employed with a single coil antenna as discussed above. Passive diode switch 352 in FIG. 28A comprises crossed diodes 354, 356. The diodes are automatically switched open by larger voltages applied during transmit and closed when smaller voltages are read during receive. In one example, the switch threshold is set at about 0.7V such that the switch is open at voltages above the threshold and closed at voltages below it. Active diode switch 360 in FIG. 28B comprises PIN diode 362, direct current (DC) blocking capacitors 364, RF blocking choke coils 366, and DC power supply 368. Diode 362 is switched open and closed by externally controlled logic (not shown). The DC voltage change is confined to the PIN diode 362 and an RF choke path created by blocking capacitors 364. As a result, the RF signal cannot penetrate the DC current path due to the RF chokes and the signal to antenna module is thus turned off during a receive mode.

Figure 29A:
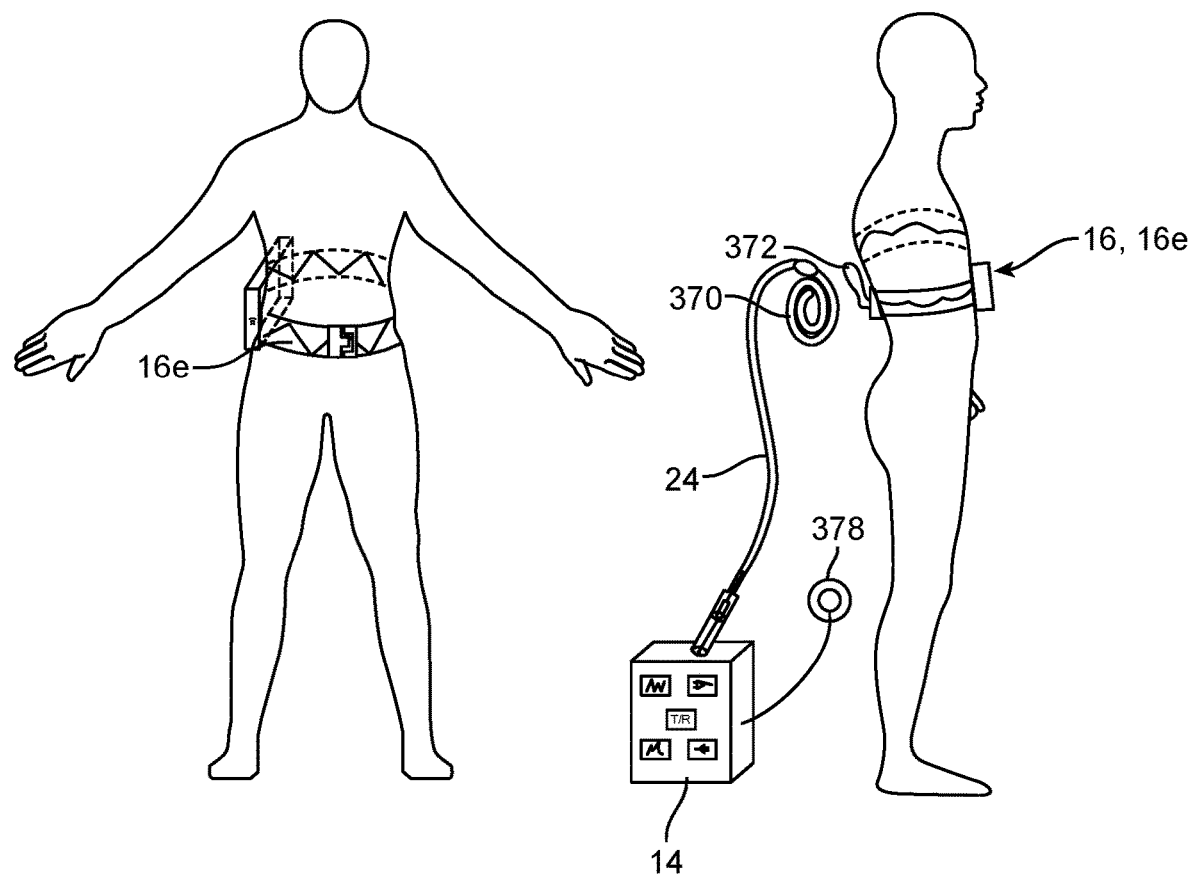
FIGS. 29A and 29B illustrate alternative antenna belt embodiments.
Figure 29B:
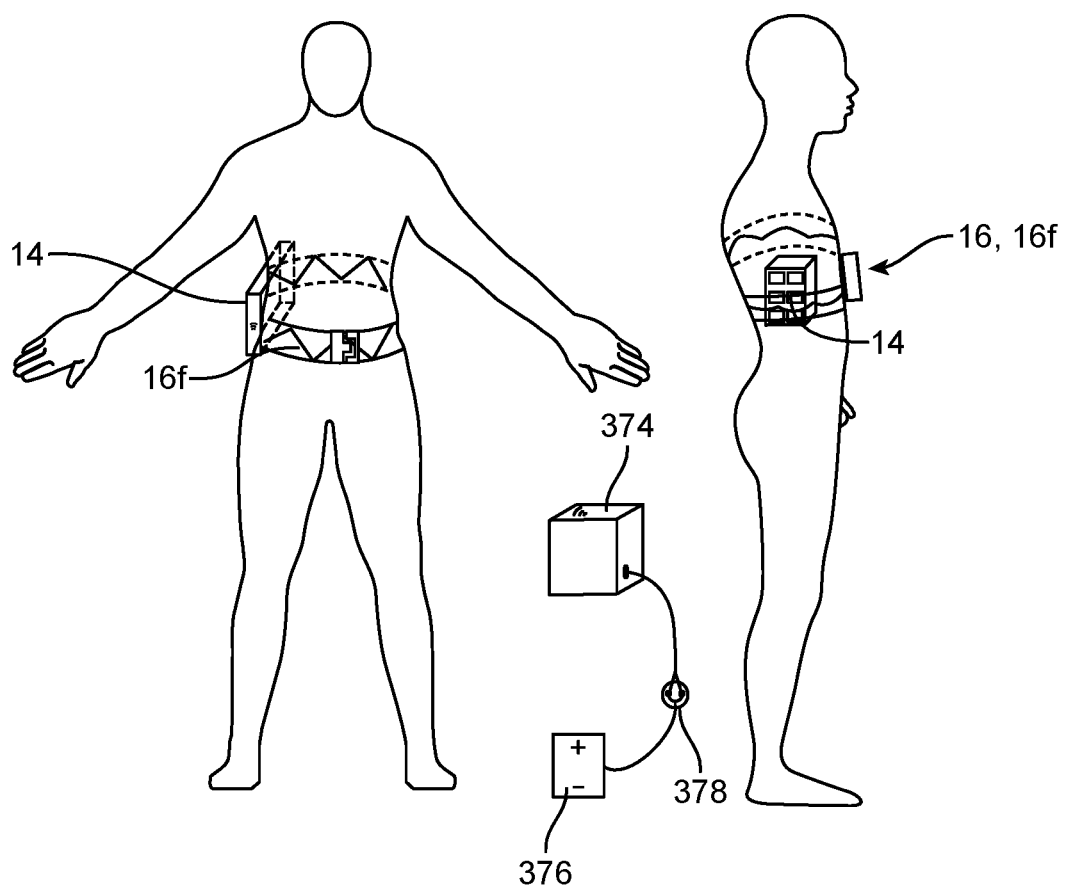

FIGS. 29A and 29B illustrate further alternative belt antenna embodiments of antenna module 16. FIG. 29A shows an embodiment in which antenna module 16 does not employ a wired connection for power and comm link 24, but instead wirelessly connects alternative belt antenna 16e to control system 14. In this embodiment power and comm link 24 and antenna belt 16e utilize a second pair of coupling coils 370, 372 to transmit the signals between the belt and the power and comm link. Apart from its second coupling coils 372 for communication with matched coil 370 on power and comm link 24, antenna belt 16e may be configured as described for any previous antenna belt embodiment. FIG. 29B describes a further alternative embodiment in which control system 14 is powered by battery and incorporated into belt antenna 16f to provide an overall system that is less restrictive for the patient. In this embodiment, control system 14 contains a wireless module which is used to communicate the required information to base station 374, which in turn communicates with a remote system (i.e. cloud data storage/wired network) as previously described. The belt-mounted battery in this embodiment may be charged via non-contact near field communication, wireless charging by being placed on charging pad 376, which in turn would receive its power directly from base station 374 or from AC power source 378. Also in this embodiment other aspects of antenna belt 16f may be configured as described above for other antenna belt embodiments.

Figure 30A:
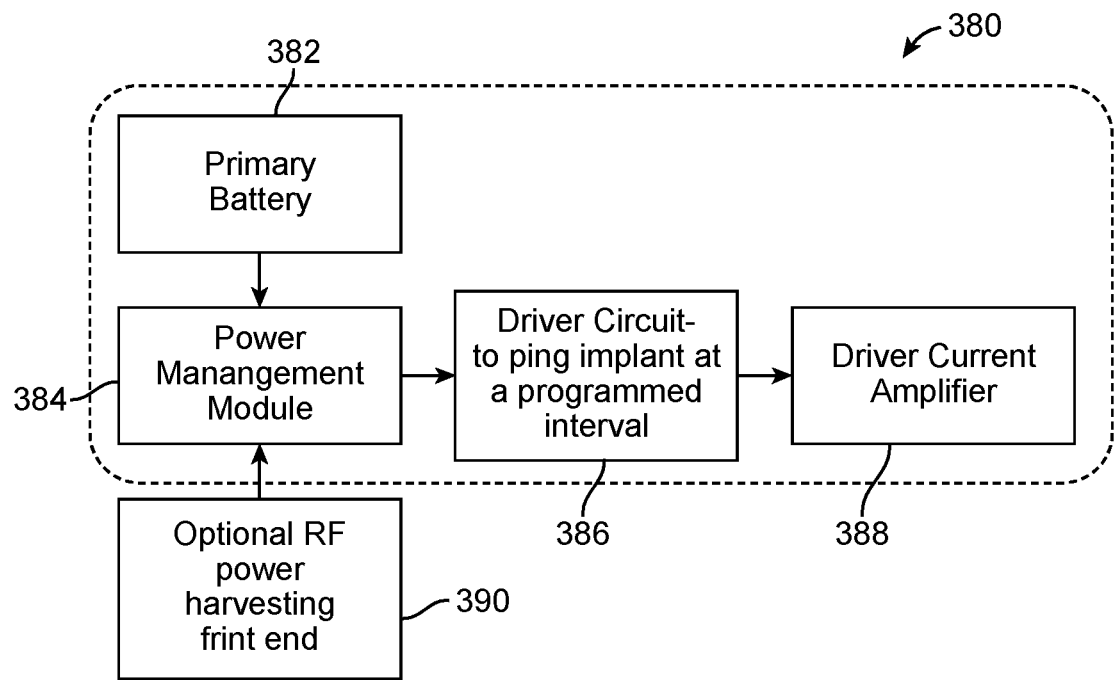
FIGS. 30A and 30B are block diagrams illustrating alternative control systems with an on-board, implanted, power supply.
Figure 30B:
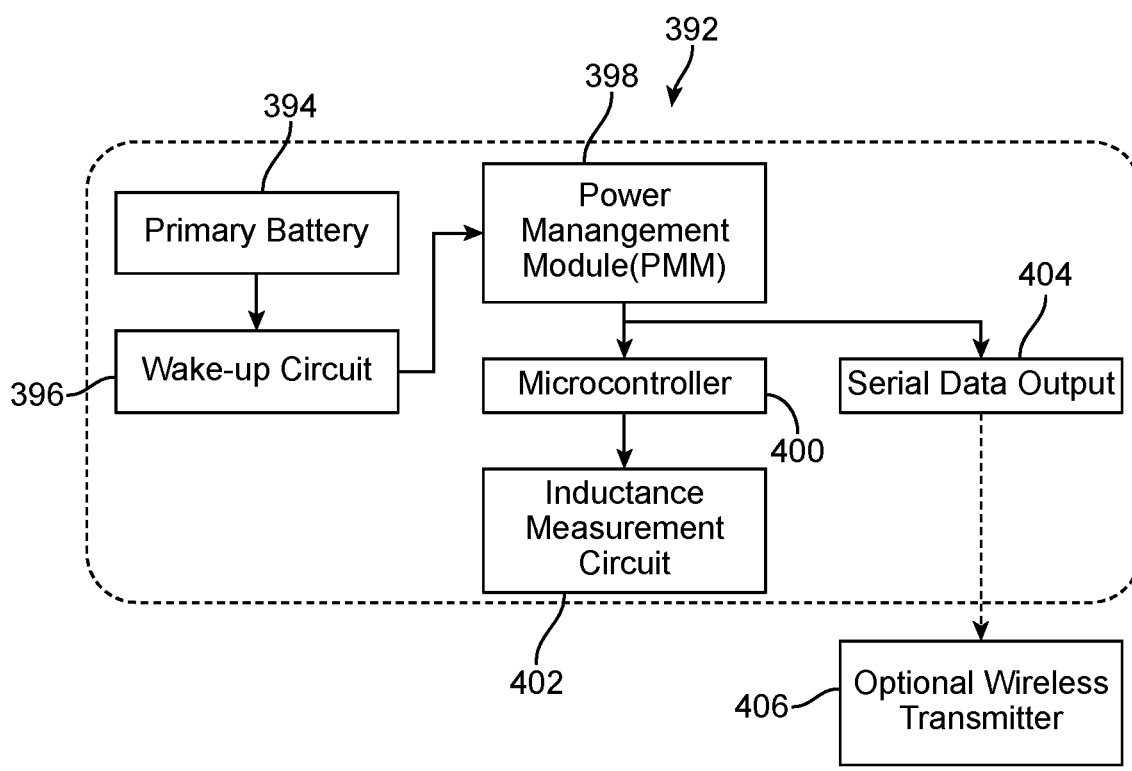
Figure 31A:
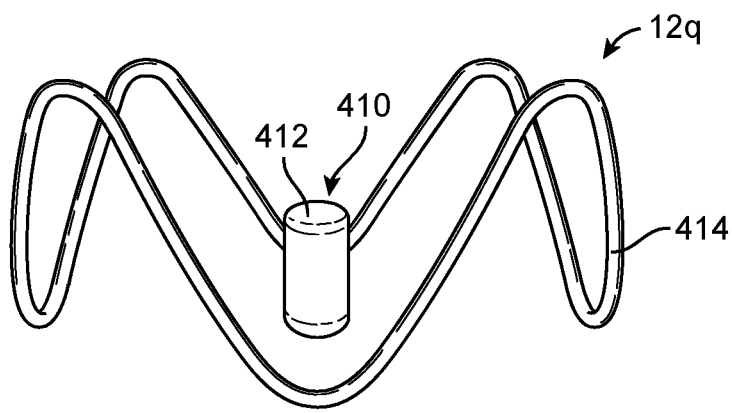
FIGS. 31A and 31B are perspective views of alternative embodiments of wireless implants with an on-board power supply and control electronics according to further embodiments disclosed herein.
Figure 31B:
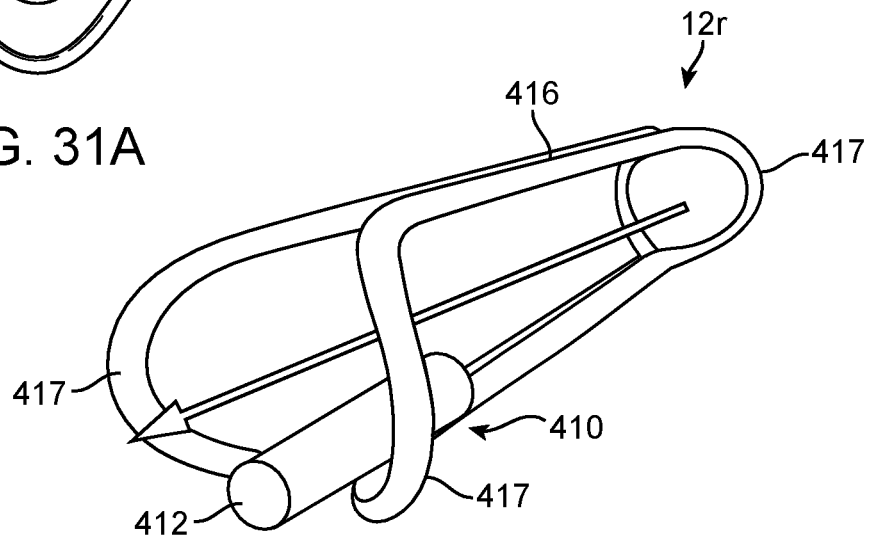

RC-WVM Embodiments with On-Board Power and Electronics and Related Control Systems In some situations it may be desirable to remove the necessity for external transmit and receive antennas, increase the communications distance of the RC-WVM implant and/or communicate with another implanted monitor/device. FIGS. 30A and 30B are block diagrams illustrating two alternative on-board electronics systems. FIGS. 31A and 31B depict alternative wireless implants 12q and 12r, including electronics modules, which may contain on-board electronics systems, for example, as shown in FIGS. 30A and 30B.

In one alternative, as exemplified by FIG. 30A, on-board electronics system 380 include primary battery 382 to increase communication distance. Other modules of electronics system 380 may include power management module 384, driver circuit 386 to drive the wireless implant coil at pre-programmed intervals and frequencies, and current amplifier/buffer 388 to interface with the wireless implant coil. In this case, battery 382 provides energy used to excite the implant coil and cause it to resonate at its resonant frequency (or to produce a measurable inductance change as explained below), but with higher power due to the power supply being on board (rather than using an external transmit coil/antenna). A stronger signal may allow a receive coil of an antenna module to be located further away (for example, under or beside the bed) from the primary coil of an RC-WVM implant, thus giving greater flexibility in positioning of patient and external device. In such an embodiment, there may be no need for the external transmit coil, only an external receive coil of the antenna module is used. In an optional alternative, RF power harvesting 390 may be employed to capture and harness an external RF signal, power a super capacitor and then perform as above. Further features possible in such an embodiment may include battery capacity and power budget estimation, or battery down select from available implant batteries.

In another alternative, as exemplified in FIG. 30B, on-board electronics system 392 includes primary battery 394 to provide energy to excite or otherwise power the wireless implant coil. Excitation or power delivery may be manually initiated or in response to a signal from optional wake-up circuit 396. Power management module 398 communicates with microcontroller 400, which is interfaced with inductance measurement circuit 402 (which may include ADC and firmware to measure inductance), and serial data port 404 to send digital data, optionally through wireless transmitter 406 if required. In one option, microcontroller 400 interfaces to an analog to digital controller ("ADC") and inductance measurement circuit 402 digitizes the inductance and ports this data to a serial data port 404 for wireless transmission to a sub-cutaneous body implant (e.g., implant 420 in FIG. 32). Additional features in such an embodiment may include battery capacity and power budget estimation.

Illustrative examples of wireless implants 12q and 12r employing on-board electronics systems are shown in FIGS. 31A and 31B. Both implants 12q and 12r include an electronics module 410 contained within a sealed capsule/container 412, which is secured to the resilient sensor construct to electrically communicate with the implant coil. Wireless implant 12q is depicted as employing a sinusoidal or "zig-zag" coil 414 with a similar construction and function to the coils of implants 12a and 12b, shown in FIGS. 2 and 2A. Wireless implant 12r is depicted as employing a "dog-bone" configured coil 416 with ears 417 having a similar construction and function to implant 12c shown in FIG. 12A. Note that the arrow in FIG. 31B illustrates direction of blood flow through the implant. Alternatively, any other implant 12 disclosed herein may be adapted with an electronics module such as module 410.

Figure 32:
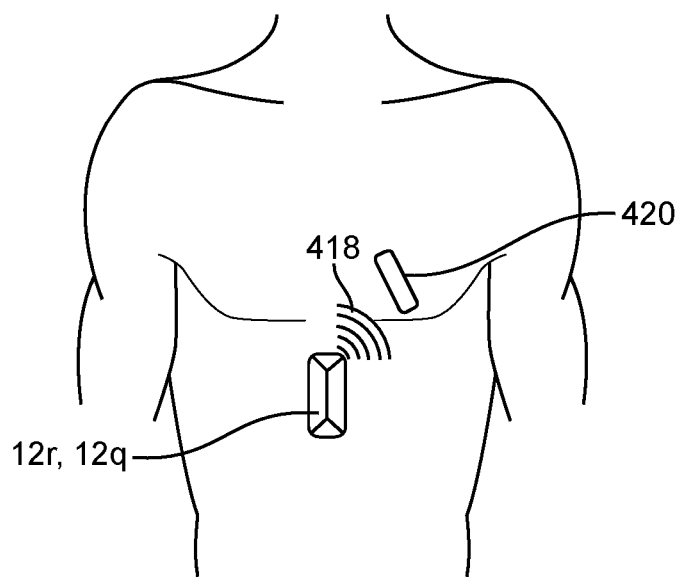
FIG. 32 is a schematic depiction of a wireless implant including on-board power and electronics communicating with an implanted cardiac monitoring device.

Another advantage of on-board electronics systems, such as system 392, is that the on-board system may be used to determine the resonant frequency and transmit a signal to a sub-cutaneous cardiac monitor/device (such as Medtronic LINQ or Biotronik BioMonitor). The subcutaneous cardiac monitor/device may be preexisting in the patient or may be implanted along with the RC-WVM implant. This architecture allows the device to potentially take multiple readings at pre-set time points or as indicated by triggers such as an accelerometer. FIG. 32 schematically depicts wireless implant 12q or 12r wirelessly communicating 418 with subcutaneous cardiac monitor/device 420. In this depiction, the wireless implant may include within electronics module 410 an on-board electronics system such as system 392 as described above. The on-board electronics system may be configured to communicate directly with the communications interface of device 420 without necessitating changes in that interface.

In yet a further alternative embodiment, when utilized with an on-board power supply as a part of an on-board electronics system, such as systems 380 or 392) wireless implants such as implants 12q, 12r, or other configurations disclosed herein, may be configured as a variable inductor without the necessity to include a specifically matched capacitance to create a tuned resonant circuit. In this case, the on-board electronics system applies a current to the implant sensor coil and then measures changes in inductance as a result of the coil-changing geometry in response to movement of the vascular lumen wall at the monitoring location where the implant is positioned. Signals based on the varying inductance measurements can then be transmitted by a communications module of the on-board electronics system, again, without the necessity of specially tuned antennas. Implants employing direct, variable inductance instead of a resonant circuit with a variable resonant frequency may be mechanically constructed as elsewhere described herein with respect to the exemplary embodiments of RC-WVM implants 12, except that a specific capacitance or capacitor to produce a resonant circuit is not required.

Hardware and Software Examples for Computer-Implemented Components

It is to be noted that any one or more of the aspects and embodiments described herein, such as, for example, related to communications, monitoring, control or signal processing, may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module. In general, the term "module" as used herein refers to a structure comprising a software or firmware implemented set of instructions for performing a stated module function, and, unless otherwise indicated, a non-transitory memory or storage device containing the instruction set, which memory or storage may be local or remote with respect to an associated processor. A module as such may also include a processor and/or other hardware devices as may be described necessary to execute the instruction set and perform the stated function of the module.

Such software may be a computer program product that employs a machine-readable storage medium. A machine-readable storage medium may be any medium that is capable of storing and/or encoding a sequence of instructions in a non-transitory manner for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, smart watch, etc.), a web appliance, a network router, a network switch, a network bridge, any machine capable of executing a sequence of instructions that specify an action to be taken by that machine, and any combinations thereof.

Figure 33:
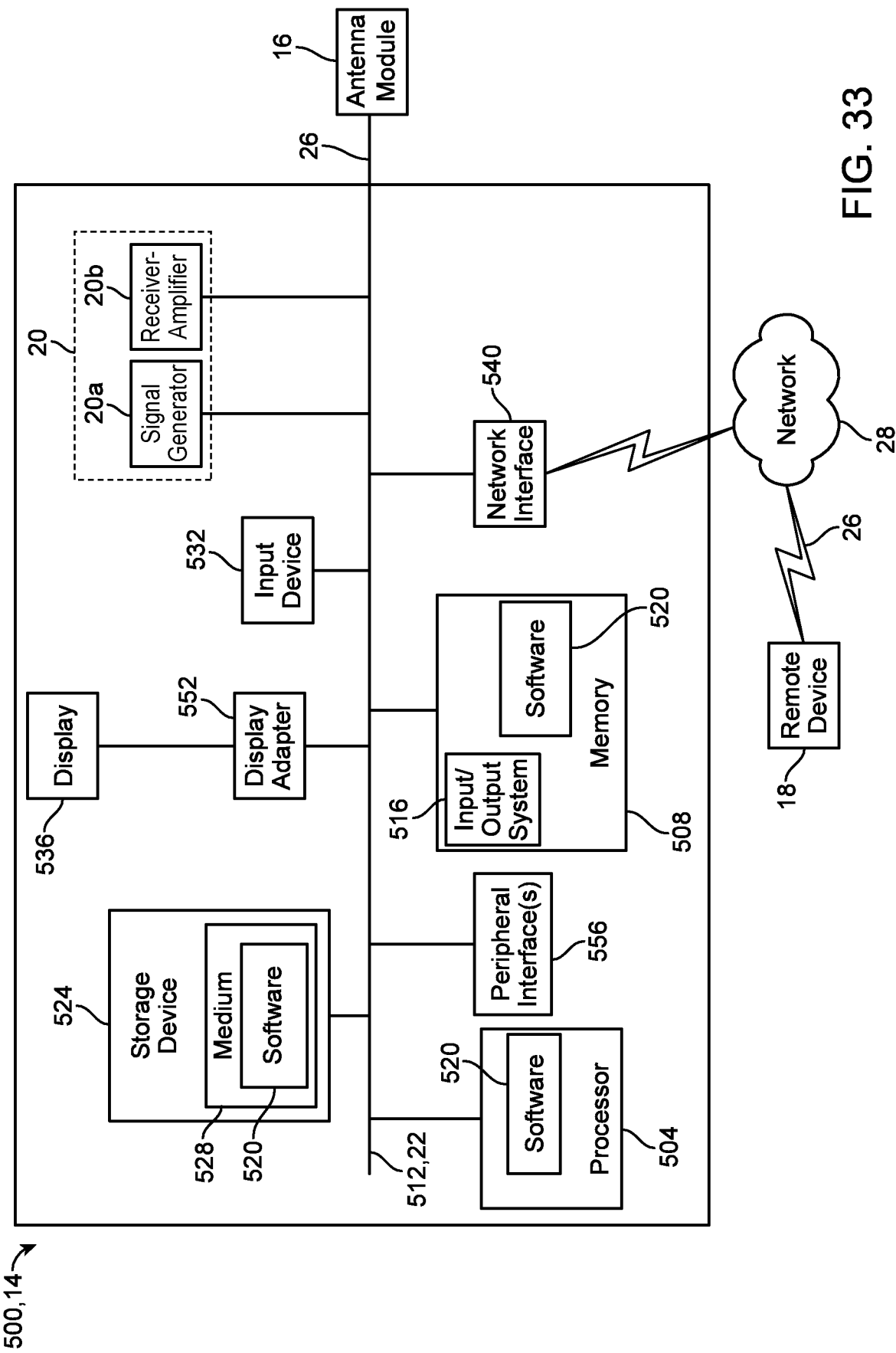
FIG. 33 is a block diagram depicting one possible embodiment of a computer-based implementation of aspects of an exemplary control system in the form of a specialized computing device or system.

FIG. 33 shows a diagrammatic representation of one possible embodiment of a computer-based implementation of one or more aspects of control system 14 in the form of specialized computing device or system 500 within which a set of instructions for causing the various modules, such as signal generation module 20a, receiver-amplifier module 20b and communications module 22, among other systems and devices disclosed herein, to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Exemplary control system 500 includes processor 504 and memory 508 that communicate with each other, and with other components, via communication bus 512. Communication bus 512 comprises all communications related hardware (e.g. wire, optical fiber, switches, etc.) and software components, including communication protocols. For example, communication bus 512 may include any of several types of bus structures including, but not limited to, a memory bus, a memory controller, a peripheral bus, a local bus, and any combinations thereof, using any of a variety of bus architectures, and may comprise communications module 22.

Memory 508 may include various components (e.g., machine-readable media) including, but not limited to, a random access memory component, a read only component, and any combinations thereof. In one example, a basic input/output system 516 (BIOS), including basic routines that help to transfer information between elements within control system 14, 500, such as during start-up, may be stored in memory 508. Memory 508 may also include (e.g., stored on one or more machine-readable media) instructions (e.g., software) 520 embodying any one or more of the aspects and/or methodologies of the present disclosure. In another example, memory 508 may further include any number of program modules including, but not limited to, an operating system, one or more application programs, other program modules, program data, and any combinations thereof.

Exemplary control system 500 may also include a storage device 524. Examples of a storage device (e.g., storage device 524) include, but are not limited to, a hard disk drive, a magnetic disk drive, an optical disc drive in combination with an optical medium, a solid-state memory device, and any combinations thereof. Storage device 524 may be connected to bus 512 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 524 (or one or more components thereof) may be removably interfaced with control system 500 (e.g., via an external port connector (not shown)). Particularly, storage device 524 and an associated machine-readable medium 528 may provide nonvolatile and/or volatile storage of machine-readable instructions, data structures, program modules, and/or other data for RC-WVM control and communication system 500. In one example, software 520 may reside, completely or partially, within machine-readable medium 528. In another example, software 520 may reside, completely or partially, within processor 504.

Exemplary control system 500 may also optionally include an input device 532. In one example, a user of control system 500 may enter commands and/or other information into the via input device 532. Examples of an input device 532 include, but are not limited to, frequency adjust 288 (FIG. 26A), as well as other alpha-numeric input devices (e.g., a keyboard), pointing devices, audio input devices (e.g., a microphone, a voice response system, etc.), cursor control devices (e.g., a mouse), a touchpad, an optical scanner, video capture devices (e.g., a still camera, a video camera), a touchscreen, and any combinations thereof. Input device 532 may be interfaced to bus 512 via any of a variety of interfaces (not shown) including, but not limited to, a serial interface, a parallel interface, a game port, a USB interface, a FIREWIRE interface, a direct interface to bus 512, and any combinations thereof. Input device 532 may include a touch screen interface that may be a part of or separate from display 536, discussed further below. Input device 532 may be utilized as a user selection device for selecting one or more graphical representations in a graphical interface as described above.

A user may also input commands and/or other information to exemplary control system 500 via storage device 524 (e.g., a removable disk drive, a flash drive, etc.) and/or network interface device 540. A network interface device, such as network interface device 540, may be utilized for connecting control system 500 to one or more of a variety of networks, such as network or cloud 28, and one or more remote devices 18 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 28, may employ a wired and/or a wireless mode of communication. In general, any network topology may be used. Information (e.g., data, software 520, etc.) may be communicated to and/or control system 500 via network interface device 540.

Exemplary control system 500 may further include display adapter 552 for communicating a displayable image to a display device, such as display device 536. Examples of a display device include, but are not limited to, LCD frequency display 292 (FIG. 26A), as well as other display types such as a cathode ray tube (CRT), a plasma display, a light emitting diode (LED) display, and any combinations thereof, which may display, for example, user prompts, alerts, or wave forms for excitation or response signals as shown in FIGS. 5A-B, 6A-B, 7A-B, 8, 10A-C and 23A-B. Display adapter 552 and display device 536 may be utilized in combination with processor 504 to provide graphical representations of aspects of the present disclosure. In addition to a display device, control system 500 may include one or more other peripheral output devices including, but not limited to, an audio speaker, a printer, and any combinations thereof. Such peripheral output devices may be connected to bus 512 via a peripheral interface 556. Examples of a peripheral interface include, but are not limited to, a serial port, a USB connection, a FIREWIRE connection, a parallel connection, and any combinations thereof.

Disclosure Summary

The present disclosure describes plural embodiments of implantable wireless monitoring sensors configured to sense changes in a dimension of a body lumen within which the sensor is implanted, as well as systems and methods employing such sensors. Aspects of disclosed sensors, systems and methods include one or more of the following, which may be combined in multiple different combinations as described herein.

For example, wireless sensor implants may be optionally configured with any of the nfollowing aspects of resilient sensor constructs, coils, variable inductance or resonance, anchor elements or electrical characteristics:

Resilient sensor constructs may
    Resilient metal frame
        Shaped wire
        Laser cut
            Nitinol
    Coil
        Plural Wire strands wrapped on frame
            Litz wire
            Bare wire
                Frame insulated
            A single wrap around frame
            Multiple wraps around frame
        Coil shapes
            Rotationally symmetric shape
                Allows placement at any rotational orientation without effecting responsiveness
            Asymmetric shape to correspond to variations in collapse of IVC in A-P and M-L directions
                Allows for discrimination between changes in A-P lumen dimension versus M-L lumen dimension
                Different radial force in different directions to facilitate proper placement Variable inductance
  Resonant circuit
    Variable inductance with fixed capacitance
      Discrete capacitor added to circuit
      Capacitance inherent in structure
Anchor elements
  Barbs or Wires
    Cranially oriented
    Caudally oriented
    Bidirectionally oriented
  Coils as anchors
  Anchor isolation structures to separate anchoring aspects from sensing aspects to avoid distortion of lumen wall at sensing location
Electrical characteristics of implant or resilient sensor construct configurations
  Capacitance selected with high Q
  Frequency
    Frequencies in range of 1 MHz
      Frequency selected to Maximize Q
      Quality factor of signal related to length of ring back signal
    High frequencies
      Permit smaller antennas
      Require more insulation
Wireless Implant sensors or resilient sensor construct configurations based on one of the above frame related aspects and one of the above coil related aspects to provide one of a variable inductance or a resonant circuit employing variable inductance and fixed capacitance, optionally with one of the above anchor element aspects may take any of the following configurations:
  Rotationally symmetric, sinusoidal or linked "Z-shape" configurations as shown in FIGS. 2 and 2A.
  "Dog bone" shaped configurations as shown in any of FIGS. 12A, 19A and 19B
  "X-bow" shaped configurations as shown in any of FIGS. 12B and 12C
  Separate coil configurations as shown in any of FIGS. 13A, 13B and 13C
  Configurations with decoupled anchoring and sensing functions as shown in any of FIGS. 12C, 14A, 14B, 15A, 15B, 16A, 16B, 17A, 17B, 19A, 19B,
  Configurations employing separate coils for anchoring and sensing, wherein the anchoring coil may also serve as an antenna as shown in any of FIGS. 16B and 18A
Systems and methods employing any of the above listed wireless sensor implants or resilient sensor constructs may further include any of the following antennas and/or deployment systems:
  Antennas
    Belt antenna systems
      Single coil switched between transmit and receive
        Diode switching
      Stretchable belt containing constant length antenna wire
      Orientation of axis of antenna coil aligned with or parallel to axis of sensor coil
    Planar antenna systems
      Separate transmit and receive coils
      Decoupling of transmit and receive coils to avoid interference
        Geometric decoupling
  Deployment
    Delivery catheter
      Delivery sheath
        Pusher element within sheath
        Gradual deployment of implant so as to partially contact lumen wall while partially contained within sheath
        Retraction of partially deployed implant so as to permit relocation The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of Y and one or more of Z; one or more of X and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A wireless vascular monitoring implant adapted to be deployed in a patient vasculature, positioned at a monitoring location in a vascular lumen and implanted in contact with the lumen wall, said implant comprising a resilient sensor construct configured to dimensionally expand and contract with natural movement of the lumen wall, wherein:
    said resilient sensor construct comprises a coil forming a variable inductance resonant circuit configured and dimensioned to extend circumferentially around the inside of the vascular lumen in engagement with the lumen wall when implanted within the lumen;
    said resilient sensor construct is configured to move with expansion and contraction of the lumen wall;
    the inductance of the resilient sensor construct changes in a known relationship to the dimensional expansion and contraction of the lumen wall;
    when energized, said resilient sensor construct produces a wireless signal indicative of said inductance, said signal being readable wirelessly outside the vascular lumen to determine a dimension of the vascular lumen;
    the resilient sensor construct further comprises a frame;

said coil is formed of multiple strands of conductive wire wrapped on the frame; and said frame consisting of a single cylindrical loop of thin, resilient metal having a sinusoidal shape or structure of repeating "Z" shapes so as to collapse into a delivery sheath to expand upon deployment from said delivery sheath into the vascular lumen.

2. A wireless implant sensor system, comprising:

a resilient sensor construct comprising a coil configured and dimensioned to be implanted in a patient vascular lumen in contact with the lumen wall around the inner circumference of the lumen wall and to dimensionally expand and contract with natural movement of the lumen wall, wherein an electrical property of said resilient sensor construct changes in a known relationship to dimensional expansion and contraction thereof; and an antenna positionable external to the patient's body configured to receive a wireless signal from said resilient sensor construct indicative of said electrical property to enable determination of a dimension of the vascular lumen; and wherein:

said coil of the resilient sensor construct has a variable inductance correlated to its dimensional expansion and contraction along at least one dimension of the vascular lumen; and said resilient sensor construct produces, when energized by an energy source, a signal indicative of inductance in said resilient sensor construct readable wirelessly outside the patient's body such that a dimension of the vascular lumen may be determined therefrom;

said coil comprises a resonant circuit having said variable inductance and a fixed capacitance to define a resonant frequency, wherein the resonant frequency varies based on changes in shape of said coil, said signal readable outside the patient's body being correlated with said resonant frequency;

said coil is configured to be energized by a magnetic field directed at the coil from outside the patient's body; and said resilient sensor construct further comprises a resilient metal frame consisting of a single cylindrical loop, and said coil comprises multiple strands of conductive wire wrapped with at least one turn around the single cylindrical loop of the resilient metal frame.

3. A wireless vascular monitoring implant and sensor system, comprising:

a sensor construct adapted to be deployed in a patient vena cava, positioned at a monitoring location in the vena cava, and implanted in contact with the vena cava wall, said sensor construct being configured to dimensionally expand and contract with natural movement of the vena cava wall, wherein said sensor construct is configured and dimensioned to extend circumferentially around the inside of the vena cava wall in engagement therewith when implanted within said lumen;

an electrical property of the resilient sensor construct changes in a known relationship to the dimensional expansion and contraction of the vena cava, and when energized, said resilient sensor construct produces a wireless signal indicative of said electrical property, said signal being readable wirelessly outside said vascular lumen to determine a dimension of the vena cava lumen;

a delivery catheter configured to receive and hold the resilient sensor construct in a compressed state for insertion through the patient's vasculature to the monitoring location in the vena cava, said resilient sensor construct configured to expand to engage the vena cava wall upon release from the delivery catheter; and an antenna positionable external to the patient's body configured to receive said wireless signal from said resilient sensor construct indicative of said electrical property to enable determination of the dimension of the vena cava lumen;

wherein the sensor construct comprises:

an expandable and collapsible cylindrical loop frame consisting of a single cylindrical loop;

at least one conductive wire disposed around said frame to form said coil with adjacent substantially parallel wire strands along the frame, said coil forming a variable inductor of a resonant circuit wherein the resonant circuit has a resonant frequency that varies based on changes in shape of said coil; and said coil produces frequency signal representative of the shape of said coil when energized by a magnetic field directed at the coil.

4. The wireless implant and sensor system of claim 3, wherein the cylindrical loop frame and at least one conductive wire are configured and dimensioned in combination to cause the resonant circuit to change characteristic frequency with natural expansion and contraction of the vena cava in response to changes in patient fluid volume state.

* * * * *